(12) United States Patent  (10) Patent No.: US 9,550,157 B2
Erdenberger et al.  (45) Date of Patent: Jan. 24, 2017

(54) SINGLE-USE MIXING AND BIOREACTOR SYSTEMS

(75) Inventors: Thomas Erdenberger, Arlington, MA (US); Richard L. Damren, Marlborough, MA (US); Colin R. Tuohey, Medway, MA (US); Michael Fisher, Ashland, MA (US); Parrish M. Galliher, Littleton, MA (US); Jonathan A. Kenney, Lakeville, MA (US)

(73) Assignee: GE HEATHCARE BIO-SCIENCES CORP, Piscataway, NJ (US)

( * ) Notice: Subject to any disclaimer, the term of this patent is extended or adjusted under 35 U.S.C. 154(b) by 72 days.

(21) Appl. No.: 14/345,256

(22) PCT Filed: Sep. 13, 2012

(86) PCT No.: PCT/US2012/055081
§ 371 (c)(1),
(2), (4) Date: Mar. 17, 2014

(87) PCT Pub. No.: WO2013/040161
PCT Pub. Date: Mar. 21, 2013

(65) Prior Publication Data
US 2014/0349385 A1    Nov. 27, 2014

Related U.S. Application Data

(60) Provisional application No. 61/607,960, filed on Mar. 7, 2012, provisional application No. 61/537,743, filed
(Continued)

(51) Int. Cl.
*B01F 13/08*    (2006.01)
*B01F 7/00*    (2006.01)
(Continued)

(52) U.S. Cl.
CPC ....... *B01F 13/0818* (2013.01); *B01F 3/04106* (2013.01); *B01F 3/04531* (2013.01);
(Continued)

(58) Field of Classification Search
CPC .............. B01F 13/0818; B01F 3/04106; B01F 3/04531; B01F 7/0025; B01F 7/00633; B01F 7/162; B01F 13/0872; B01F 15/00714; B01F 15/0085; B01F 2003/04673; B01F 2015/0011; B01F 2215/0073; B01F 13/08; C12M 23/14; C12M 27/02; C12M 23/26
(Continued)

(56) References Cited

U.S. PATENT DOCUMENTS 6,837,613 B2    1/2005 Terentiev
7,992,846 B2    8/2011 Terentiev et al.
(Continued)

FOREIGN PATENT DOCUMENTS

CN    1346287 A    4/2002
JP    02237632 A    9/1990
(Continued)

OTHER PUBLICATIONS

Supplementary European Search Report received for European Patent Application No. EP12831047.1, dated Sep. 17, 2015, 6 pages.
(Continued)

*Primary Examiner* — Jonathan Hurst
(74) *Attorney, Agent, or Firm* — Grogan, Tuccillo & Vanderleeden, LLP

(57) ABSTRACT

Disclosed are magnetic agitation mixing systems for use with flexible container reaction vessels. In one aspect of the invention, the orientation of magnetic coupling between the impeller magnets and the external driver magnets is modi-
(Continued)

fied such that the coupling is neither strictly axial nor strictly radial. Also disclosed are "receiver-less" retainer configurations whereby the single-use container need not have a rigid base that defines a cup or post to engage of rotatable agitator.

4 Claims, 28 Drawing Sheets

Related U.S. Application Data on Sep. 22, 2011, provisional application No. 61/536,546, filed on Sep. 19, 2011, provisional application No. 61/535,411, filed on Sep. 16, 2011.

(51) Int. Cl.

| | | |
|---|---|---|
| *B01F 7/16* | (2006.01) | |
| *B01F 15/00* | (2006.01) | |
| *B01F 3/04* | (2006.01) | |
| *C12M 1/06* | (2006.01) | |
| *C12M 1/00* | (2006.01) | |

(52) U.S. Cl.
CPC ........ *B01F 7/0025* (2013.01); *B01F 7/00633* (2013.01); *B01F 7/162* (2013.01); *B01F 13/0872* (2013.01); *B01F 15/0085* (2013.01); *B01F 15/00714* (2013.01); *C12M 23/14* (2013.01); *C12M 27/02* (2013.01); *B01F 2003/04673* (2013.01); *B01F 2015/0011* (2013.01); *B01F 2215/0073* (2013.01); *C12M 23/26* (2013.01)

(58) Field of Classification Search
USPC ..................................................... 435/302.1
See application file for complete search history.

(56) References Cited

U.S. PATENT DOCUMENTS

| | | |
|---|---|---|
| 2006/0092761 A1 | 5/2006 | Terentiev |
| 2009/0130757 A1 | 5/2009 | Terentiev |
| 2009/0219780 A1 | 9/2009 | Castillo et al. |
| 2010/0020635 A1 | 1/2010 | Huhta |
| 2011/0013474 A1 | 1/2011 | Ludwig et al. |
| 2011/0150674 A1* | 6/2011 | Furlan ................ F04D 13/0666 417/353 |
| 2013/0288346 A1* | 10/2013 | Tuohey ................. C12M 23/26 435/287.1 |

FOREIGN PATENT DOCUMENTS

| | | |
|---|---|---|
| JP | 2004534374 A | 11/2004 |
| JP | 2006226057 A | 8/2006 |
| JP | 2007522801 A | 8/2007 |
| JP | 2011509684 A | 3/2011 |
| WO | 2008/040568 A1 | 4/2008 |
| WO | 2008040568 A1 | 4/2008 |
| WO | 20080040568 A1 | 4/2008 |

OTHER PUBLICATIONS

First Search Report received for Chinese Patent Application No. CN201280055614.9, dated Jun. 16, 2015, 2 pages.
European Search Report dated Sep. 10, 2015 in connection with corresponding EP Application 12831047.
Chinese Office Action Dated Sep. 9, 2016.

\* cited by examiner

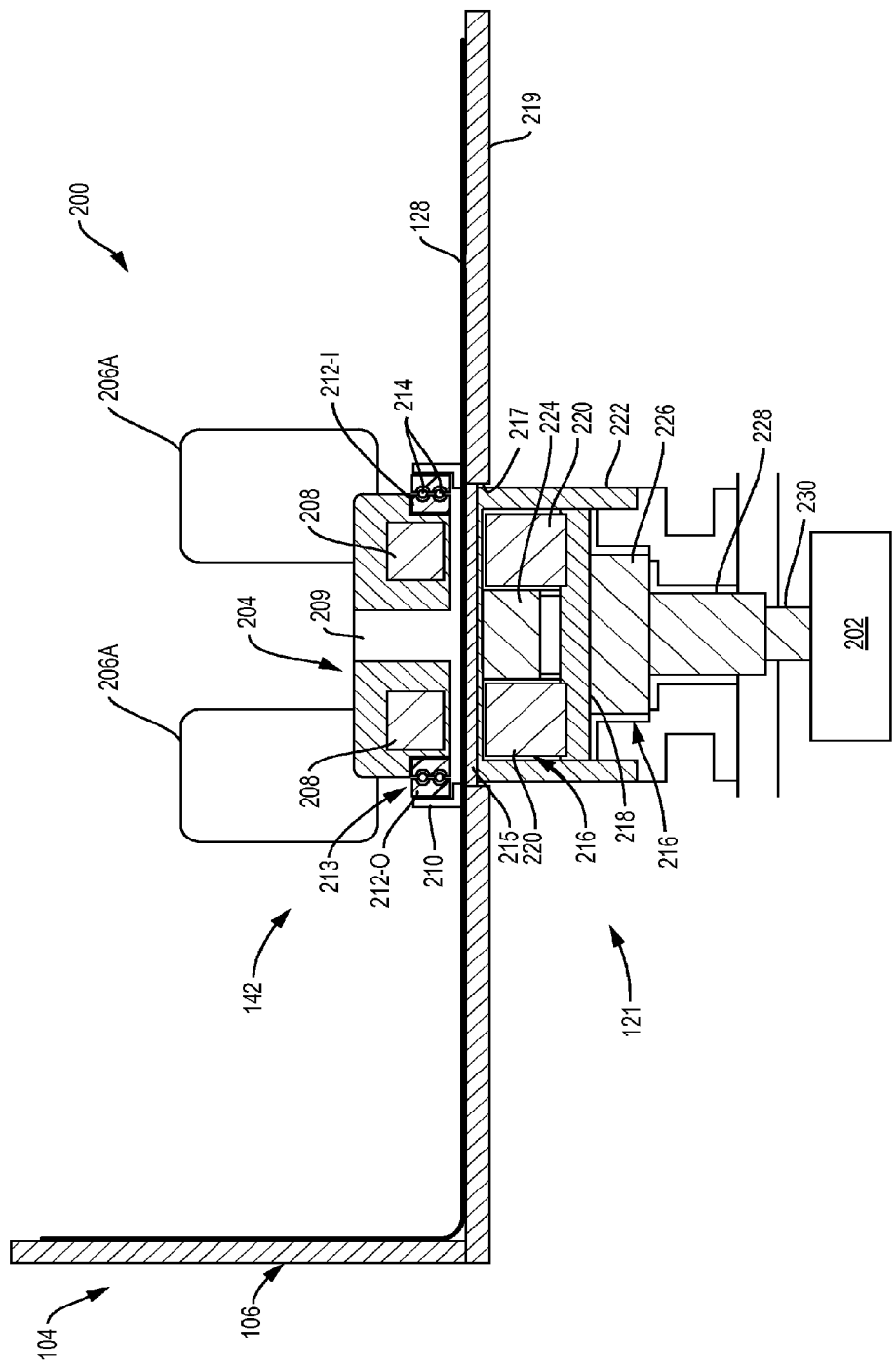

SINGLE-USE MIXING AND BIOREACTOR SYSTEMS

CROSS-REFERENCE TO RELATED APPLICATIONS

This application is a filing under 35 U.S.C. 371 of international application number PCT/US2012/055081, filed Sep. 13, 2012, published on Mar. 21, 2013 as WO 2013/040161, which claims priority to U.S. provisional patent application Nos. 61/535,411 filed Sep. 16, 2011; 61/536,546 filed Sep. 19, 2011; 61/537,743 filed Sep. 22, 2011; and 61/607,960 filed Mar. 7, 2012; the disclosures of which are incorporated herein by reference in their entireties.

BACKGROUND OF THE INVENTION

Chemical mixing systems often include an agitator mechanically connected to a drive shaft or a post that is lowered into a fluid through an opening in the top of a vessel, and then rotated using external motors. In closed systems, agitators are often connected to external motors via hydraulically sealed drive shafts. However, because of potential contamination of the fluid in the vessel and potential leaking, these types of agitator are generally not practical for mixers and bioreactors used in manufacturing of pharmaceuticals or biological materials.

Magnetic coupling of an agitator inside the vessel to a drive system or motor external to the mixer or bioreactor can eliminate contamination issues, allow for a completely enclosed system, and prevent leakage. Because there is no need to have a drive shaft penetrate the bag support structure wall to mechanically spin the agitator, magnetically coupled systems can eliminate the need for having seals between the drive shaft and the vessel. Most magnetic agitator systems include a rotating magnetic drive head outside of the vessel and a rotating magnetic agitator (also referred to in this context as the "impeller") within the vessel. The movement of the magnetic drive head enables torque transfer and thus rotation of the magnetic agitator allowing the agitator to mix a substance within the vessel.

Increasingly, in the biopharmaceutical industry, single use or disposable containers are used. Such containers can be flexible or collapsible plastic bags that are supported by an outer rigid structure such as a stainless steel shell. Use of sterilized disposable bags eliminates time-consuming step of cleaning of the vessel and reduces the chance of contamination. Combining the single use or disposable bags with the magnetic agitator system establishes a sterile environment that is especially important for biopharmaceutical manufacturing.

Magnetic agitator systems currently include particular components to both retain the magnetic agitating element in a certain position within the flexible bag during mixing, and also to maintain coupling and proper alignment between the magnetic agitator and the external magnetic drive head or system. Examples of such components include post or cup-like "receiver" structures that are formed as part of the disposable container, typically as part of a rigid bottom or base of a disposable bag. Such receiver structures added to the expense of container manufacturing—and introduce regions of possible vessel failure if the spinning agitator repeatedly comes in contact with a portion of the receiver structure.

Moreover, the fusion of a thick rigid bottom segment to a container bag also complicates the placement of other process control elements. For example, bioreactor systems typically utilize spargers for introducing a controlled amount of a specific gas or combination of gases into the bioreactor. A sparger outputs small gas bubbles into a liquid in order to agitate and/or dissolve the gas into the liquid. The delivery of gas via spargers helps in mixing a substance, maintaining a homogenous environment throughout the vessel, and is sometimes essential for growing cells in a bioreactor. Ideally, the spargers and the agitator are in close proximity to ensure optimal distribution of the gases throughout the container.

Another problem with magnetic agitator systems lies in how the impeller and driver magnets are coupled together. Two different orientations of the impeller magnets and external driver magnets are commonly used. The two orientations are axial and radial. "Axial orientation" generally means that the direction of the magnetic coupling between the internal and external rotating components is parallel to the axis around which the internal and external components are rotating. The terms "radial" and "Radial orientation" mean that the direction of the magnetic coupling between the internal and external rotating components is at an angle that is not parallel to axis of rotation, e.g., perpendicular to the axis around which the internal and external components are rotating or some intermediate angle greater than 0 degrees and less than 90 degrees relative to the axis of rotation.

In an axially coupled magnetic coupling system the direction of the coupling and de-coupling force is parallel to the direction of the magnetic coupling force. If the nonlinear attractive force between the internal and the external system components during coupling cannot be adequately controlled, the internal and external components can forcefully slam together, damaging the components. Conversely, the force required to separate the internal and external components could damage the components by overstressing the components during de-coupling as the components are pulled apart. This is especially true for the coupling components of a disposable system wherein at least some of the components might be constructed from plastic.

In a radially coupled magnetic coupling system, the nonlinear attractive forces between the internal and external components must also be overcome in a controlled manner when the components approach one other during coupling and as they recede from one other during de-coupling. In the case of a radially coupled system, the forces during coupling and de-coupling would result in what could be called a shearing force; that is, the direction of the force would be perpendicular to the magnetic coupling. If the nonlinear attractive force between the internal and the external system components during coupling cannot be adequately controlled the internal and external components can forcefully slam together on one side of the system, resulting in non-alignment of the coupling components and damaging the components. Conversely, during de-coupling when the internal and external components separate, the components could again slam together in a sideways motion and this could damage the components. Again, this is especially true for the coupling components of a disposable system wherein at least some of the components are plastic materials.

In the worst cases, misalignment of the driver and impeller magnets can lead to complete decoupling and the ejection of the agitator into the fluid volume of the container. Unless the agitator can be re-coupled to the drive mechanism, no further mixing can be accomplished and the batch may be compromised in an attempt to reseat the impeller or, failing successful re-coupling, the entire batch being processed must be discarded. The possibility of decoupling increases with the height of the agitator. In large batch containers, it can be desirable to have the agitator to have an axial shaft that extends for a substantial portion, if not the entire height, of the container and carries several separate sets of vanes, for example, to mix the top, middle and bottom of the fluid column in the container simultaneously. Because the center of gravity for such extended length agitators is at a distance from the impeller hub, misalignment can quickly lead to wobbling and, ultimately, detachment especially at high rotational speeds.

A variety of vessels, devices, components and unit operations for manipulating liquids and/or for carrying out biochemical and/or biological processes are available. Increasingly, single-use or disposable bioreactor bags and single-use mixer bags are used as such vessels. For instance, biological materials (e.g., animal and plant cells) including, for example, mammalian, plant or insect cells and microbial cultures can be processed using bioreactors that include single-use processing bags. Manufacturing of complex biological products such as proteins, monoclonal antibodies, etc.) requires, in many instances, multiple processing steps ranging from fermentation or cell culture (bacteria, yeast, insect, fungi, etc.), to primary recovery and purification. Conventional bioreactor-based manufacturing of biological products generally utilizes batch, or fed-batch processing, or continuous or perfusion mode processing with subsequent off-line laboratory analysis conducted on representative samples collected from various points of the process to ensure quality.

In order to obtain timely information regarding changing conditions within a bioreactor during its operation, the use of sensor technology has been employed. There are recognized difficulties in attaching a sensor to the inside of a flexible-walled bioreactor or flexible tubing. Further, optical, electrical, and pH sensors, for example, positioned inside a flexible bag or tubing require an attachment means that allows for a clear signal to be communicated to or from external analytical instrumentation. There is an ongoing need for an improved disposable sensor assembly and a method for integrating a disposable sensor in flexible disposable bioreactor bags and in downstream tubing.

An improved device and method for integrating a disposable sensor in a flexible bioreactor bag or tubing would also be beneficial for use in bioreactor-based manufacturing systems that include in-line sensing in order to provide real-time data.

Further, there is a need for better disposable bioreactor systems that address one or more of the aforementioned problems. There is a further need for simpler, less expensive, more efficient and/or more robust, magnetic agitation mixer systems for biopharmaceutical manufacturing.

SUMMARY OF THE INVENTION

The present invention provides several improvements over existing magnetic agitation mixing systems for use with flexible container reaction vessels.

In one aspect of the invention, a mixing system and method for mixing a fluid is provided, comprising a flexible bag for containing the fluid; a magnetic agitator located within the flexible bag and configured for mixing the fluid, the magnetic agitator comprising a rotatable hub and at least one vane or blade. A supporting structure is provided in contact with an inner surface of the flexible bag for spacing the hub away from the flexible bag; and an external magnetic drive system is provided for magnetically coupling with and driving rotation of the magnetic agitator.

Disclosed herein are "receiver-less" retainer configurations whereby the single-use container need not have a rigid base that defines a cup or post to engage a portion of the rotatable agitator. The inventors have discovered that a simpler and more robust approach can instead employ a shaped portion of the outer support structure onto which the flexible container can be draped. As the container is filled with the fluid medium, the flexible container material will conform to the shaped surface of the outer support structure to provide a receiver-less retainer for aligning the impeller magnets with the corresponding driver magnets of the external motive force. Various retentive shapes can thus be imparted to the flexible bag by the support structure, including cavities, posts, annular rings, annular grooves and the like. The invention also relates to a mixing system and method comprising a flexible bag for containing a fluid, the system further comprising a magnetic agitator disposable in the bag for mixing the fluid, the agitator configured to rotate about an axis of rotation when magnetically coupled to an external magnetic drive system. The flexible bag is configured to be supported by a bag support structure including a bag support structure wall that at least partially surrounds, supports or contains the bag during use and the flexible bag is further adapted for deformation by a shaped portion of the bag support structure to define a receiverless retainer for the agitator within the bag when the agitator is magnetically coupled to the external magnetic drive system.

In yet another aspect of the invention, an annular ring retainer or guide ring is disclosed that at least partially surrounds a peripheral edge of the agitator impeller to restrain off-centric movement of the impeller as it rotates. In one preferred embodiment, the annular ring retainer provides a raceway (or part of a raceway) to ensure low friction rotation of the impeller. For example the impeller can include a concave groove ("a race") that encircles the peripheral surface of the impeller and the outer annular guide ring can likewise includes a similar concave race facing the race at the impeller's edge such that ball bearings or the like can be loaded between the two races to provide a raceway bearing. The shape and/or orientation of the inner and outer races can also be varied to provide greater or less axial load support. The raceway bearing assembly can be used alone with a self-seating agitator or can be used in cooperation with one of receiver-less retainer designs and/or in conjunction with lateral strut/rod stabilizers as a collar joining the impeller or agitator shaft to the struts. In yet another embodiment, the agitator can include a shaft that extends from the bottom to the top of the flexible container and two raceway bearings can be deployed to retain the top and bottom portions of the full-length agitator in a proper axial orientation for rotation and mixing purposes.

In another aspect of the invention, the mixing system and method comprises a flexible bag for containing a fluid and a magnetic agitator located within the bag. The bag is configured for mixing the fluid. The magnetic agitator comprises a rotatable hub and at least one vane or blade. The agitator bearing structure is provided and attached to the magnetic agitator for allowing the hub to rotate around its central axis and for supporting the hub. A supporting structure is provided in contact with an inner surface of the flexible bag for spacing the rotatable hub away from the flexible bag. The supporting structure is attached to the agitator bearing structure. The agitator is coupled with an external drive system for rotation of the magnetic agitator.

Stabilized magnetic coupling of the impeller magnet of the agitator and the external drive magnets can be achieved in a flexible container mixing system via struts that provide lateral containment of the impeller or a shaft element. In one aspect of the invention mixing system for a fluid is provided, comprising a flexible bag for containing the fluid wherein the flexible bag has an upper portion and a lower portion; an agitator for mixing the fluid having an agitator shaft and at least one impeller attached to the agitator shaft, wherein the agitator shaft has an upper end and a lower end; a lower magnetic stabilizer having a first core magnetic support and located within the flexible bag, and a magnetic drive system, the lower end of the agitator shaft is attached to the first core magnetic support causing rotation of the agitator as the magnetic drive system rotates; and an upper magnetic stabilizer having a magnetic coupling and located within the flexible bag, and a second core magnetic support, wherein the upper end of the agitator shaft is attached to the second core magnetic support.

In a further embodiment, one or more rods or struts (and preferably three or more struts) extends from a external support structure through a side wall of the container to an agitator hub (or its associated vertical shaft) and are linked to agitator via a collar or bearing assembly that stabilizing agitator while permitting it to freely rotate about an axis. Ring-shaped raceways are one such bearing assembly that will be described in more detail below. In some embodiments it may not be necessary for the struts to be anchored by the external support structure. Instead, the container bag itself (or a reinforced belt around a portion of the bag) can be sufficient to anchor the struts. The invention accordingly relates also to a mixing system and method for a fluid, comprising a flexible bag for containing the fluid and adapted for positioning with a support structure; an agitator assembly for mixing the fluid having an agitator shaft and at least one impeller attached to the agitator shaft; and at least one wall stabilizer configured to provide a linkage between the agitator shaft and the support structure.

In another aspect, stabilization can be achieved with a top stabilizer configure to provide a linkage between the agitator shaft and a top portion of the support structure, e.g., an integral element of the support structure, a bracket or a lid. The invention accordingly relates to a mixing system and method for a fluid, comprising: a flexible bag having an upper portion and a lower portion for containing the fluid; an agitator for mixing the fluid having an agitator shaft having a lower and an upper end, and at least one impeller attached to the agitator shaft; and at least one stabilizer extending between the agitator shaft and the flexible bag. The at least one stabilizer may be configured to provide a linkage between the upper end of the agitator shaft and a top portion of a support structure.

In a further aspect of the invention, the orientation of magnetic coupling between the impeller magnets and the external driver magnets is modified such that the coupling is radial. In another aspect the magnetic coupling can be in a direction that is neither strictly axial nor strictly radial. One advantage of this quasi-radial angular coupling is better control of coupling and de-coupling forces during the actual coupling and decoupling of the magnetic coupling assembly. The selection of a particular magnetic coupling angle chosen from a range of angles between those defined as strictly axial or strictly radial allow the coupling and decoupling for a system to be better and more precisely controlled. This is because for angles between that defined as strictly axial and strictly radial, a blend of perpendicular and parallel magnetic forces with respect to the direction of relative movement of the coupling components would come into play. The selection of a quasi-radial (but not normal) coupling angle can also place the agitator in a more stable rotational configuration than either a strictly axial or strictly radial configuration would provide. The invention therefore relates to a mixing system and method comprising a flexible bag for containing a fluid; a magnetic agitator disposable in the flexible bag and configured to rotate about an axis of rotation when magnetically coupled to an external magnetic drive system; wherein the magnetic agitator comprises a hub assembly that comprises at least one magnet configured to magnetically couple with a drive magnet of opposite polarity associated with the external magnetic drive system, and further configured such that the coupling between the agitator magnet and the drive magnet occurs in a generally radial direction relative to the axis of rotation.

In yet a further aspect of the invention, new bulkhead sparger designs are disclosed that simplify the integration of spargers with the single-use container by separating the mechanisms for gas introduction from the agitator/external driver functions. Because the reaction vessels of the present invention do not require a container with a rigid base or an integrally formed receiver, each spargers can be an independent element that provides a fluid tight seal with a corresponding bulkhead opening in the outer support structure. Thus the spargers can be fitted to the flexible container at any time prior to filling of the vessel and simply aligned and locked into bulkhead holes in a simplified assemble operation. The modular nature of the spargers also makes it possible to retrieve, clean, re-sterilize and reuse the spargers, if desired. According to one aspect, the invention relates to mixing system and method, comprising: a flexible bag for containing a fluid, the flexible bag having at least one bulk head unit aperture; a bulkhead sparger adapted for sealing against the at least one aperture and providing a fluid-tight passageway to introduce a gas into the flexible bag when filled with fluid.

According to a further aspect, the invention relates to a bioreactor system and method, comprising: providing a flexible bag for containing a fluid, the flexible bag having at least one aperture; at least one bulkhead unit comprising a sparger unit, the at least one bulkhead unit sealing against the at least one aperture; a magnetic agitator in contact with an inner wall of the flexible bag and configured for mixing the fluid, the magnetic agitator comprising: at least one vane attached to the magnetic agitator, a rotatable hub, an agitator bearing supporting the hub; a supporting structure attached to the bearing for spacing the hub and bearing away from the flexible bag; and an external magnetic drive system for magnetically coupling with and driving rotation of the magnetic agitator. The invention further relates to a bulkhead disposable sensor assembly comprising: a bulkhead fitting for attaching the sensor assembly to a flexible or semi-rigid container or tubing; a bulkhead body comprising a monitoring sensor; wherein the sensor is mounted on one side of the flexible or semi-rigid container or tubing and a plate is mounted on the external side of the container or tubing wall; and wherein the sensor body is seated through the plate and positioned such that the container or tubing wall is sandwiched between the plate and the bulkhead body. In another embodiment, the bulkhead base fits within a bag or a tubing wall for attaching a disposable sensor through the bag or tubing wall, wherein the bulkhead base comprises a sensor housing surrounding the sensor, and threads or grooves for allowing a bulkhead fastener to screw or rotate into the bulkhead base.

In general, according to one aspect, the invention features include a mixing system for a fluid including a bag for containing fluid, a magnetic agitator for mixing the fluid, the magnetic agitator being in contact with an inner wall of the flexible containment structure or flexible bag, and a magnetic drive system for magnetically coupling with and driving the rotation of the magnetic agitator. As the term is used herein, a "bag" or a "flexible bag" is any of a flexible or collapsible bag, a semi-rigid vessel, and any other containment vessel capable of receiving and holding or containing a fluid. The bag or flexible bag may be a vessel having at least one wall that is flexible and/or at least one wall that is rigid or semi-rigid. As the term is used herein, a "bag support structure" is a rigid structure configured to support a flexible or collapsible bag. According to another aspect, the invention features the magnetic agitator including a rotating hub that carries at least one blade, and an agitator support attached to the hub for spacing the hub away from the flexible bag. In one embodiment of the invention, the agitator support is a bearing system coupling the hub to the flexible bag.

According to another aspect, the invention features a mixing system including a boot that fits against an outer bearing race of the bearing system to space the bearing system away from the flexible bag.

According to another aspect, the invention features the mixing system including a protrusion in an inner wall of a bag support structure containing the flexible bag. The magnetic agitator sits within this protrusion.

According to another aspect, the invention features a mixing system including a groove in an inner wall of a bag support structure containing the flexible bag. The magnetic agitator sits within this groove.

As mentioned above, one embodiment of the invention is a mixing system for mixing a fluid, comprising: a flexible bag for containing the fluid; a magnetic agitator in contact with an inner wall of the flexible bag and configured for mixing the fluid, the magnetic agitator comprising: at least one vane attached to the magnetic agitator, a rotatable hub, a bearing supporting the hub, s supporting structure attached to the bearing for spacing the hub and bearing away from the flexible bag; and an external magnetic drive system for magnetically coupling with and driving rotation of the magnetic agitator.

Another embodiment of the invention is a bioreactor system, comprising: a flexible bag for containing a fluid, the flexible bag having at least one aperture; at least one bulkhead unit comprising a sparger unit, the at least one bulkhead unit sealing against the at least one aperture; a magnetic agitator in contact with an inner wall of the flexible bag and configured for mixing the fluid, the magnetic agitator comprising: at least one vane attached to the magnetic agitator, a rotatable hub, a bearing supporting the hub, a supporting structure attached to the bearing for spacing the hub and bearing away from the flexible bag; and an external magnetic drive system for magnetically coupling with and driving rotation of the magnetic agitator.

In general, the invention features a method of mixing a fluid including the steps of providing a flexible bag for containing the fluid, inserting a magnetic agitator into the flexible bag so that the agitator contacts an inner wall of the flexible bag, providing a magnetic drive system external to the flexible bag for magnetically coupling with and driving rotation of the magnetic agitator, and mixing the fluid within the flexible bag by the external drive system rotating the magnetic agitator.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same or similar parts throughout the different views. The drawings are not necessarily to scale; emphasis has instead been placed upon illustrating the principles of the invention. Of the drawings:

FIG. 2 is a schematic cross-sectional, elevational view of an agitation system having an agitator disposed on a flexible bag within a bag support structure and a drive system external to the bag support structure according to an embodiment of the invention.

DETAILED DESCRIPTION

Figure 1A:
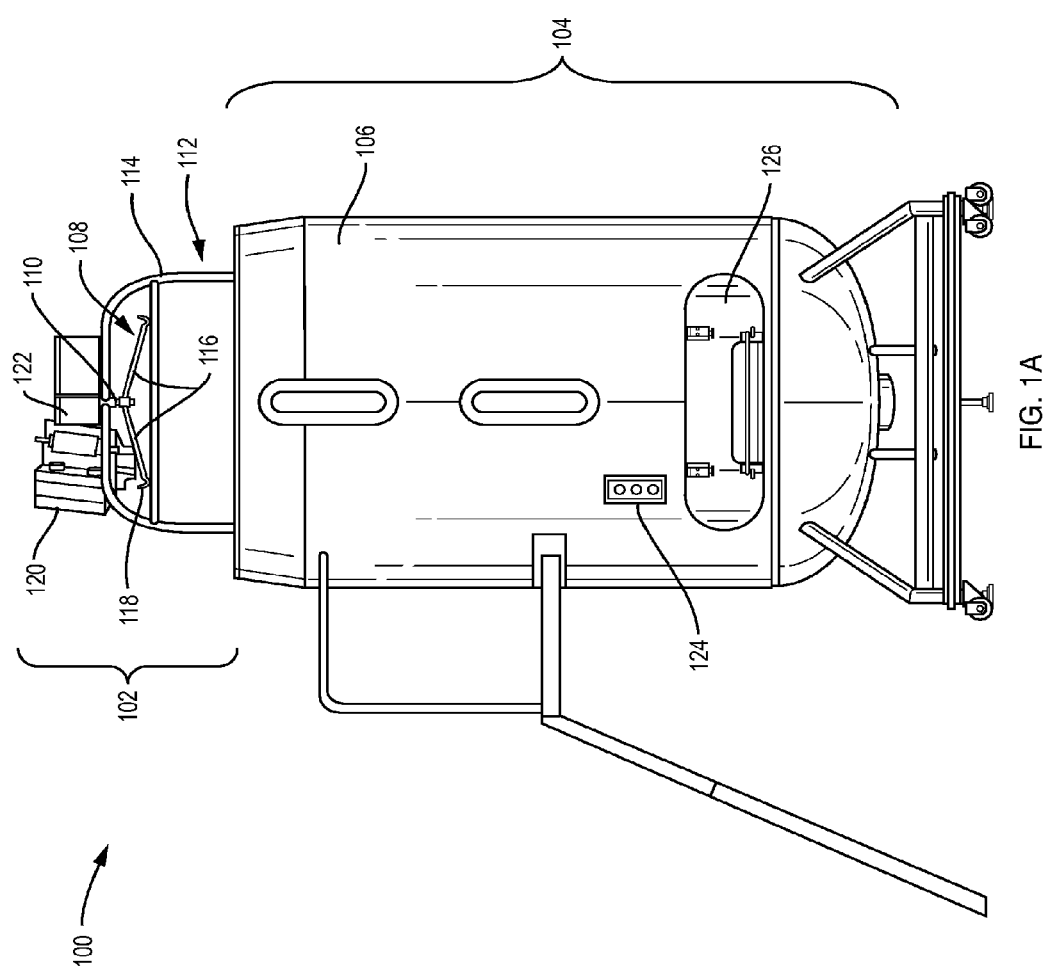
FIG. 1A is a side or elevational view of a conventional mixing or bioreactor system.

FIG. 1A depicts a conventional mixing system 100, such as a mixer or bioreactor. This system is configured to perform mixing, process operations, bioreactor functions, and/or a biological, chemical, or pharmaceutical reaction processes, depending on the application to which it is applied.

As shown in the Figures, the system 100 may include a bag support structure 104. The bag support structure 104 may have an entry port 126 positioned at a bottom part of the bag support structure 104 allowing access to the interior of the bag support structure 104. The bag support structure 104 also comprises a bag support structure wall 106 that may be formed, for example, from stainless steel, polymers, composites, glass, or other metals.

Bag support structure 104 may include a lift assembly 102 that provides support to a flexible bag within the bag support structure 104. Some examples of other structures that can be manipulated using the lift assembly 102 include agitators, spargers, or any other components of system 100. The lift assembly 102 in FIG. 1 is attached to a top portion of the bag support structure 104 via an assembly support structure 112. The assembly support structure 112 has one or more support bars 114, plates, or any other structural components suitable for supporting the desired mechanical load to be lifted by the lift assembly 102. The lift assembly 102 includes a lifting component 108 mounted on the assembly support structure 112 and movable relative to the assembly support structure 112. The lifting component 108 can be in the form of one or more lifting bars 116 including hooks 118 that can be used to support a flexible bag such as a collapsible bag in a collapsed or un-collapsed configuration. The lift assembly 102 also includes a cable 110 having a first end connected to the assembly support structure 112 and a second end connected to the lifting component 108. The cable can be made from stainless steel, polymers, natural fibers, or elastomeric materials in any suitable configuration (for example, chains, ropes, twine, etc.) capable of supporting the component to be moved. The lift assembly 102 may also include a motive device 120 connected to the cable 110 for moving the lifting component 108 relative to the assembly support structure 112. The motive device can be a motor (as illustrated), a pulley system, and/or a manual crank. The motive device 120 is used to extend or retract the cable 110, for example, resulting in raising or lowering the lifting bars 116.

The bag support structure 104 may also include an operating panel 124 on the side of the bag support structure wall 106 to control the raising, lowering, and/or stopping of the lifting bars 116. The lifting bars 116 are lowered as the cable 110 is extended from a reel 122 operatively associated with the motive device 120.

Figure 1B:
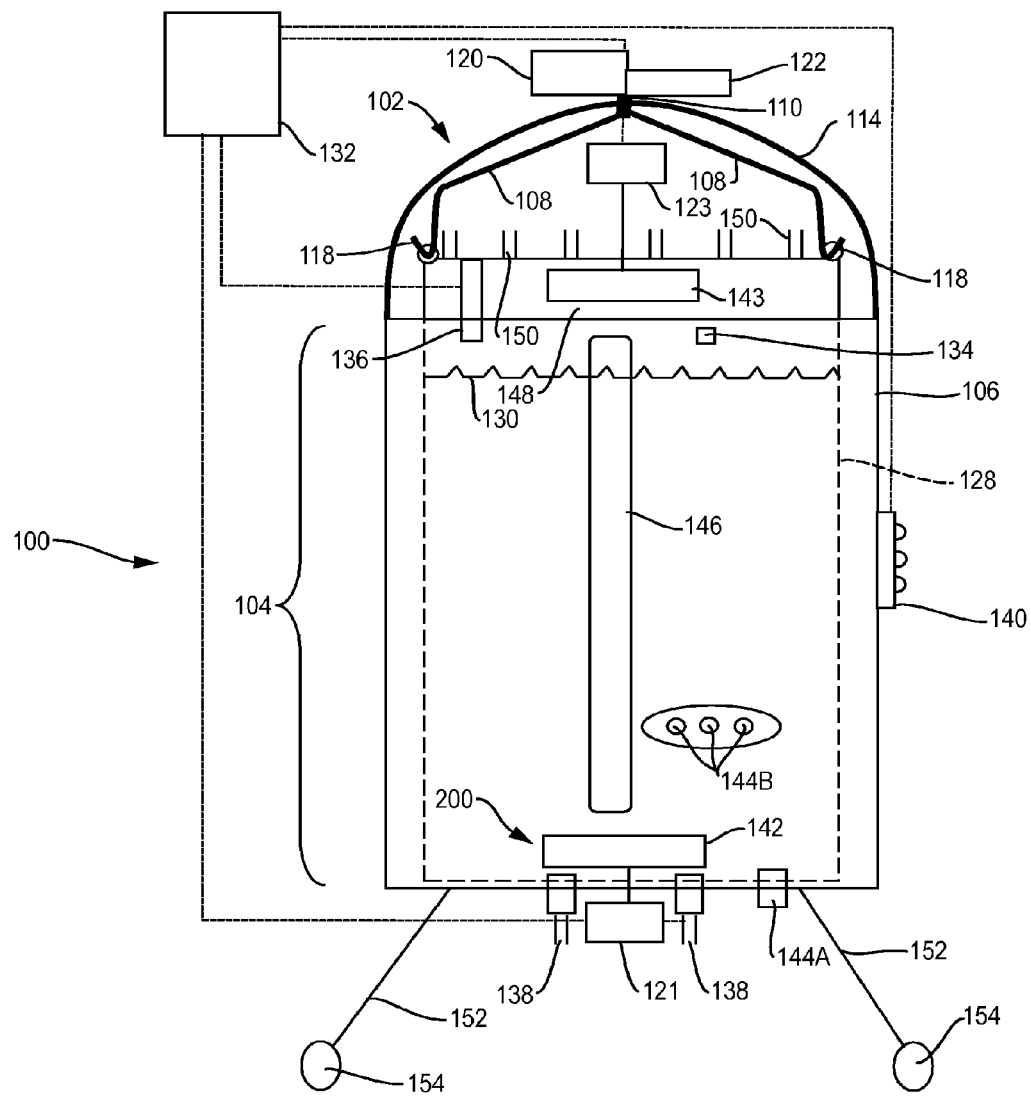
FIG. 1B is a schematic side view, partially cross-sectioned to show components of the mixing or bioreactor system of FIG. 1A.

FIG. 1B is a schematic side view showing the components of the mixing system of FIG. 1A. The system 100 includes a flexible bag 128 that fits within bag support structure 104. The lift assembly 102 is configured to lift and support the flexible bag 128.

The bag support structure 104 can have various dimensions and includes the bag support structure wall 106 that at least partially surrounds, supports, and/or contains the flexible bag 128, which is configured to be supported by the bag support structure 104. The bag support structure wall 106 can have any suitable shape capable of surrounding and/or containing the flexible bag 128. Typically, the bag support structure 104 is reusable. The bag support structure wall 106 is formed of a substantially rigid material that has non-magnetic properties such as a non-magnetic metal or alloy. Non-limiting examples of materials that can be used to form the bag support structure wall 106 include stainless steel, aluminum, glass, resin-impregnated fiberglass or carbon fiber, polymers (for example, high-density polyethylene, polyacrylate, polycarbonate, polystyrene, nylon or other polyamides, polyesters, phenolic polymers, and combinations thereof). In other embodiments, the bag support structure does not include a collapsible bag, but instead comprises a self-supporting, rigid or semi-rigid single-use container that is typically plastic. The bag support structure wall 106 can provide the bag support structure 104 with substantially airtight characteristics and can be constructed of a material to withstand system pressures that are both above and below atmospheric pressure. The bag support structure wall 106 can be constructed with single or multiple layers of material, The bag 128 can be a collapsible bag, for example, a polymeric bag. Additionally or alternatively, in one embodiment all or portions of the bag 128 comprise a substantially rigid material such as a rigid polymer, metal, and/or glass. The flexible bag 128 is typically single use or disposable and is preferably configured to be easily removable from the bag support structure wall 106, but can be reusable in other examples. The bag 128 is preferably a hermetically sealed and pre-sterilized bag capable of receiving a fluid.

The flexible bag 128 is constructed and arranged for containing a liquid 130, which contains reactants, media, and/or other components necessary for carrying out a desired process such as a chemical or biological reaction. The flexible bag 128 is configured such that liquid 130 remains substantially in contact only with the bag during use and not in contact with the bag support structure wall 106. In such embodiments, the flexible bag 128 can be disposable and used for a single reaction or a single series of reactions, after which the bag is discarded. If the liquid 130 in the flexible bag 128 does not come into contact with the bag support structure wall 106, the bag support structure wall 106 can be reused without cleaning. That is, after a reaction takes place in the bag 128, the bag 128 can be removed from the bag support structure 104 and replaced by a second bag, that can be single-use. A second reaction can be carried out in the second bag without having to clean either the first bag or the reusable bag support structure 104.

As shown in FIG. 1B, the bag support structure 104 and flexible bag 128 may include an inlet port 134 (located near the top of the bag support structure) and an outlet port 144A (located near the bottom of the bag support structure). These ports can facilitate introduction and removal of a liquid and/or gas from the flexible bag. Other inlet ports can be used to provide different gas compositions and/or to allow separation of gases prior to their introduction into the flexible bag 128. These inlet ports may be in the form of spargers 138. A sparger is a device used, for example in a bioreactor, to introduce a specific gas or air into a liquid in order to agitate and/or dissolve the air or gas into the liquid. The spargers 138 are controlled by control system 132 that is enabled to cause each sparger to function independently from one another allowing control of different gasses into the flexible bag 128. Tubing is typically connected to the inlet and/or outlet ports (134 and 144A) to form, for example, delivery and harvest lines, respectively, for introducing and removing liquid from the flexible bag 128. The bag support structure wall 106 and the flexible bag 128 may also include one or more outlet ports 144B that can be used for sampling, analyzing (for example, determining pH and/or amount of dissolved gases in the liquid), or for other purposes.

The flexible bag 128 may include one or more connections 150 that are openings, tubes, and/or valves for adding or withdrawing liquids, gases, and the like from the flexible bag 128. Each of these connections 150 can include a flow sensor and/or filter (not shown).

The bag support structure wall 106 can include a utility tower 140 for facilitating interconnection of one or more devices internal to the bag support structure wall 106 with one or more pumps, controllers, and/or electronics (for example, sensor electronics, electronic interfaces, and pressurized gas controllers) or other devices. Such devices can be controlled using the control system 132.

As shown in FIG. 1B, system 100 also includes an agitation system 200 having a lower magnetic agitator 142, which is rotated, for example, about a single axis within the flexible bag 128, using a magnetic drive system 121 external to the flexible bag 128 and bag support structure wall 106. This agitation system 200 is preferably controlled by control system 132.

The agitation and bulkhead system 200 may also include one or more bulkhead units 138 that are fit within apertures in bottom of the bag 128 and the bag support structure wall 106. As used herein, the term "bulkhead" means a fitting that attaches through a wall for allowing passage of, for example, a fluid, tubing, and so forth. The bulkhead unit 138 is a bulkhead sparger, a bulkhead sensor, or a bulkhead support in different embodiments. The bulkhead sparger is used for delivering a gas into the system 100. The bulkhead sensor is used for monitoring and testing the conditions within the system 100. The bulkhead support helps in supporting the bag or the agitator from moving during agitation in the system 100. These components are controlled by the control system 132.

The bulkhead units 138 may be utilized as spargers. A sparger is a device used to introduce a specific gas or air into a liquid in order to agitate and/or dissolve the air or gas into the liquid. A sparger also provides different gas compositions by separating the gases prior to their introduction into the bag 128. These bulkhead spargers 138 are controlled by control system 132 which is enabled to cause each sparger to function independently from one another allowing control of different gasses into the bag 128.

Additionally, the bag support structure 104 may include an antifoaming system such as a mechanical antifoaming device. The antifoaming device is a second agitator 143 that is rotated using a second drive system 123 including a motor, that is external to the flexible bag 128, in one example. The second agitator 143 is used to collapse foam contained in a head space 148 of the flexible bag 128 or used to concentrate cells and return them to the culture fluid below via centrifugal force. The antifoaming system is in electrical communication with a sensor 136 (for example, a foam sensor) via control system 132. The sensor 136 determines the level or amount of foam in the head space 148 or the pressure in the flexible bag 128, which triggers regulation or control of the antifoaming system. In other embodiments, the antifoaming system is operated independently of any sensors.

The bag support structure wall 106 may also include a site window 146 for viewing a level of liquid 130 within the flexible bag 128.

The bag support structure 104 can include legs 152 and wheels 154 attached to the bag support structure wall 106 for facilitating transport of the bag support structure 104.

FIG. 2 shows an agitation system 200 that has been constructed according to the principles of the present invention. The agitation, or mixing, system 200 comprises a magnetic agitator 142 and a magnetic drive system 121.

The magnetic agitator 142 is disposable in the flexible bag 128 and is located within the flexible bag 128. The flexible bag 128 fits tightly along the inner surface of the bag support structure wall 106 of bag support structure 104. Bag support structure wall 106 may include a bottom plate 219 that forms the bottom of the bag support structure 104. The bag support structure wall 106 may have an agitator port 217 or aperture formed in the center of the bottom plate 219.

Preferably, a disc-shaped insert 215 is fit within the agitator port 217. The magnetic drive system 121 is located external to the bag support structure 104 and as shown in FIG. 2 fits against the disc-shaped insert 215 that is installed in the agitator port 217. The flat bottom surface of the disc-shaped insert 215 provides an even interface for the external drive system 121. In the illustrated example, the bottom plate 219 of the bag support structure wall 106 forms a support surface on the bottom surface of the bag support structure 104. The bottom plate 219 and the disc-shaped insert 215 support the flexible bag 128 and the agitator 142. It should be noted that there is no rigid portion of the flexible bag 128 for receiving and holding the agitator 142. Further, there is no receiver attached or otherwise secured to the flexible bag for receiving and holding the agitator 142.

The magnetic agitator 142 performs the mixing process of system 200. Magnetic agitator 142 rotates within the flexible bag 128 in order to help mix a substance as part of a process or reaction.

Magnetic agitator 142 includes an agitator hub 204. In one embodiment, the agitator hub 204 has a squat cylindrical shape. The structural material of the hub 204 is preferably a material that is non-magnetic and corrosion resistant such as plastic.

Magnetic agitator 142 preferably includes at least one paddle-like vane or blade 206A, and preferably at least two vanes or blades 206A, attached or mounted to the agitator hub 204, or formed as one piece with the agitator hub 204. The blades 206A may project vertically from the hub 204 and can be evenly spaced around the periphery of the hub 204 so that the hub spins in a balanced fashion. The vanes/blades 206A may be for example attached to the agitator hub by pins (not shown). In other embodiments, three or more vanes/blades are fixed to the agitator hub preferably equally spaced around the perimeter of the hub. The vanes/blades 206A engage a substance, such as a fluid, within the flexible bag 128 in order to mix the substance.

The pitch of the vane/blade is typically set in order to achieve optimum mixing of the substance. Rotation of the vanes/blades produces axially-directed, or radially-directed forces that urge the substance or fluid downwards or upwards depending on the direction of rotation of the hub.

Magnetic agitator 142 may include a flow channel 209 formed in the center along a vertical axis of rotation of the agitator hub 204. This channel 209 permits axial flow within the flexible bag 128 while the magnetic agitator 142 is in operation. The agitator hub 204 is positioned slightly above the inner surface of the flexible bag 128 which allows for fluid to pass underneath the hub 204 and through the flow channel 209. This arrangement produces centrifugal flow by the spinning of the magnetic agitator 142 while fluid is swept past the sides of the magnetic agitator 142 and up through flow channel 209. As the vanes/blades 206A rotate, the rotation produces a difference in pressure that forces the fluid across this pathway. This can also be helpful during the cleaning process by easily flushing fluid around and through the magnetic agitator 142. Depending on the pitch of the blades, and the direction of rotation during operation of the agitator, fluid could pass in the other direction, down through flow channel 209 and out under magnetic agitator 142.

The magnetic agitator 142 preferably includes at least two hub magnets 208 attached or imbedded within the plastic agitator hub 204. These magnets are typically set into voids that are either molded or machined into the body of the agitator hub 204 and oriented such that the magnetic field is directed along the vertical axis of the hub 204 for compatible attraction with the magnetic drive system 121.

Preferably, the magnetic agitator 142 includes more than two hub magnets 208 that are spaced equidistantly around the perimeter of the agitator hub 204 in a circular fashion forming an array of magnets of an even number. The number of hub magnets is determined based on the desired magnetic flux needed and also the physical size constraints of the hub 204. Typically, the larger the bag support structure, the more magnets needed. The hub magnets 208 are preferably high performance rare earth magnets that produce stronger magnetic fields. For example, a magnet made from neodymium-iron-boron is used in one embodiment. As shown in FIGS. 2-6, an agitator bearing structure 213 may be attached to the magnetic agitator 142, for allowing the hub 204 to rotate around its central axis, and for supporting the hub 204 inside and in contact with the flexible bag 128, the flexible bag 128 disposed on an upper surface of the bottom plate 219. The agitator bearing structure 213 can be a bearing assembly including roller or ball bearings.

The bearing assembly may include an inner bearing race 212-I and an outer bearing race 212-O, with the inner bearing race 212-I being attached to the lower perimeter of the agitator hub 204 and specifically disposed in a recess formed in the bottom outer edge of the hub 204. The inner bearing race 212-I can be coupled or mated with the outer bearing race 212-O via a double ball bearing configuration. For this configuration, the ball bearings 214 extend through the races with spacers separating (not shown) each ball bearing 214 from one another. The combination of the bearing races 212-I/212-O and the double ball bearings 214 allows the hub 204 to freely rotate around its axis with little or no friction on the flexible bag 128 that is disposed on or resting on the bottom plate 219.

The ball bearing configuration is typically either a single ball or a multiple ball arrangement. The single ball arrangement is characterized by having only one level of ball bearings versus two for the double ball bearing arrangement.

Figure 3A:
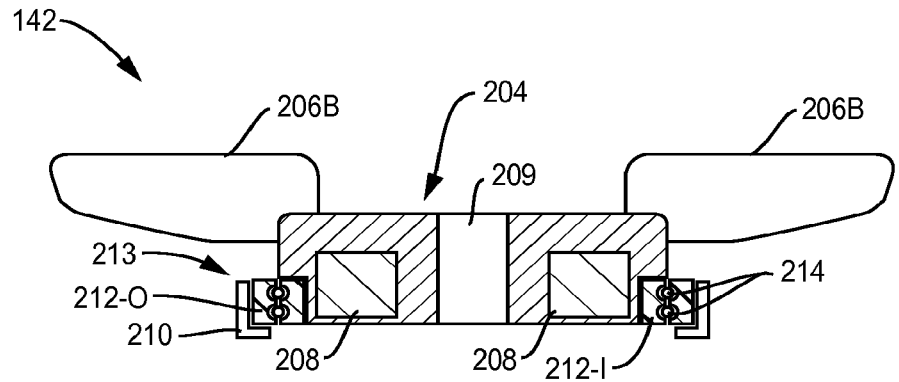
FIG. 3A is a schematic cross-sectional view of an agitator having different shaped vanes according to an embodiment of the invention.
Figure 3B:
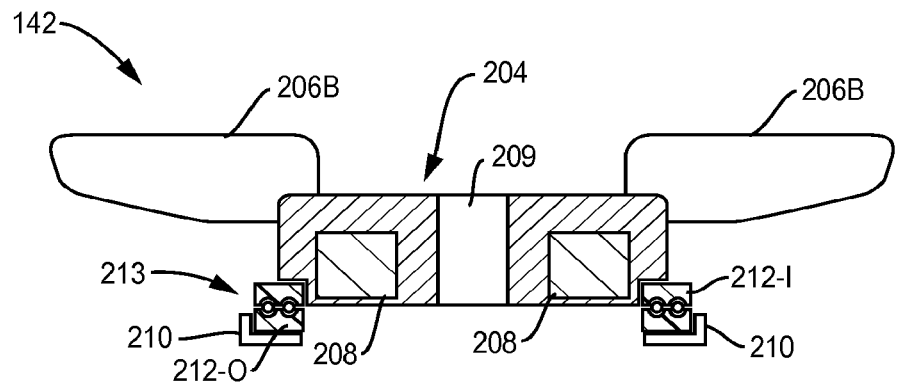
FIG. 3B is a schematic cross-sectional view of the agitator of FIG. 3A including a vertical-type of bearing structure.

The bearing configuration can be of a radial bearing, angular contact bearing, or thrust bearing type. In FIG. 3A the agitator bearing structure 213 is a double ball angular or axial contact bearing structure, the bearing races of which may be sealed or unsealed. Use of unsealed ball bearings for the agitator bearing structure allows for fluid to flow around the ball bearings providing lubrication (i.e. lower friction) and cooling of the bearings during use. The bearing configuration provides an overall low-friction support to the agitator. FIG. 3B shows another possible ball bearing structure in which the agitator bearing structure 213 is aligned in an axial or vertical manner. In this arrangement the outer bearing race 212-O is located at least partly below the hub 204. In this embodiment, that also shows blades/vanes 206B, which could be of any other type, the alternative bearing structure 213 is rotated 90° compared to the solution shown for example in FIG. 3A. In FIG. 3A the agitator bearing structure is aligned in a radial manner. In FIG. 3B, the bearing structure is aligned in an axial manner and in this way the spacing between the hub 204 and the bag 128 can be further increased in a simple manner, since the outer bearing race 212-O rests against the lower part of a boot 210 which is connected to the bag 128.

The ball bearings and inner/outer bearing races are preferably made from a material that is corrosion resistant, low cost, lightweight, and/or disposable. This allows for the bearing configuration to be discarded after each use or alternatively be easily sterilized/cleaned for reuse. Bearings made entirely of ceramic material may be superior to metallic or stainless steel bearings in any application requiring stronger magnets, high RPMs, a need to reduce overall weight, or for extremely harsh environments where high temperatures and corrosive substances are present. Ceramic materials that may be suitable for use in bearings incorporated in an embodiment of the disclosed apparatus include silicon nitride ($Si_3N_4$), zirconium oxide ($ZrO_2$), aluminum oxide ($Al_2O_3$) or silicon carbide (SiC). Bearing races can also be made from plastic or a nickel-beryllium alloy. In a prototype of the disclosed agitation system we used zirconium oxide, $ZrO_2$ (Xing Lun Bearings Group Limited, Ningbo, China). In addition to ceramic materials such as zirconium oxide, and a hybrid ceramic such as silicon nitride, other suitable materials that can be used to form the ball bearings include, for example, a plastic material, chrome, or stainless steel. Ball retainers and seals can be machined from PEEK® (Victrex® Bearings Suppliers) or TECAPEEK® (ENSINGER, GmbH FED REP GERMANY, Nufringen) or any other high strength polymeric material. Ball retainers can also be made from ceramic, steel, nylon, polyimide, phenolic, Bakelite, copper, or bronze.

Ceramic's glass-like surface provides an extremely low coefficient of friction in comparison to a metallic surface. Ceramic balls require less lubricant and have a greater hardness than stainless steel balls, properties that contribute to increased bearing life. Ceramic's thermal properties are better than those of stainless steel balls, resulting in less heat generation and heat retention at high speeds. Full ceramic bearings are highly corrosion resistant, and are non-conductive and non-magnetic.

As shown in FIG. 2, the agitator hub 204 is positioned within a supporting structure 210 for spacing the hub 204 away from the flexible bag. The supporting structure 210 is in contact with the flexible bag 128 and may comprise an annular-shaped boot structure for reducing contact between the agitator 142 and inner surface of the bag 128.

Further, in FIG. 2, the supporting structure 210 is an annular-shaped boot structure in contact with the inner surface of the flexible bag 128 and is located on the bottom surface of the flexible bag 128. A lower face of the boot 210 is disposed directly on the inner surface of the flexible bag 128 to support the outer bearing race 212-O above the flexible bag 128. The boot 210 is typically a plastic ring, washer, or bushing and is preferably comprised of a flexible polymeric material such as silicon or EPDM (ethylene propylene diene Monomer (M-class) rubber). The agitator hub 204, which in FIG. 2 is attached to the bearing structure 213, rotates along the bearing assembly with the outer bearing race 212-O press fit within boot 210. The magnetic drive system 121 controls the rotation of the magnetic agitator 142 via magnetic forces external to the bag support structure 104 and through the non-metallic or non-ferrous, disc-shaped insert 215. As shown in FIG. 2, the magnetic drive system 121 is situated external to the bag support structure 104 and flexible bag 128. Torque is transmitted from the magnetic drive system 121 to the magnetic agitator 142 due to the magnetic forces between the magnetic drive system 121 and the hub magnets 208 embedded within the magnetic agitator 142.

The magnetic drive system 121 may include a drive head 216 that fits within a drive head cowling 222. The drive head 216 may be cylindrically-shaped and rotates within the non-rotating drive head cowling 222.

The magnetic drive system 121 preferably includes at least two drive magnets 220 attached or imbedded within the drive head 216 and positioned below the disc-shaped insert 215. These drive magnets 220 are typically installed within either molded or machined recesses that are formed into the drive head 216 and oriented so that the magnetic field is directed parallel to the hub magnets 208 and parallel to the axis of rotation but with a north-south orientation that is compatible for attraction between the drive magnets 220 and hub magnets 208.

Preferably, the magnetic drive system 121 includes more than two drive magnets 220 spaced equidistantly around the perimeter of the drive head 216 forming an array of magnets. The number of drive magnets is preferably the same as the number of hub magnets. The drive magnets 220 provide the magnetic force needed to enable torque transfer to drive the magnetic agitator 142 within the flexible bag 128. The drive magnets 220 in one embodiment of the disclosed system are 38-50 Newtons; and the hub magnets 208 are also 38-50 Newtons strength. Various combinations may be used. As the drive magnets 220 rotate, they cause the magnetic agitator 142 to rotate due to the magnetic attraction between the hub magnets 208 and drive magnetic agitator 142 to rotate due to the magnetic attraction between the hub magnets 208 and the drive magnets 220. The magnetic forces produced by movement of the drive magnets 220 cause the opposing poles of the hub magnets 208 to react by moving in the same direction of rotation so that when the drive head 216 rotates, the magnetic agitator 142 rotates. The drive magnets are rare earth magnets that produce stronger forces of attraction as compared to standard magnets.

The drive head 216 may include a number of components for supporting and aiding the drive head 216 in terms of rotation at the outer surface of the disc-shaped insert 215. The drive head 216 may include a drive head base 218 for supporting the drive magnets 220 within the drive head cowling 222. The drive head cowling 222 has a hollow cylindrical form for surrounding the drive head base 218 along with the inner drive magnets 220. The drive head 216 includes a lazy-susan or a thrust bearing 224 for enabling it to rotate against the non-rotating drive head cowling 222.

The lazy-susan bearing 224 is situated at the top center portion of the drive head 216 on its axis of rotation, and between the drive magnets 220. The lazy-susan bearing 224 interacts along the inner face of the drive head cowling 222 causing rotation of the drive head 216. The drive head 216 may also include a thrust plate 226 which is attached to the bottom of the drive head base 218 along the center axis of the drive head 216 in parallel with the lazy-susan bearing 224.

The magnetic drive system 121 includes a number of components that connect the motor 202 to the drive head 216 in order to produce and control rotation of the drive head 216 and thus the rotatable hub 204. The motor 202 within the magnetic drive system 121 is typically an electric drive motor such as a variable speed electric motor, a pneumatic driven motor, a hydraulic drive motor, or the like. The motor 202 may be connected directly to a motor shaft 230. The motor shaft 230 may be supported and terminates in a thrust bearing 228. The thrust bearing 228 may be connected directly to the thrust plate 226 of the drive head 216. This causes rotation of the drive head 216 including the drive magnets 220 when the motor 202 is in operation. The thrust plate is of a larger diameter than the thrust bearing which is of a larger diameter than the motor shaft. Therefore, the thrust plate is concentrically received over the thrust bearing which is concentrically received over the motor shaft. These driving parts within the magnetic drive system 121 are together axially aligned. As the magnetic drive system 121 begins rotation, the magnetic agitator 142 automatically orients and aligns with the drive head due to the magnetic attraction.

FIG. 3A shows an alternative agitator embodiment having different shaped blades/vanes 206B. These blades/vanes 206B are also shown in FIG. 3B in connection with the alternative bearing structure 213. In this alternative, the agitator 142 includes a thin wing-shaped set of blades or vanes 206B attached to the agitator hub 204 that project radially from the hub 204 and have generally rectangular profiles. The wing-shaped vanes of FIG. 3A may be suitable for use in a bioreactor having spargers beneath the vanes 206B. The variation of shapes for the vane impacts both the torque and extent of mixing/agitation. Vanes 206A in FIG. 2 are able to mix a larger amount of substance during each rotation since they are able to engage more volume due to the vane having a larger surface area. Despite vanes 206B having less surface area, they can rotate at a faster speed and cause less friction during each rotation due to the slim shape. In an alternative set of examples, the vane or blade has a circular shape, square shape, or rectangular shape, to list a few. While FIGS. 2 and 3 describe an agitator having two blades/vanes, an alternative example is an agitator having three or more blades/vanes attached to the agitator hub. While the vanes/blades are mounted or attached to the agitator hub in FIGS. 2 and 3, alternatively the vanes/blades are integrated with the agitator hub. FIG. 3A shows a double ball angular or axial contact bearing structure 213.

Figure 4:
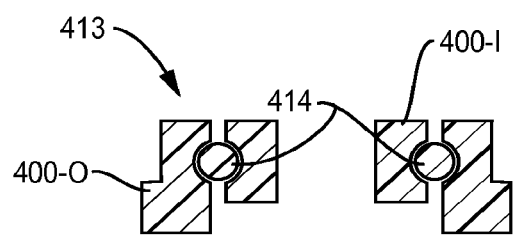
FIG. 4 is a schematic cross-sectional view of a variation of the bearing configuration for the agitator according to an embodiment of the invention.

FIG. 4 shows an alternative agitator bearing structure 413 having a different bearing configuration used for supporting the hub 204. This bearing configuration includes a single level of ball bearings 414 (single ball bearing) coupled between an inner bearing race 400-I and an outer bearing race 400-O. The outer bearing race 400-O includes an L-shaped cross-section that in effect integrates the boot into the outer bearing race 400-O in order to aid in raising the hub slightly above the inner surface of the flexible bag and bag support structure (not shown in FIG. 4). The inner bearing race 400-I is attached to and surrounds the perimeter of the hub 204 and is slightly shorter than the L-shaped outer bearing race 400-O so that it can be spaced above the bottom of the bag support structure 104 or flexible bag 128. The inner bearing race 400-I is coupled with the outer bearing race 400-O via one level of ball bearings 414 at an upper portion of the outer bearing race 400-O.

Figure 5:
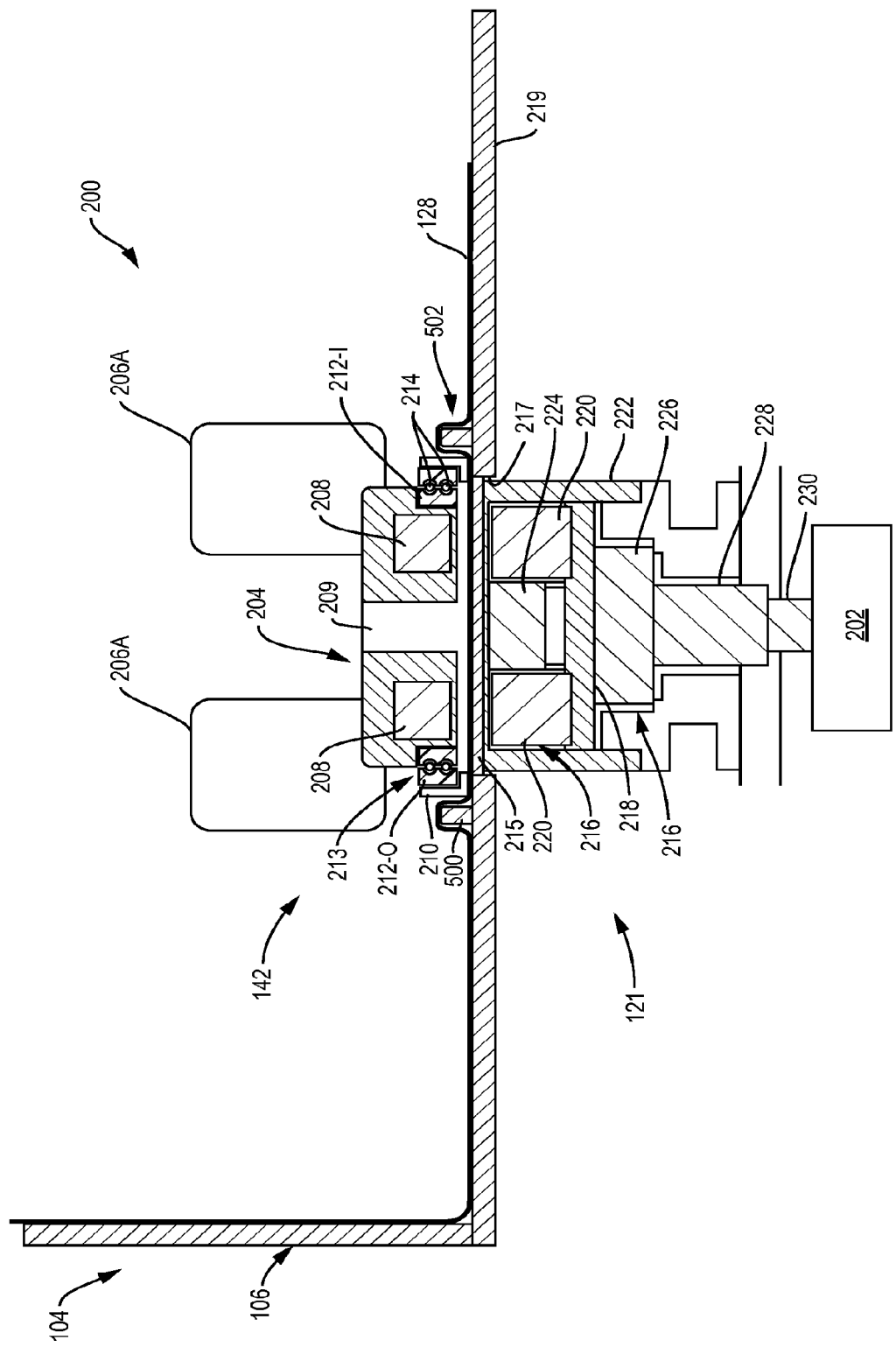
FIG. 5 is a schematic cross-sectional, elevational view of an agitation system including an annular bag support structure wall protrusion to which the flexible bag may conform, the annular bag support structure wall protrusion surrounding and positioning the agitator according to an embodiment of the invention.

FIG. 5 shows a magnetic agitator 142 similar to that shown in FIG. 2. However, in this example it is shown that the magnetic agitator 142, with agitator bearing structure 213 and the boot 210 in contact with an inside surface of flexible bag 128 adapted for deformation, fits within a shaped portion of the support structure 104. The shaped portion may be at least one of a cavity, ring-like protuberance or protrusion, groove or a post for retaining the flexible bag 128 and the fluid-agitating agitator 142. Preferably, the shaped portion is an annular shaped bag support structure wall protrusion or projection 500. The protrusion 500 is located in an inner wall of the bag support structure 104, which contains the flexible bag 128 and projects above the top surface of the bottom plate 219 of the bag support structure wall 106 and is outside the wall of the flexible container. In this way, the flexible bag 128 can be sandwiched between the magnetic agitator 142 and the bag support structure 104. In one embodiment of the invention, the annular protrusion 500 is formed in the bottom plate 219 of the bag support structure wall 106 in the shape of a circle, as viewed from above, in order to support and maintain the magnetic agitator 142 in a central position on the inner surface of the flexible bag 128. In other embodiments, the annular protrusion 500 is formed in a side or top plate of the bag support structure wall 106, in order to support and maintain the magnetic agitator 142 in a central position on an inner surface located at or near the top or at the side of the flexible bag 128. In other embodiments, multiple annular protrusions may be formed in a plate of the bag support structure wall in order to provide alternative locations for the agitator and/or to add multiple agitators in the same bag. In some embodiments, the protrusion is integral with the bottom, side, or top plate; in other embodiments, a separate washer structure is secured to the bottom, side, or top plate. In particular, the protrusion 500 protrudes inwards towards the center of the flexible bag 128 and is sized so that the boot (supporting structure) 210 can be engaged with the protrusion 500 and fits against an inner side of this protruding portion 502. The agitator bearing structure 213 fits within the boot 210 so that the magnetic agitator 142 is retained in a predetermined position with respect to the bag support structure wall 106. This arrangement stabilizes the agitation system 200 during the mixing process and prevents it from moving away from its intended aligned location. The protrusion 500 also allows for positioning or holding of the flexible bag 128 within the bag support structure 104. As disclosed above, other protrusion shapes can be formed in the bottom, side, or top plate 219 of the bag support structure wall 106 while serving the overall objective.

Figure 6:
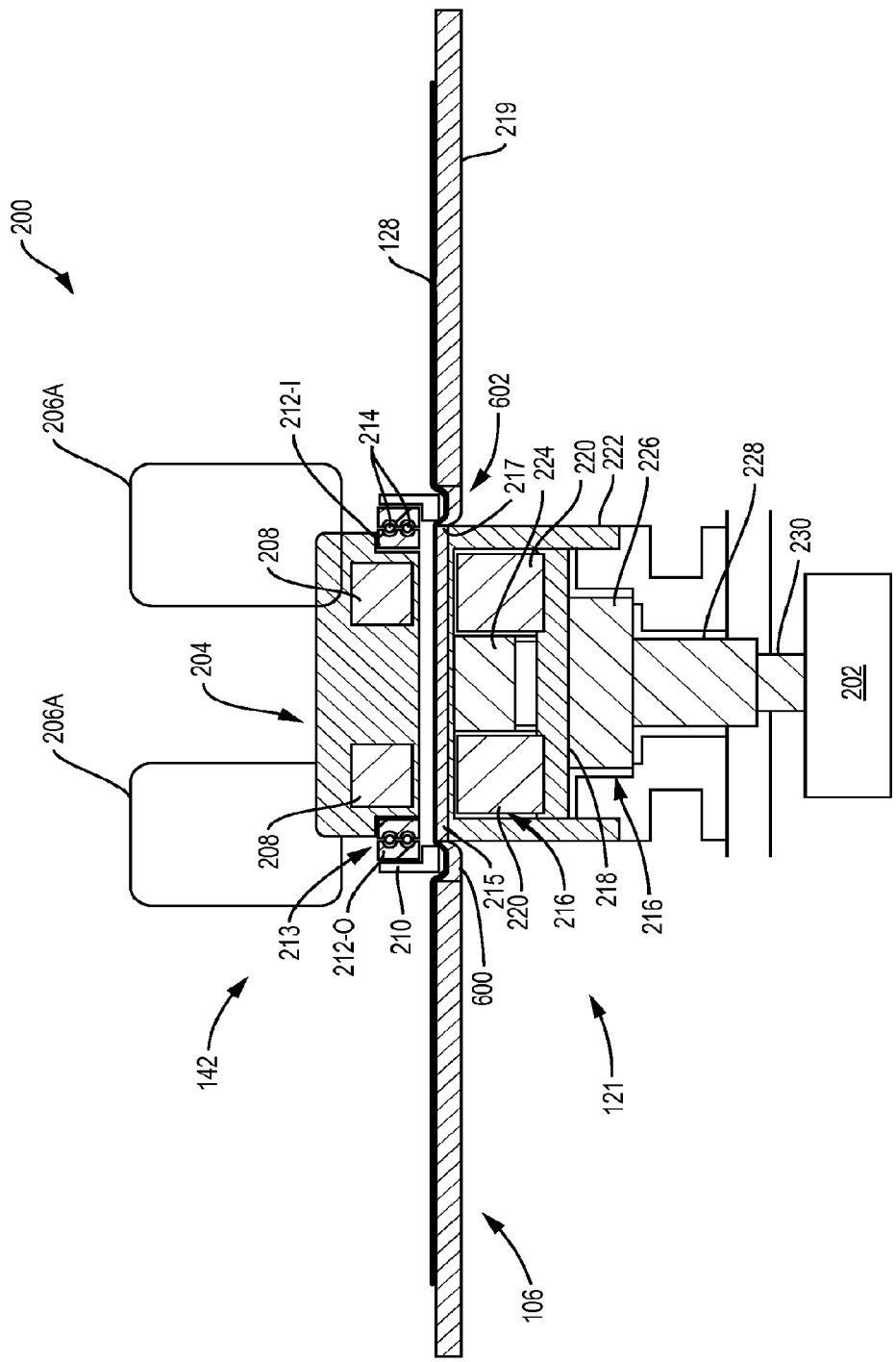
FIG. 6 is a schematic cross-sectional, elevational view of an agitation system including an annular bag support structure wall groove to which the flexible bag may conform, the annular bag support structure wall groove surrounding and positioning the agitator according to an embodiment of the invention.

FIG. 6 shows a magnetic agitator 142 that is similar to that shown in FIGS. 2 and 5. However, in this embodiment the magnetic agitator 142 with agitator bearing structure 213 and the supporting structure 210, which may be in the form of a boot, in contact with an inside surface of flexible bag 128, fits within a bag support structure wall annular groove 600 which, as viewed from above, has a circular shape formed into the bottom plate 219 of the bag support structure wall 106. Also in this way, the flexible bag can be sandwiched between the magnetic agitator 142 and the bag support structure 104. This annular groove 600 is shaped to receive the entire bottom surface of boot 210, that holds the outer bearing race 212-O of the agitator bearing structure 213, and the flexible bag 128 having an inside surface that is in contact with the boot. In particular, the groove 600 enables the flexible bag 128 to collapse inward slightly, conforming to the shape of the annular groove 600 so that the boot (supporting structure) 210 can be engaged with the shaped portion and fits within a formed groove section 602 over the surface of the flexible bag 128, the flexible bag 128 being sandwiched between the bottom, side, or top plate 219 of the bag support structure wall 104 and the boot 210 and the agitator hub 204.

Groove 600 may be formed in the bottom, top, or side plate 219 of the bag support structure wall 106 in order to retain the magnetic agitator 142 in a pre-determined position on the inner surface of the flexible bag 128. This arrangement stabilizes the agitation system 200 during the mixing process and prevents it from moving away from its intended aligned location. Again, it should be noted that there is no rigid portion of the flexible bag 128 for receiving and holding the agitator 142. Further, there is no receiver attached or otherwise secured to the flexible bag for receiving and holding the agitator 142. Therefore, the disclosed invention provides a system comprising a receiver-less flexible bag 128 with an agitator 142 that can be positioned and held at various locations within the bag. The groove 600 also allows for positioning or holding of the flexible bag 128 within the bag support structure 104. Other groove shapes can be formed in the bottom, side, or top plate 219 of the bag support structure wall 106 while serving the overall objective.

Figure 7:
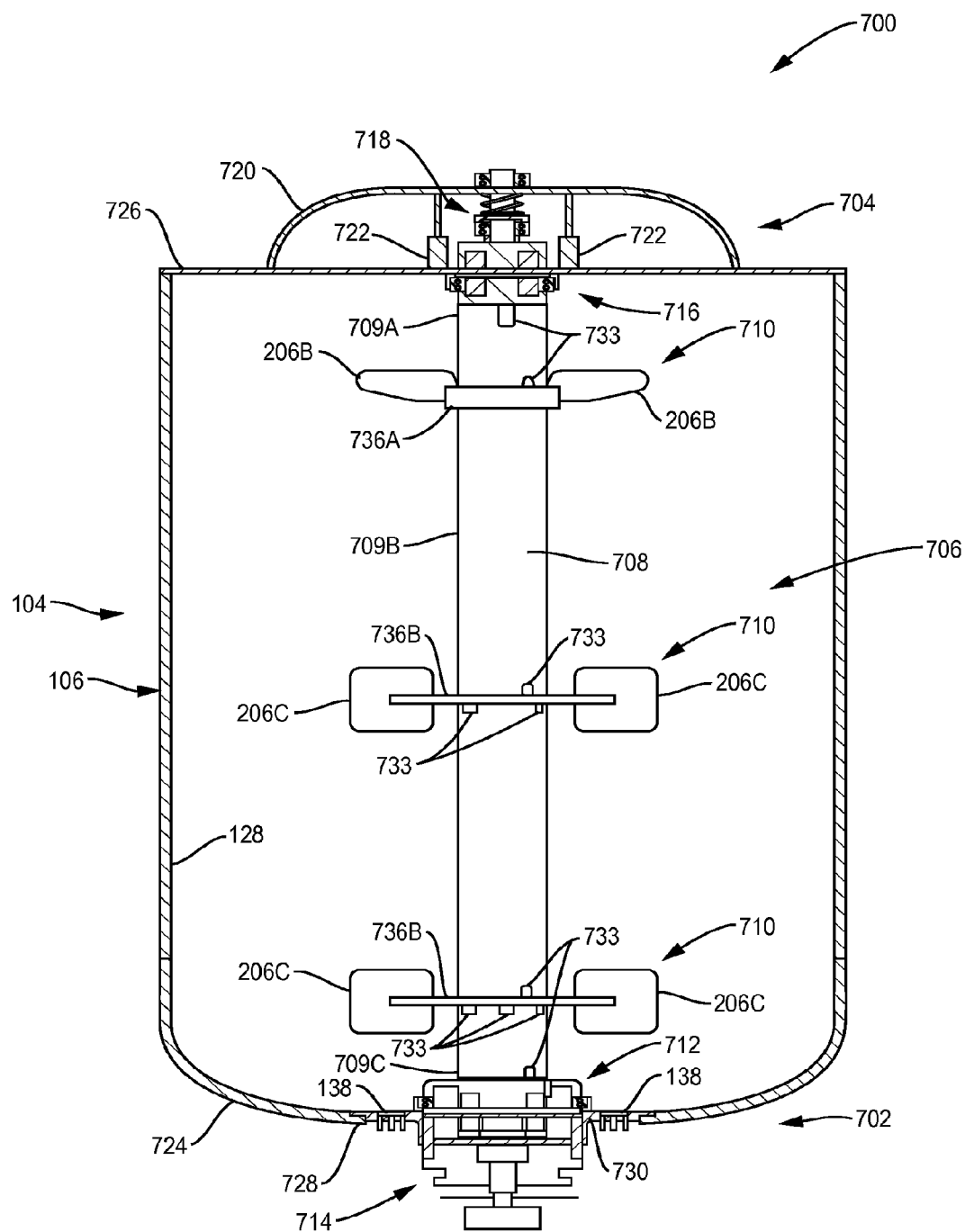
FIG. 7 is a schematic cross-sectional, elevational view of an agitation and support system including an upper and lower magnetic stabilizer for magnetically supporting the agitator within the bag support structure and flexible bag according to an embodiment of the invention.

FIG. 7 depicts a mixing system, that may be a bioreactor, according to an embodiment of the invention and shows an agitation and support system 700 that has been constructed according to the principles of the present invention. The bioreactor includes spargers 138 that fit within the bulkhead unit apertures of the insert 730. In a simple form, a bioreactor according to an embodiment of the invention is almost identical to a mixer according to an embodiment of the invention, except that a bioreactor preferably has at least one sparger 138 for inlet of air or oxygen gas, or a mix of gases, the sparger 138 generally being positioned nearby and/or beneath the impeller blades 710.

The agitation and support system 700 comprises an external lower magnetic stabilizer 702 and an upper magnetic stabilizer 704, for magnetically supporting an agitator 706 within the bag support structure 104 and flexible bag 128, which has an upper portion and a lower portion. The agitator 706 is attached between the upper magnetic stabilizer 704 at the top of the bag support structure 104 and the lower magnetic stabilizer 702 at the bottom of the bag support structure 104.

The agitator 706 includes an agitator shaft 708 and at least one rotatable impeller attached to the agitator shaft. Preferably, there are three impellers 710 attached along the length of the shaft 708. The lower magnetic stabilizer 702 includes a first core magnetic support 712 within the flexible bag 128 and a first magnetic drive system 714 external to the bag support structure 104 and flexible bag 128. The upper magnetic stabilizer 704 may include a second core magnetic support 716 within the flexible bag 128 and a magnetic coupling 718 external to the bag support structure 104 and flexible bag 128. The upper magnetic stabilizer 704 may also include a support bracket 720 and block supports 722 for attaching the magnetic coupling 718 to the bag support structure 104 providing the magnetic coupling 718 with additional support. In another embodiment of the invention (not shown), the upper magnetic stabilizer 704 could include an upper magnetic drive, and the upper, or second core magnetic support 716 could include an additional agitator.

The agitator 706 as well as the first and second core magnetic supports 716/712 are located within the flexible bag 128, which is preferably a bag as described above. In one embodiment of the inventive device, the flexible bag 128 fits tightly along the inner surface of the bag support structure wall 106. The bag support structure wall 106 includes a bottom section 724 that forms the bottom of the bag support structure 104 and a top plate 726 that forms the top of the bag support structure 104. The bag support structure wall 106 has a stabilizer port 728 or aperture formed in the center of the bottom section 724, and in the top section 104. Also shown in FIG. 7 is a disc-shaped insert 730 is fit within the stabilizer port 728.

Figure 8:
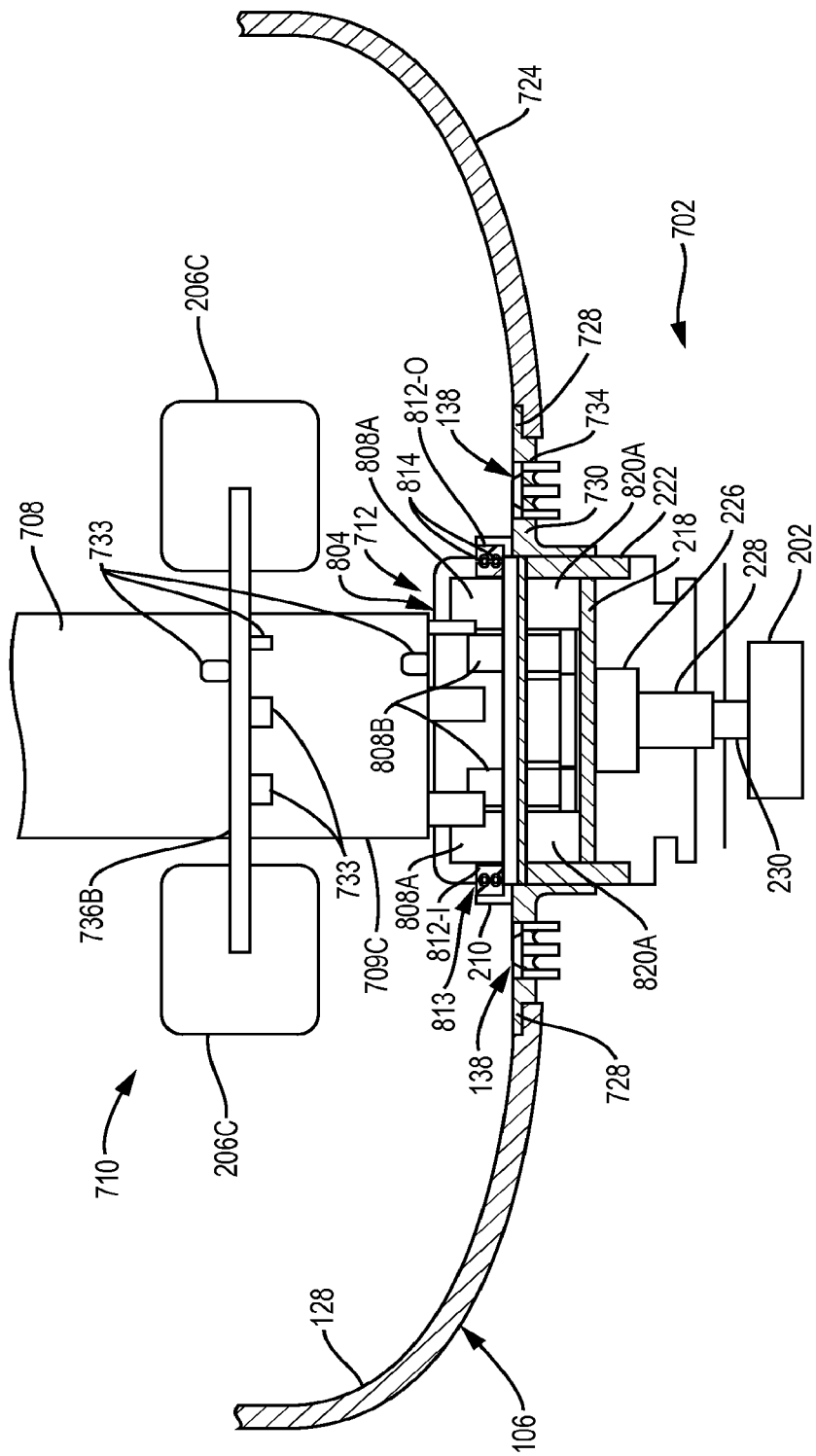
FIG. 8 is a schematic cross-sectional, elevational view of the lower magnetic stabilizer from FIG. 7 according to an embodiment of the invention.

As shown in the bioreactor of FIG. 8, this disc-shaped insert 730 preferably includes a drive system slot 732 on one face of the insert and two or more bulkhead unit apertures 734 along the perimeter of the drive system slot 732. The magnetic drive system 714 is located external to the bag support structure 106 and fits within the drive system slot 732 of the disc-shaped insert 730. The bottom section 724 of the bag support structure wall 106 forms a curved profile for supporting the insert 730 and the lower magnetic stabilizer 702 in place along the edge of the stabilizer port 728. The flat top and bottom surface of the disc-shaped insert 730 provides an even planar interface for the external magnetic drive system 714 and the first core magnetic support 712. Spargers 138 fit within the bulkhead unit apertures 734 of the insert 730. Alternatively, the bulkhead unit apertures 734 are used for supporting units for keeping the insert in place or sensor units for measuring a gas composition.

As shown in FIG. 8, the agitator 710 has an agitator shaft 708 with slots 733 at different intervals along the length of the shaft 708 for allowing attachment of each impeller 206, 736 to the shaft 708 as well as attachment of the agitator shaft 708 to the upper magnetic stabilizer 704 (as in FIG. 7) and first core magnetic support 712. Turning back to FIG. 7, the agitator shaft 708 may have an upper end 709A, a middle section 709B, and a lower end 709C. The upper end 709A of the agitator shaft 708 attaches to the upper magnetic stabilizer 704. The impellers 710 attach to the middle section 709B of the agitator shaft 708. The lower end of the agitator shaft 709C is where the shaft 709C attaches to the first core magnetic support 712.

The agitator 706 preferably includes impellers 710 each having at least two vanes/blades (206B or 206C) that are connected to one other by an arm 736A/736B. The vanes/blades 206B/206C have grooves or slots for fitting into the arms 736A/736B or alternatively the vanes 206B/206C attach to the arms 736A/736B via pins (not shown). Each arm 736A/736B attaches to a first vane/blade 206B/206C at one end of the arm 736A/736B and to a second vane/blade 206B/206C at an opposite end of the arm 736A/736B so that the impeller 710 with the vanes/blades 206B/206C spinning on the outside.

The arms 736A/736B of each impeller 710 may have tab portions (not shown) that are shaped to fit within the shaft slots 733 allowing attachment between the arms 736A/736B of the impeller 710 and the agitator shaft 708. Each arm 736A/736B rotates in conjunction with the rotation of the agitator shaft 708 along the points of attachment. This enables mixing and agitation of a substance due to the agitator shaft 708 transferring its rotation to the impellers 710.

As shown in FIG. 7, there are three impellers 710 attached along the agitator shaft 708. The middle impeller and lower impeller include vanes/blades 206C having a rectangular-like shape similar to the paddle-like vanes/blades 206A described above. These vanes/blades 206C are attached to a thin or narrow arm 736B for attaching to the agitator shaft 708. The upper impeller may include a thin wing-shaped set of vanes/blades 206B as shown in FIG. 3A and described above. These vanes/blades 206B have a thicker arm 736A for attaching the vanes 206B to the agitator shaft 708.

FIG. 8 shows a cross-sectional view of the first core magnetic support 712 shown in FIG. 7. The lower magnetic stabilizer 702 includes the first core magnetic support 712 and the magnetic drive system 714. The first core magnetic support 712 is positioned at the bottom of the bag support structure 104 within the flexible bag 128. The magnetic drive system 714 is positioned within the drive system slot 732 in order to magnetically couple with the first core magnetic support 712. The magnetic flux between the magnetic drive system 714 and the first core magnetic support 712 causes rotation of first core magnetic support 712 when the magnetic drive system 714 is in use.

The first core magnetic support 712 may include agitator hub 804 including at least one magnet. The lower end 709C of the agitator shaft 708 attaches to the top of the agitator hub 804 enabling the agitator shaft 708 to rotate in conjunction with the rotation of the agitator hub 804. Similar to the arms 736A/736B, the agitator hub 804 includes slots or tabs on its top surface for attaching directly to the shaft slots 733 at the bottom end of the agitator shaft 708 (not shown).

The first core magnetic support 712 may include a lower core bearing structure 813 for supporting the agitator hub 804 above the insert 730 and the flexible bag 128 while allowing the agitator hub 804 to rotate around its central axis. The lower core bearing structure 813 has the same configuration as the agitator bearing structure 213 (shown in FIG. 6), except that it is used for supporting the agitator hub 804 versus the agitator hub 204. This lower core bearing structure 813 may be a bearing assembly including an inner bearing race 812-I coupled to an outer bearing race 812-O via double ball bearings 814 as described above. Similar to the agitator hub 204, the inner bearing race 812-I is attached to the lower perimeter of the agitator hub 804 specifically sitting in a recess formed in the bottom outer edge of the agitator hub 804. The lower core bearing structure 813 fits within boot (supporting structure) 210 as shown in FIG. 8 and described above.

The main difference between the agitator hub 804 design and the agitator hub 204 design is that outer core magnets 808A and inner core magnets 808B may be included in the agitator hub 804. These magnets are similar to the hub magnets 208 described above except that the outer core magnets 808A are larger is size as compared to the smaller inner core magnets 808B. Having a smaller set of inner core magnets 808B surrounded by larger outer core magnets 808A produces a sufficient amount of magnetic flux to control both rotation of the agitator 706 along with stabilizing the agitator 706 along the length of the bag support structure 104. Similar to hub magnets 208, magnets 808A and 808B are sent into voids that are either molded or machined into the body of the agitator hub 804 and oriented such that the magnetic field is directed along the vertical axis of the agitator hub 804 for compatible attraction with the magnetic drive system 714. Preferably, the agitator hub 804 includes more than two outer core magnets 808A and more than two inner core magnets 808B that surround the center of the agitator hub 804, forming an array of magnets. The number of magnets is determined based on the desired magnetic flux needed and also the physical size constraints of the agitator hub 804. The outer core magnets 808A and inner core magnets 808B are preferably high performance rare earth magnets.

The magnetic drive system 714 can control rotation of the first core magnetic support 712 that translates the rotation to the agitator shaft 708 of the agitator 706 causing agitation of a substance within the bag 128. The magnetic drive system 714 may include essentially the same components as the magnetic drive system 121 connected in the same configuration as described above.

The main difference between magnetic drive system 714 and magnetic drive system 121 is the magnet configuration. Magnetic drive system 714 includes a set of outer drive magnets 808A larger in size as compared with the smaller inner drive magnets 808B. These outer and inner drive magnets 808A/808B are installed within either molded or machined recesses that are formed into the drive head 216 similar to drive magnets 220. This magnetic configuration enables a strong magnetic flux between the core magnetic drive system 714 external to the bag support structure 104 and the first core magnetic support 712 within the bag support structure 104 and flexible bag 128 forming a strong coupling.

Figure 9:
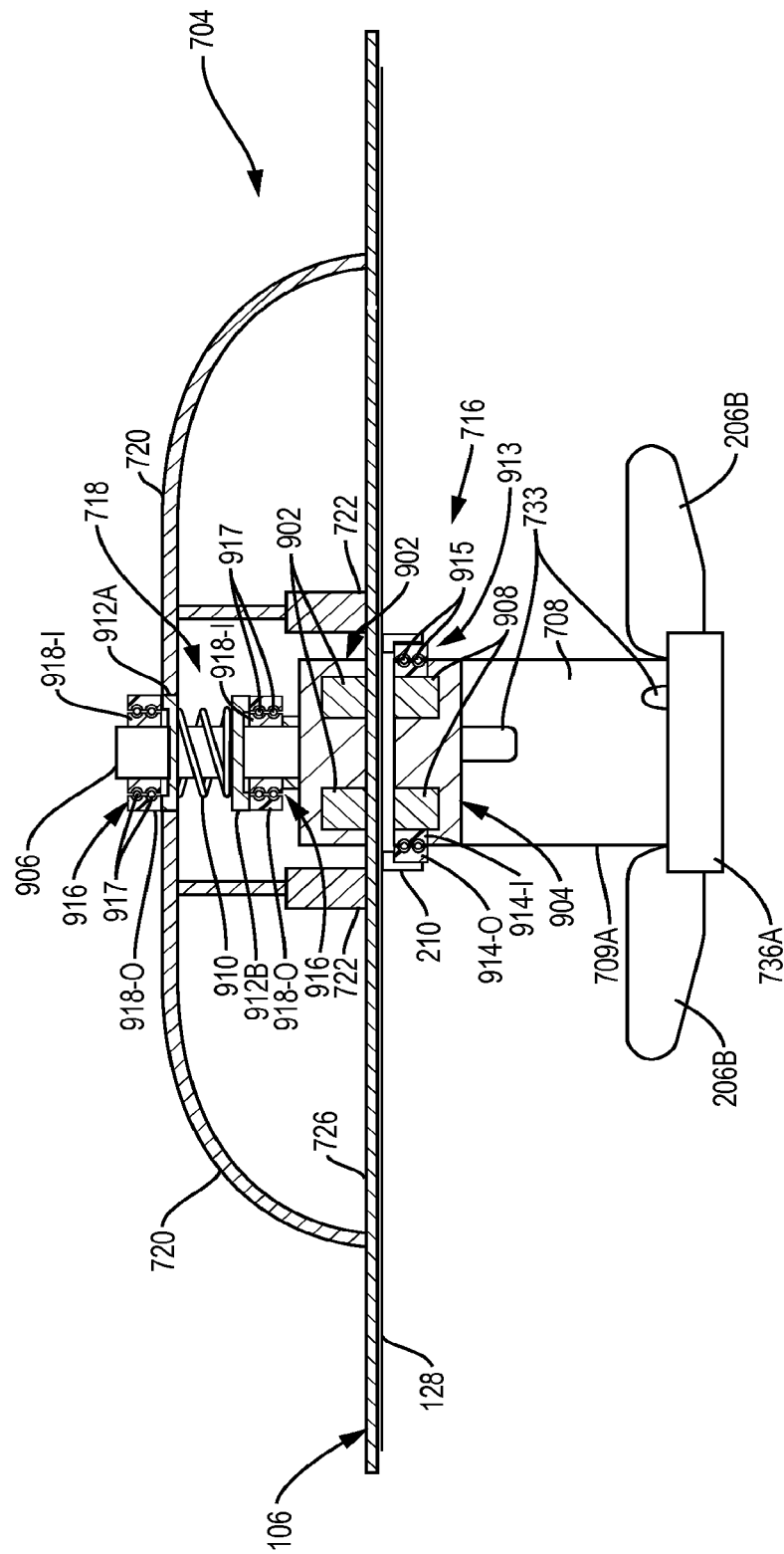
FIG. 9 is a schematic cross-sectional, elevational view of the upper magnetic stabilizer from FIG. 7 according to an embodiment of the invention.

FIG. 9 shows a cross-sectional view of the upper magnetic stabilizer 704 shown in FIG. 7. The function of the upper magnetic stabilizer 704 is to provide further support to the agitator 706 from the top of the bag support structure 104 without requiring attachment to or through the top plate 726 of the bag support structure wall 106. The upper magnetic stabilizer 704 may include the second core magnetic support 716 and the magnetic coupling 718. The second core magnetic support 716 is preferably positioned at the top of the bag support structure 104 along the top inner surface of the flexible bag 128. The magnetic coupling 718 is positioned against the external surface of the top plate 726 in order to magnetically couple with the second core magnetic support 716. The upper end 709A of the agitator shaft 708 attaches to the bottom of the second core magnetic support 716. Thus, as the agitator shaft 708 rotates the second core magnetic support 716, magnetic flux causes rotation of the magnetic coupling 718 along the surface of the top plate 726.

The second core magnetic support 716 may include a second core magnetic base 904 having a similar design as compared to the first core magnetic base 804 and the agitator hub 204 described above. Similar to the first core magnetic base 804, the second core magnetic base 904 includes slots or tabs on its bottom surface for attaching directly to the shaft slots 733 at the upper end 709A of the agitator shaft 708 (not shown).

As shown in the FIG. 9, the second core magnetic base 904 may be attached to an upper core bearing structure 913 allowing the second core magnetic base 904 to easily rotate within the flexible bag 128 along the top plate 726 of the bag support structure wall 106. The upper core bearing structure 913 has the same configuration as the agitator bearing structure 213 and the lower core bearing structure 813 except that it is used for supporting the second core magnetic base 904 along a top surface of the flexible bag 128. The upper core bearing structure 913 is a bearing assembly including an inner bearing race 914-I coupled to an outer bearing race 914-O via double ball bearings 915. Similar to the lower core bearing structure 813, the inner bearing race 914-I is attached to the upper perimeter of the second core magnetic base 904 specifically sitting in a recess formed in the top outer edge of the second core magnetic base 904. The upper core bearing structure 913 fits within boot 210 for maintaining stability and to prevent the agitator shaft 708 and second core magnetic base 904 from walking during rotation. The upper core bearing structure 913 is adapted to engage a portion of a bag support structure 106 or a lid.

The second core magnetic support 716 may also include second core magnets 908 within the second core magnetic base 904. These second core magnets 908 are rare earth magnets similar to the hub magnets 208 described above. The second core magnets 908 are sent into voids that are either molded or machined into the body of the second core magnetic base 904 and oriented such that the magnetic field is directed along the vertical axis of the base 904 for compatible attraction with the magnetic coupling 718.

The magnetic coupling 718 may include a coupling base 900 having a similar design as compared to the second core magnetic base 904. The coupling base 900 has a circular shape when looking down upon the coupling base 900 from the top of the bag support structure 104. The coupling base 900 sits along a central external surface of the top plate 726.

The coupling base 900 may include coupling magnets 902 that are rare earth magnets similar to the second core magnets 908 and hub magnets 208. The coupling magnets 902 are sent into voids that are either molded or machined into the body of the coupling base 900 and oriented such that the magnetic field is directed along the vertical axis of the coupling base 900 for compatible attraction with the second core magnetic support 716.

The magnetic coupling 718 may also include a supporting shaft 906 centrally attached to the top surface of the coupling base 900 within a connection piece 915. Connection piece 915 is a short tubular structure that attaches to a top central surface of the coupling base 900. The supporting shaft 906 fits tightly into connection piece 915 to provide a strong attachment to the coupling base 900.

Two sets of shaft bearing structures 916 may be attached along the perimeter of the supporting shaft 906. As shown in FIG. 9, one shaft bearing structure 916 is attached to an upper portion of the supporting shaft 906 and another shaft bearing structure 916 is attached to a lower portion of the shaft 906 so that the supporting shaft 906 can easily rotate along a central vertical axis.

These shaft bearing structures 916 may have the same configuration as the agitator bearing structure 213, the lower core bearing structure 813, and the upper core bearing structure 913 except that shaft bearing structure 916 is used for stabilizing the supporting shaft 906 in its rotation at two different positions. Each shaft bearing structure 916 includes an inner bearing race 918-I coupled with the outer bearing race 918-O via a double ball bearing 917. The inner bearing races 918-I for both shaft bearing structures 916 are attached to a recess formed in the outer wall of the supporting shaft 906 (not shown).

The magnetic coupling 718 may also include a spring 910 that surrounds a middle section of supporting shaft 906. This spring 910 has an elastic property hampering strong vertical forces while also allowing adjustability of the magnetic coupling 718 during rotation.

The magnetic coupling 718 may also include an upper short bracket 912A and a lower short bracket 912B attaching to and fit around the supporting shaft 906. These short brackets 912A/912B are positioned between shaft bearing structures 916 and spring 910. The short brackets 912A/912B are positioned directly against shaft bearing structures 916 on a flat side and the spring 910 along an opposite bracketed side as viewed from a cross-section. This arrangement of the shaft bearing structures 916, spring 910, and short brackets 912A/912B along supporting shaft 906 provides further stability to the coupling base 900 as it rotates in conjunction with its magnetic coupling to the second core magnetic support 716.

The upper magnetic stabilizer 704 also includes supporting bracket 720. Short bracket 912A is positioned along the supporting shaft 906 at a position to attach to the supporting bracket 720. A central section of the supporting bracket 720 attaches to the short bracket 912A that connects to the supporting shaft 906. Supporting bracket 720 bridges the magnetic coupling 718 to the top plate 726 of the bag support structure wall 106. The supporting bracket 720 forms an arc over the center of the top plate 726 of the bag support structure wall 106. The supporting bracket 720 attaches to the top plate 726 at both ends of the arc. Supporting bracket 720 also includes at least two columns attached to at least two block supports 722. The block supports 722 attach to the top plate 726 at an outer perimeter of the coupling base 900 providing further stability for the magnetic coupling 718.

Figure 10:
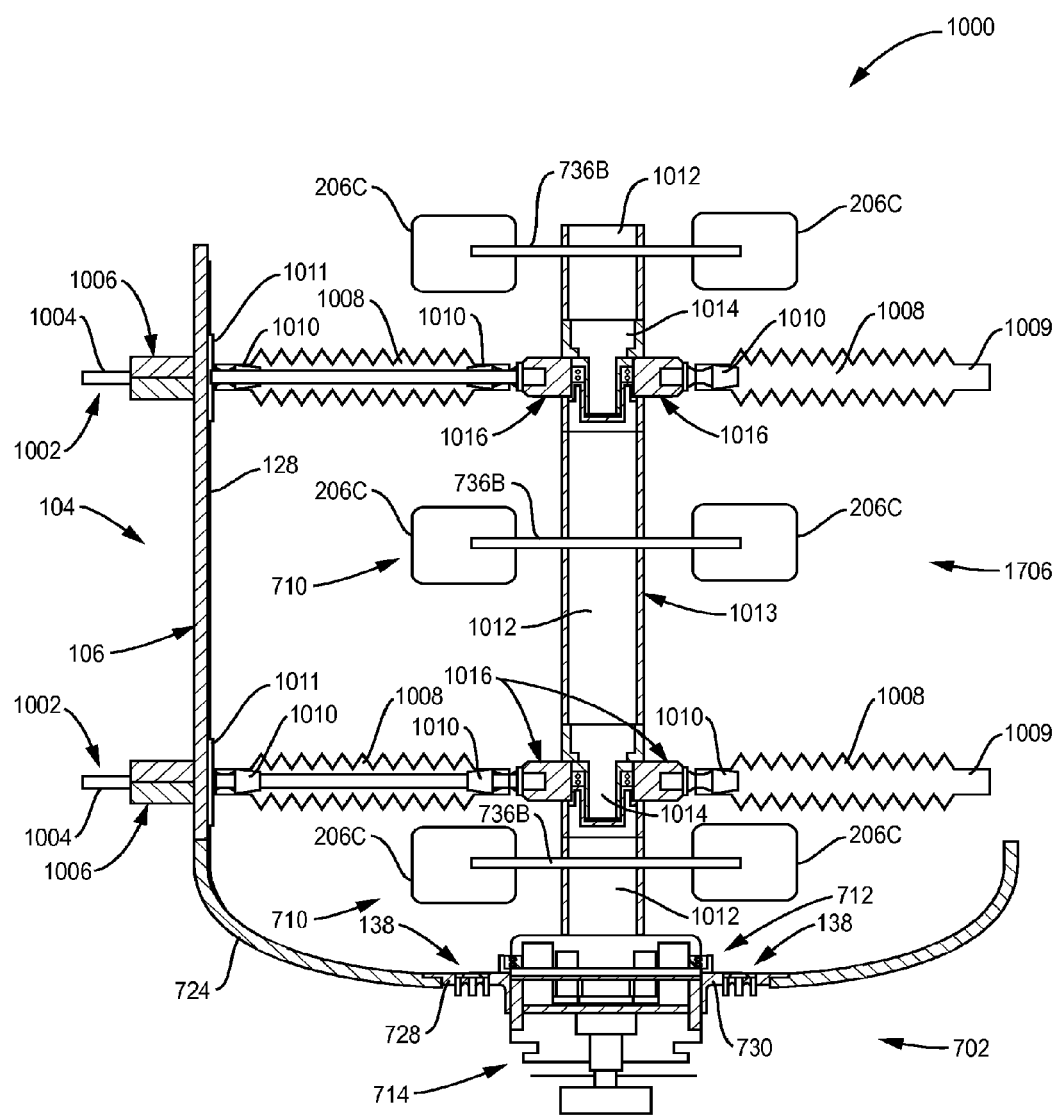
FIG. 10 is a schematic cross-sectional, elevational view of an agitation and agitator support system including bag support structure wall stabilizers for stabilizing the agitator within the bag support structure and flexible bag in a mixer or a bioreactor according to an embodiment of the invention.

FIG. 10 shows an alternative mixing system embodiment. This mixing system includes an agitation and support system 1000 that has been constructed according to the principles of the present invention.

System 1000 comprises an agitator assembly 1706, a lower magnetic stabilizer 702, and bag support structure wall stabilizers 1002 for supporting the agitator assembly 1706 within the bag support structure 104 and flexible bag 128. The agitator assembly 1706 is attached to the lower magnetic stabilizer 702 at the bottom of the bag support structure 104.

The agitator assembly 1706 includes an agitator shaft 1013, that is preferably a segmented shaft and at least one impeller 710 attached along the length of the segmented shaft 1013. The lower magnetic stabilizer 701 includes the first core magnetic support 712, positioned within bag 128, and core magnetic drive system 714, positioned within an insert 730 described above with regard to FIGS. 7 and 8. Each bag support structure wall stabilizer 1002 is attached to the side of the bag support structure 104 at one end and the segmented shaft 1013 at an opposite end. There is at least one stabilizer 1002 that is configured to provide a linkage between the agitator shaft 1013 and the support structure 104.

The agitator assembly 1706 includes a segmented shaft 1013 having main shaft segments 1012 attached between mating shaft segments 1014 forming an entire segmented shaft 1013 from the top to the bottom of the bag support structure 104.

The agitator assembly 1706 has the same impeller design as described in FIGS. 7-9. The agitator 1706 includes impeller 710 having two blades/vanes 206C attached to each other by arm 736B. Arm 736B attaches to the segmented shaft 1013 at a position along the main sections 1012 enabling the impeller 710 to rotate in conjunction with the segmented shaft 1013 along the axis of this attachment.

The lower magnetic stabilizer 702 functions to magnetically drive the rotation of the agitator assembly 1706 along with supporting the agitator assembly 1706 in use as described above with regard to FIGS. 7 and 8. The lower magnetic stabilizer 702 includes the first core magnetic support 712 and the magnetic drive system 714. The magnetic flux between the magnetic drive system 714 and the first core magnetic support 712 causes rotation of the first core magnetic support 712 when the magnetic drive system 714 is in use. The bottom main shaft segment 1012 of the segmented shaft 1013 is attached to the top of the first core magnetic support 712. Thus, the rotation of the first core magnetic support 712 from the running of the magnetic drive system 714 causes rotation of the segmented shaft 1013 thus enabling agitation by the rotating agitator assembly 1706.

At different intervals along the segmented shaft 1013, preferably at least two bag support structure wall stabilizers 1002 are attached from the bag support structure wall 106 to the segmented shaft 1013 at the same mating shaft segment 1014 for balancing support of the segmented shaft 1013 on both sides of the bag support structure 104. Preferably, there are a plurality of stabilizers 1002 deployed in radial orientations in order to link the agitator shaft 1013 to different portions of a side wall of the support structure 106.

Each bag support structure wall stabilizer 1002 includes a rod 1004 having a first end and a second end. The rod 1004 forms the main support and core structure for the bag support structure wall stabilizer 1002. The first end of the rod 1004 is configured for attachment to a portion of the bag support structure 104 surrounding the flexible bag and the second end is configured for attachment to the agitator shaft 1013. The first end of the rod may be attached to a side portion or to the top portion of the support structure 104. The top portion may be an integral element of the support structure 104 or a bracket or a lid associated with the support structure. The rod 1004 may stretch perpendicularly to the bag support structure 104 through the bag support structure wall 106 to an attachment section on the segmented shaft 1013. These rods 1004 may be formed, for example, from plastic, or alternatively metal. The rods useful in the wall stabilizers (as well as top stabilizers that are also disclosed herein) are preferably rigid. As used herein, the term "rigid" refers to a structure that does not bend easily or is less flexible than a structure that is described as "flexible," and is intended to encompass rigid and semi-rigid, solid, hollow or composite structures of various geometric shapes, e.g., cylindrical, tubular or tapered shapes. A rigid rod can be somewhat flexible and, in some applications, the ability to flex to some extent may be desirable. The key requirement of any rigid rod is simply that it has sufficient mechanical integrity to constrain off-centric movements of the impeller or agitator shaft.

The bag support structure wall stabilizer 1002 may also include pinch blocks 1006 that attach a distal end section of the rod 1004 to the outer surface of the bag support structure wall 106. In another example, the rod 1004 is welded or permanently connected to the outer surface of the bag support structure wall 106 where the pinch blocks 1006 fit.

Figure 11:
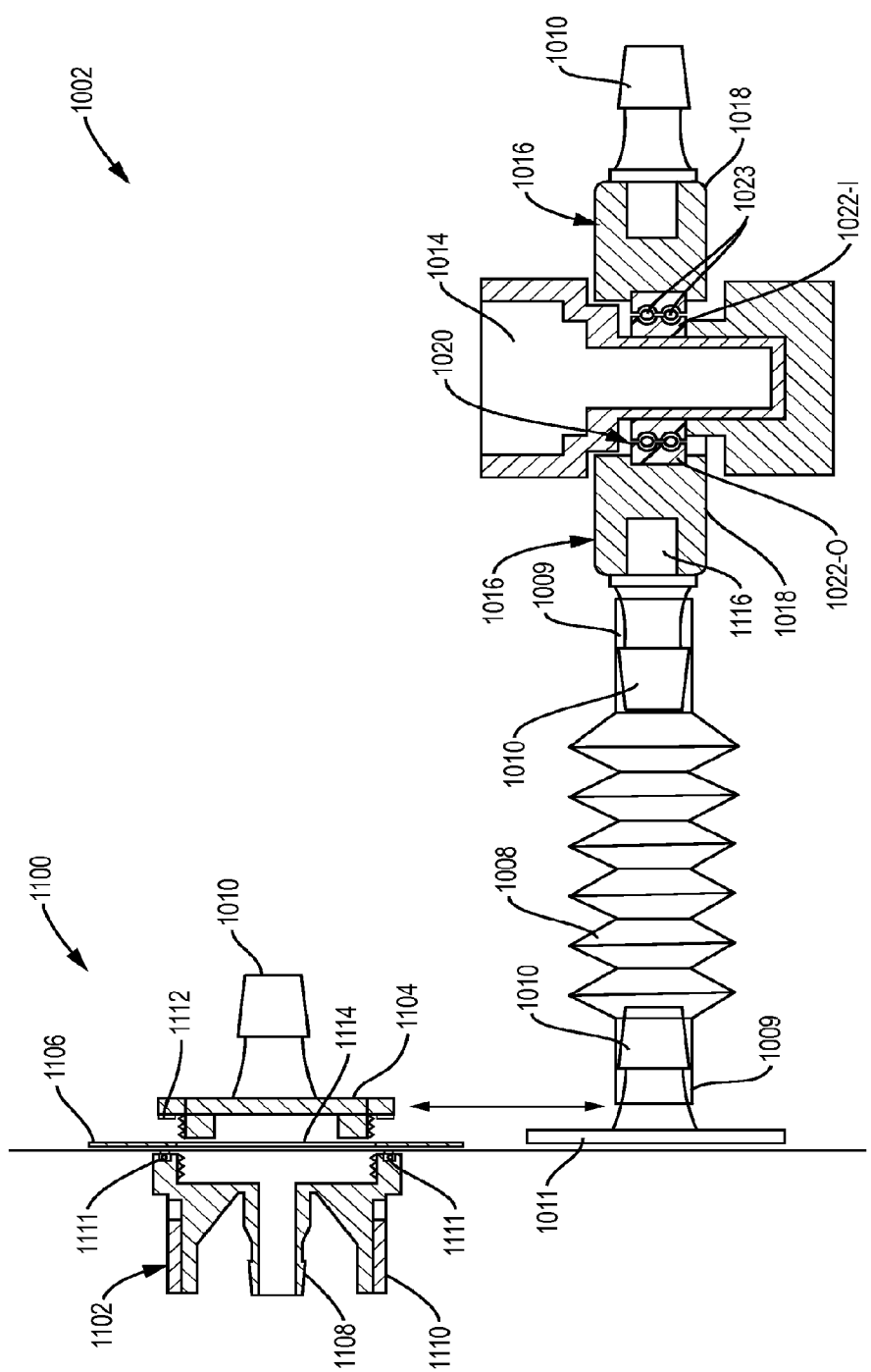
FIG. 11 is a schematic cross-sectional view of one of the bag support structure wall stabilizers from FIG. 10 according to an embodiment of the invention.

As further shown in FIGS. 10 and 11, the bag support structure wall stabilizer 1002 can also include a bearing block assembly 1016 connecting the second end of the rod 1004 to a portion of the agitator shaft 1013. The proximal end of the rod 1004 attaches to the bearing block assembly 1016. The bearing block assembly 1016 attaches directly to the mating shaft segment 1014 of the segmented shaft 1013.

The bag support structure wall stabilizer 1002 also includes a flexible tube 1008. The portion of the rod 1004 within the bag support structure 104 and flexible bag 128 is surrounded by the flexible tube 1008. The tube surrounds the rod 1004 so that it can pass through the flexible bag without contacting fluid therein pass through the flexible bag without contacting fluid therein. The flexible tube 1008 includes tube fittings 1009 at both ends of the flexible tube 1008 for attaching to a barb fitting 1010 on the bag support structure wall 106 at one end and a barb fitting 1010 on the bearing block assembly 1016 at the other end. The flexible tube 1008 fits around rod 1004 and includes bellows along the length of the flexible tube 1008 to provide needed flexibility to the bag support structure wall stabilizer 1002. These flexible tubes are preferably made from a plastic or polymeric material for example.

The bag support structure wall stabilizer 1002 also includes a port plate 1011 that is attached or permanently welded to the inner surface of the bag support structure wall 106. The port plate 1011 includes a central opening for allowing the rod 1004 to fit through the bag support structure wall 106 into the bag support structure 104 and flexible bag 128. The port plate 1011 also includes the central barb fitting 1010 for allowing attachment to the tube fitting 1009 of the flexible tube 1008. The port plate 1011 provides a secure attachment for the flexible tube 1008 and rod 1004 to the bag support structure wall 106.

FIG. 10 also shows bulkhead units 138.

FIG. 11 shows a cross-sectional view of one of the bag support structure wall stabilizers 1002 shown in FIG. 10. The bag support structure wall stabilizer 1002 may be attached to the bag support structure wall 106 by means of a port plate 1011 or alternatively a bulkhead unit 1100 each of which is fitted with a barb fitting 1010 for connecting to the flexible tube 1008. This results in an open pathway for fitting the rod 1004 from outside of the bag support structure 104 thru the bag support structure wall 106 and flexible bag 128 internally to the bearing block assembly 1016.

The bulkhead unit 1100 may be a threaded bulkhead fitting that fits within the bag support structure wall 106 as shown in FIG. 10 for attaching the flexible tube 1008 to the bag support structure wall 106 along with providing a pathway for the rod 1004 through the bag support structure wall 106. The bulkhead unit 1100 may comprise three parts including a barbed fastener 1102 (lower section), a spacer 1106 (middle section), and a bulkhead base (upper section) combined together to form the bulkhead unit 1100.

The bulkhead unit 1100 may include a barbed fastener 1102 that fits within the bag support structure wall 106 and flexible bag 128 external to the bag support structure 104. The barbed fastener 1102 includes a barbed central section 1108 for allowing insertion of the rod 1004 and for attaching to external supports if necessary. The fastener 1102 also includes a protective tab 1110 for protecting the barbed section 1108. Fastener 1102 further includes a fastener gasket 1111 surrounding an upper portion of the fastener 1102 to maintain sealing of the fastener 1102.

The bulkhead unit 1100 may also include a bulkhead base 1104 that fits within the bag support structure wall 106 and flexible bag 128 from within the bag support structure 104. The bulkhead base 1104 includes the barb fitting 1010 for allowing attachment to the flexible tube 1008. The bulkhead base 1104 also includes a base gasket 1112 for sealing the base 1104 against the barbed fastener when attached.

As further shown in FIG. 11, the bulkhead base 1104 may include outer screw grooves and the barbed fastener 1102 includes inner screw grooves for allowing the bulkhead base 1104 to screw into the barbed fastener 1102. The bulkhead unit 1100 also includes a spacer 1106 such as a washer that is positioned between the bulkhead base 1104 and the barbed fastener 1102. The bulkhead base 1104 fits within a passage 1114 in the spacer 1106 and the inner screw grooved section of the barbed fastener 1102 to form a tightened fit with the outer grooved section of the barbed fastener 1102.

The flexible tube 1008 may attach between the bulkhead unit 1100 barb fitting 1010 or port plate 1011 barb fitting 1010 at the bag support structure wall 106 end and the bearing block assembly 1016 at the segmented shaft 1013 end.

The bearing block assembly 1016 may include a barb fitting 1010 for allowing attachment to the flexible tube 1008 at the tube fitting 1009. This barb fitting 1010 is attached to a steady bearing block 1018 at section 1116 on the bearing block assembly 1016. The steady bearing block 1018 attaches to the mating shaft segment 1014 of the segmented shaft 1013 via a support bearing 1020.

This support bearing 1020 is similar in configuration to the agitator bearing structure 213 and particularly the shaft bearing structures 916. The support bearing 1020 includes inner and outer races (1022-I and 1022-O) fit between double ball bearings 1023. The ball bearing 1023 could be configured for as a single ball bearing or more than two ball bearings could be also used. The outer race 1022-O attaches to the steady bearing block 1018 and the inner race 1022-I attaches to the mating shaft segment 1014 to form a flexible support structure between the bearing block assembly 1016 and the segmented shaft 1013. This support bearing 1020 configuration allows the mating shaft segment 1014 to rotate with the rest of the segmented shaft 1013 while attached via ball bearings 1023 to the bearing block assemblies 1016, i.e. the support bearing 1020 links the stabilizer to the agitator shaft 1013 while permitting rotation of the shaft relative to the stabilizer. The ball bearings facilitate independent rotation with reduced friction.

Figure 12:
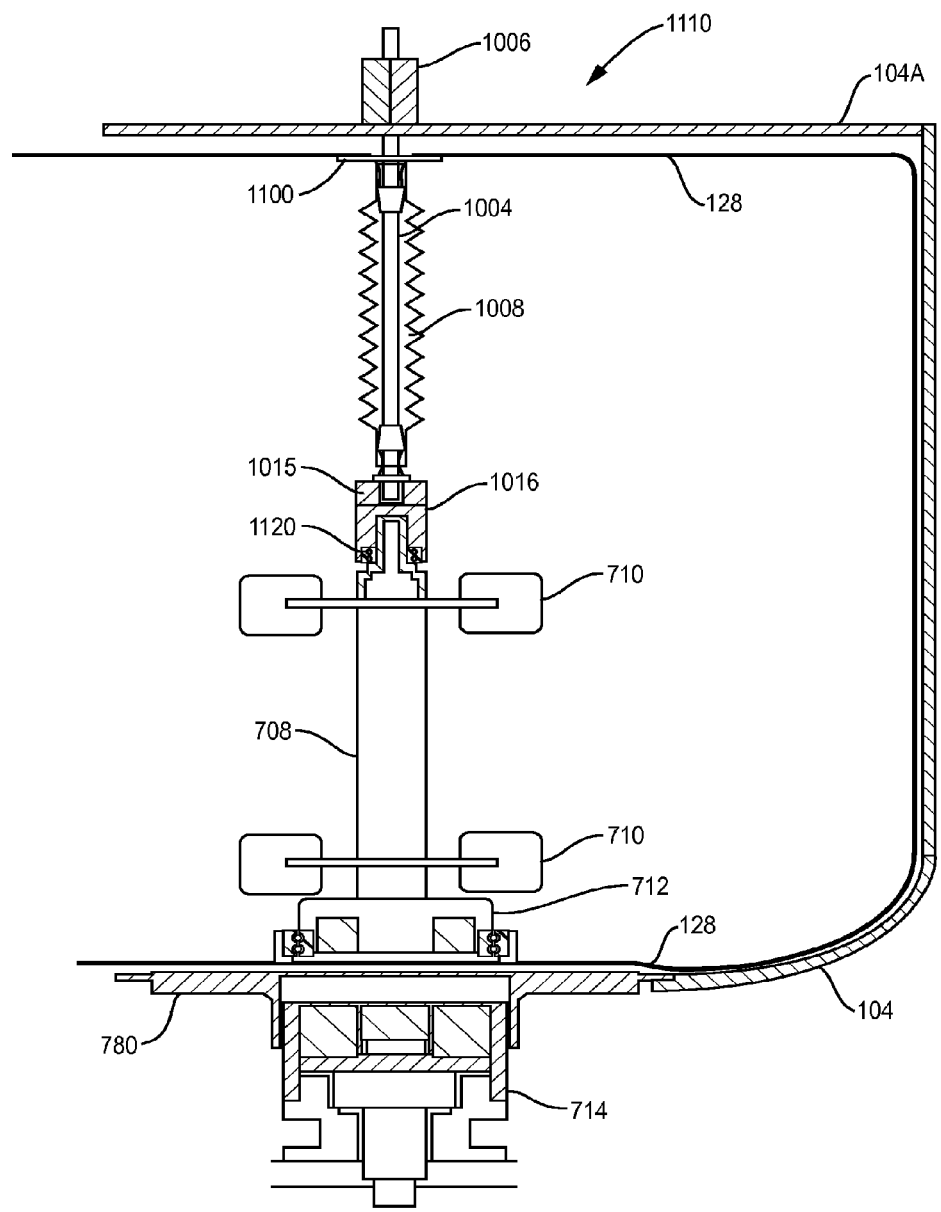
FIG. 12 shows a cross-sectional, elevation view of a top stabilizer for stabilizing the agitator within the bag support structure and flexible bag in a mixer or a bioreactor according to an embodiment of the invention.

FIG. 12 shows a cross-sectional view of a bag support structure top stabilizer 1110. The flexible bag has an upper portion and a lower portion. An agitator 712 is provided for mixing the fluid. The agitator comprises at least one rotatable impeller 710 attached to an agitator shaft 708. The agitator shaft has a lower end and an upper end. At least one stabilizer 1110 is configured to provide a linkage between the upper end of the agitator shaft 708 and a top portion of the support structure 104A. As shown in FIG. 12, the bag support structure top stabilizer 1110 is attached to a top portion of the support structure 104A e.g., a top wall or lid, by means of an anchor element, e.g., port plate or alternatively a bulkhead unit, that includes a fitting 1110, e.g., a barb fitting, for connecting to the flexible tube 1008. The term "top portion of the support structure" as used herein is intended to cover any structure that can serve as an anchor for a vertical support rod or strut, i.e. to which the support structure can be connected, including, but not limited to, an upper segment of a unitary support structure, i.e. the top portion of the support structure is an integral element of the support structure, a bracket extending from a sidewall of a support structure or a lid that engages a support structure. The fitting 1110 provides an open pathway for fitting the rod 1004 from outside of the bag support structure 104 through the top portion of the support structure 104A, the bag 128 and inside flexible tube 1008 to engage a bearing block assembly 1016.

The bearing block assembly 1016 of FIG. 12 can include a bearing block fitting, e.g., another barb fitting, for attachment of the other end of the flexible tube 1008 and a block 1015 for receiving the other end of rod 1004. The bearing block assembly 1016 may further comprise a support bearing 1120 that links the stabilizer 1110 to the upper end of the agitator shaft 708 while permitting rotation of the shaft relative to the stabilizer. This bearing block assembly 1016 is otherwise similar in configuration to the previously described agitator bearing structures and can include a bearing 1120 including a raceway, e.g., inner and outer races fit between double ball bearings. This support bearing configuration allows the mating shaft segment 708 to rotate with its impellers 710 when the external driver 714 is engaged within mount 780 and magnetically coupled to agitator 712.

FIGS. 13-20 illustrate another aspect of the invention, namely, the use of radial or quasi-radial magnetic coupling for improved energy transfer from the external drive magnets to the magnets of the agitator and better control of coupling forces during the coupling and decoupling of the external drive shaft and the agitator. The magnetic agitator is preferably disposable in the flexible bag and configured to rotate about an axis of rotation when magnetically coupled to an external magnetic drive system (121; 714; 1200). The magnetic agitator comprises at least one magnet configured to magnetically couple with a drive magnet of opposite polarity associated with the external magnetic drive system. The coupling between the agitator magnet and the drive magnet occurs in a generally radial direction relative to the axis of rotation.

Figure 13B:
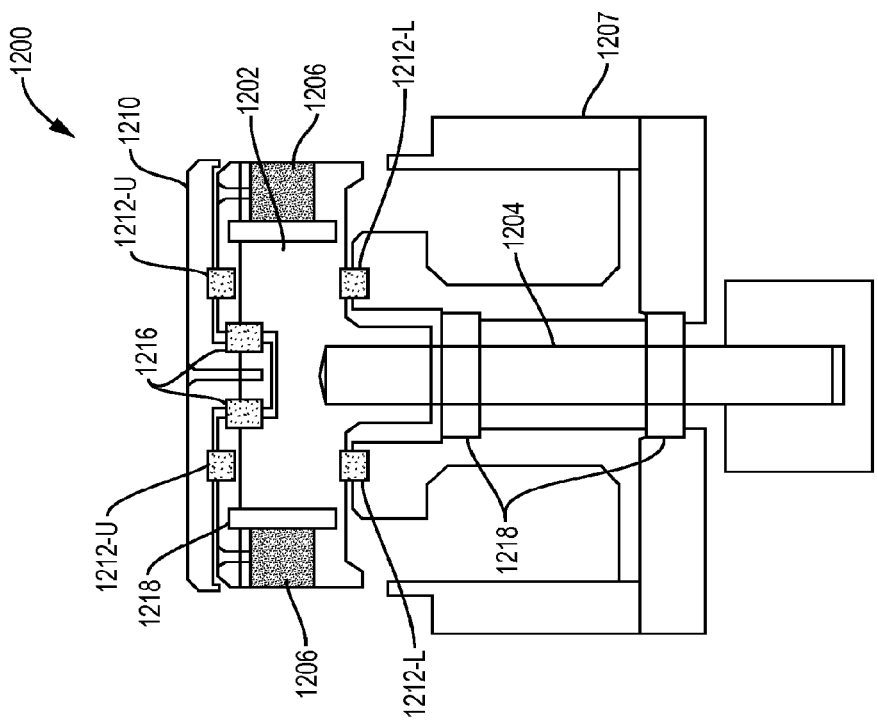
FIG. 13B is a cross-sectional, elevation view of the drive system of FIG. 13A.
Figure 13A:
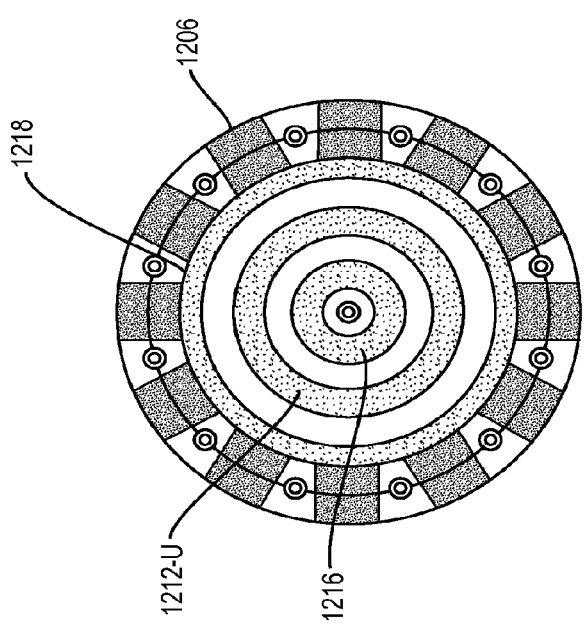
FIG. 13A is a cross sectional, top view of an external drive system with a radial magnetic coupling orientation according to an embodiment of the invention.

FIGS. 13A and 13B show cross-sectional plan and side views, respectively, of a radial magnetic drive system 1200 that includes a drive head 1202 which, as shown in the figure, fits within a non-rotating drive head top 1210 and drive mount 1207. The drive head 1202 is cylindrically-shaped and rotates within the non-rotating drive mount 1207.

The radial magnetic drive system 1200 includes preferably at least two drive magnets 1206 attached or imbedded within the drive head 1202 and positioned below the disc-shaped drive head top 1210. These drive magnets 1206 are typically installed within either molded or machined recesses that are formed into the drive head 1202 or coupled via a support ring 1218 and oriented so that the magnetic field is directed perpendicular or at an intermediate angle relative to the axis of rotation but with a north-south orientation that is compatible for attraction between the drive magnets 1206 and similar radial-oriented agitator magnets (to be discuss further below). The rotating drive head 1202 is supported upper and lower thrust bearings (1212-U and 1212-L, respectively). The radial drive system can further include one or more radial bearings 1216.

Figure 14:
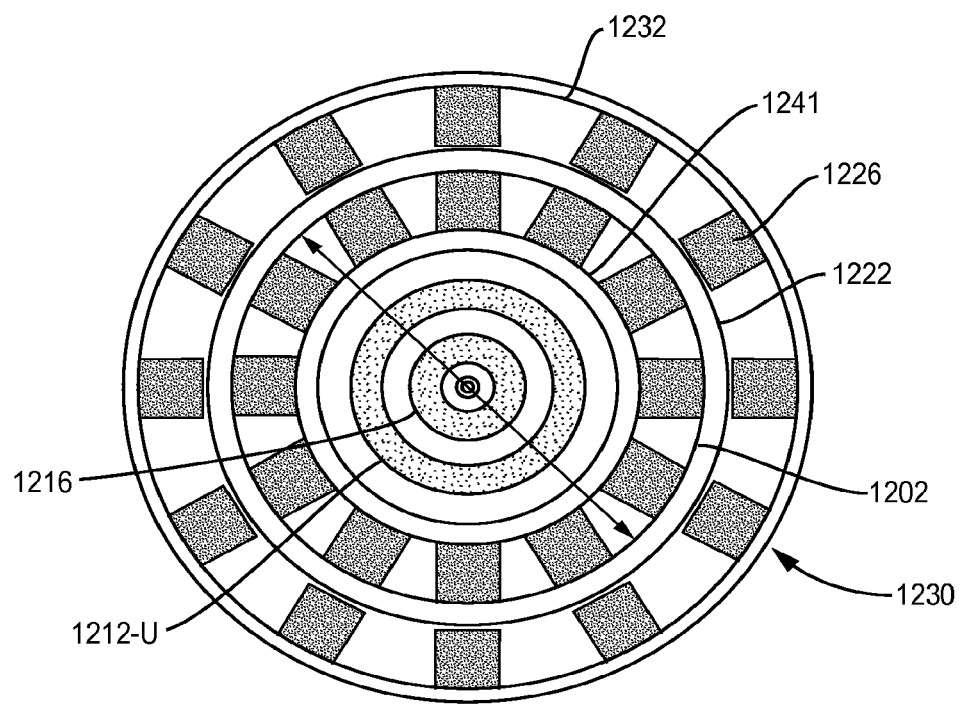
FIG. 14 is cross-sectional, top view of a radial coupling system including a central drive head coupled to a peripheral impeller according to an embodiment of the invention.
Figure 15:
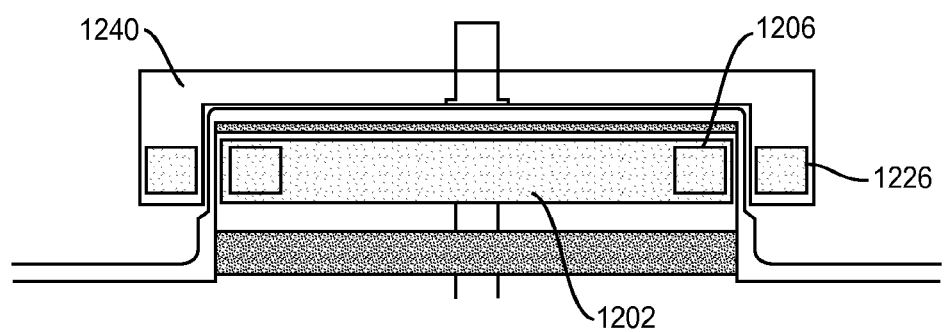
FIG. 15 is a cross-sectional, elevation view of the drive system of FIG. 14.

FIGS. 14 and 15 show cross-sectional plan and side views of the drive head 1202 of the external drive system coupled to an agitator hub assembly 1240 with the fluid container. In this configuration, the magnets 1206 of the drive system 1202 form the inner component and the magnets 1226 of the agitator hub assembly are induced to rotate synchronal with the rotation of the drive head 1202. The agitator hub assembly includes magnets 1226, and can further include a plastic (e.g., HDPE) body 1230, a low carbon steel ring 1232 and a base wall 1222 that support the agitator magnets. Outside of the bag or fluid container, drive head 1202 is supported by bearings 1212-U and 1216. Drive head 1202 can further include a low carbon steel ring 1241 that provides a path for the magnetic flux and addition support for the drive magnets 1206.

Figure 16:
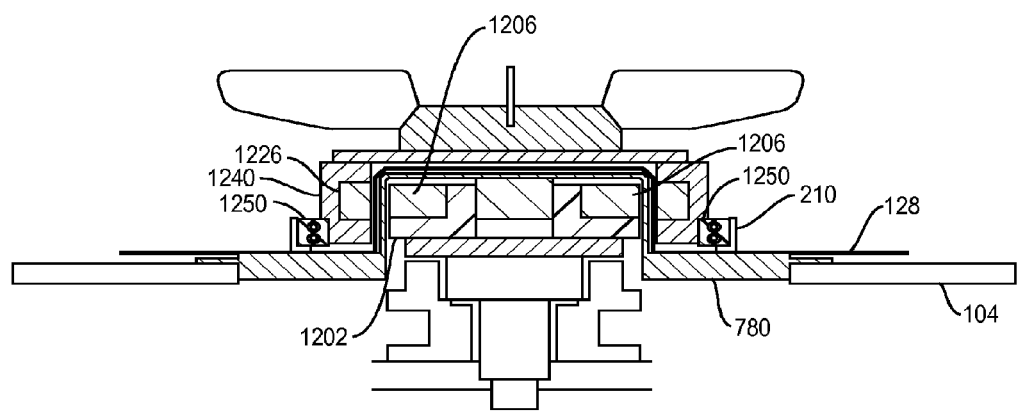
FIG. 16 is cross-sectional, elevation view of another radial coupling system including a central drive head coupled to a peripheral impeller together with a receiver-less retainer according to another embodiment of the invention.
Figure 17:
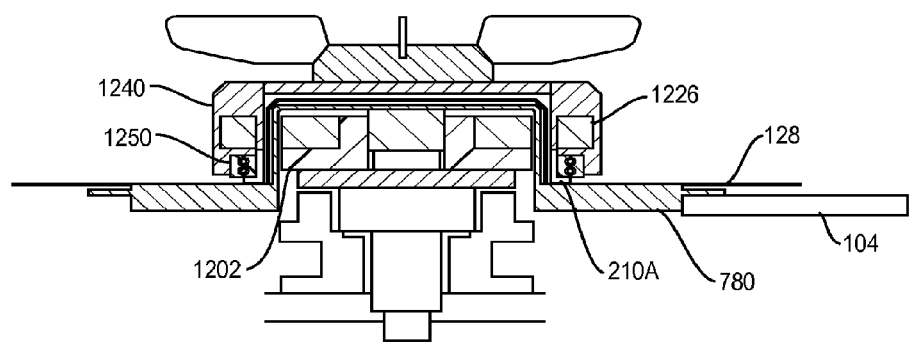
FIG. 17 is cross-sectional, elevation view of yet another radial coupling system including a central drive head coupled to a peripheral impeller together with an alternative receiver-less retainer according to another embodiment of the invention.

FIGS. 16 and 17 show further refinements of radial magnetic coupling in the context of receiver-less retainer systems. In FIG. 16 external drive head 1202 and its magnets 1206 are again disposed in an inner configuration outside of the bag 128 supported by mount 780. The mount 780 is raised relative to the rest of the bottom wall of the support structure, forcing the bag 128 to flex around it. Agitator hub assembly 1240 is disposed with the bag 128 and encircles the mount. The dimensions of the agitator hub body 1240 and annular retainer boot 210 (discussed in detail above) provide clearance for the agitator to rotate without contacting the bag 128. The rotation of the agitator is further guided and supported by a bearing structure or raceway 1250 (also discussed in detail above).) The bearing structure permits the hub 1240 to rotate independently of the supporting structure.

In FIG. 17, boot 210A is shown disposed in an inner configuration (in between bag 128 and agitator hub assembly 1240). Again the bearing structure (raceway) 1250 serves to guide rotation of the agitator.

Figure 18:
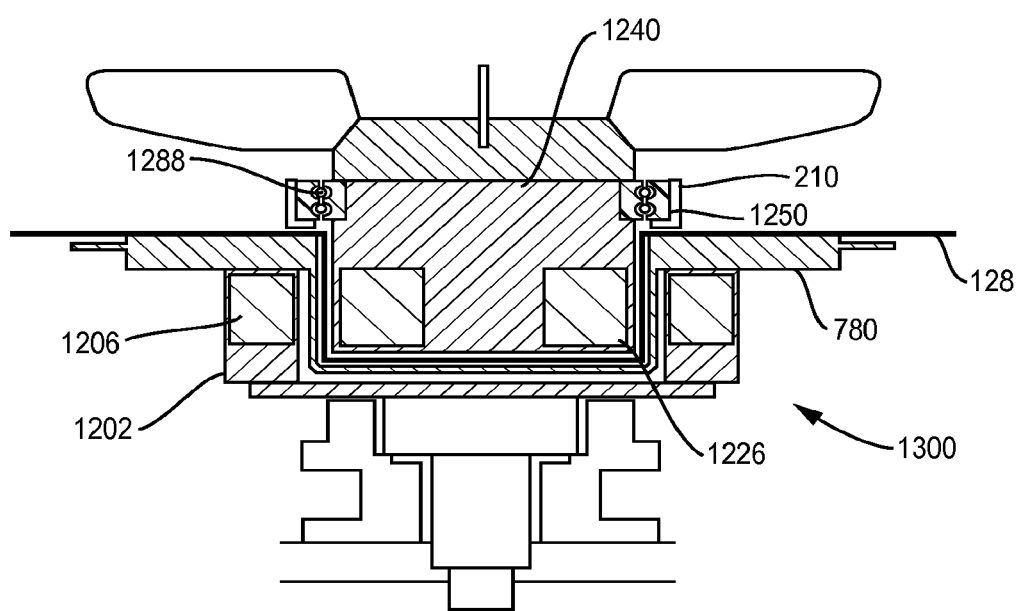
FIG. 18 is cross-sectional, elevation view of another radial coupling system including a central impeller coupled to a peripheral drive head together with a receiver-less retainer according to another embodiment of the invention.

FIG. 18 shows an alternative embodiment of radial-coupling of an external drive system 1300 and an internal agitator assembly 1240. In this embodiment, the external drive head 1202 and its magnets 1206 are again disposed outside of the bag 128 and supported by mount 780. Magnets 1206, however, are disposed in an outer (peripheral) configuration relative to the mount. (Bearings and ancillary supports for the rotatable drive head 1202 have been omitted for simplicity of illustration but can be readily understood to also be present.) In this embodiment, mount 780 includes a sunken portion relative to the rest of the bottom wall of the support structure, forcing the bag 128 to be draped down into sunken portion. Agitator hub assembly 1240 is disposed with the bag 128 and also is disposed within the sunken portion of the drive assembly mount. The dimensions of the agitator hub body 1240 and annular retainer boot 210 provide clearance for the agitator to rotate without contacting the bag 128. The rotation of the agitator is further guided by the bearing structure (raceway) 1250, e.g., employing double ball bearings 1288 between an inner and outer race. (See FIGS. 3 and 4 for further details on raceway designs.)

Figure 19A:
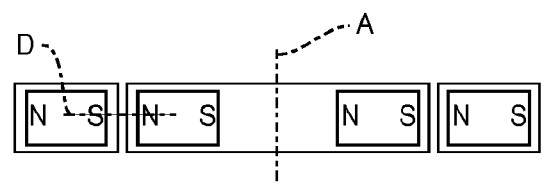
FIG. 19A-19D are schematic illustrations of additional radial (non-orthogonal) magnetic coupling arrangements between an impeller and an external drive system in which the direction of coupling is less than 90 (but greater than zero) degrees from the axis of rotation.
Figure 19B:
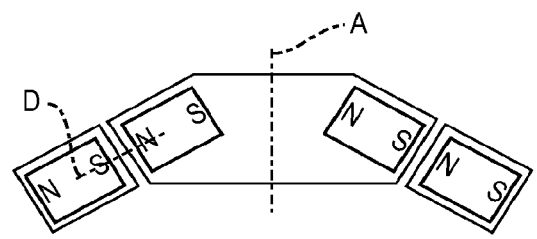
Figure 19C:
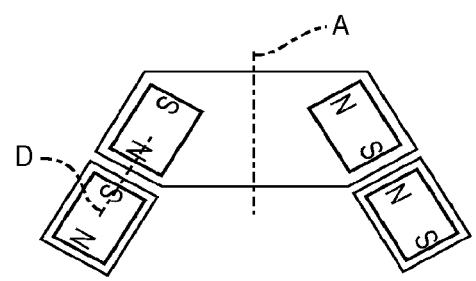
Figure 19D:
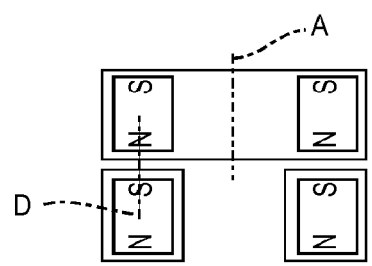

FIGS. 19A-19D illustrate a further aspect of the invention in which radial coupling of the driver and agitator magnets need not be strictly perpendicular to the axis of rotation. The magnetic agitator is therefore preferably configured such that the radial coupling between the agitator magnets and the drive magnet is at angle greater than zero degrees relative to the axis of rotation, 'A'. The angle is preferably greater than about 10 or even more preferably more than 20 degrees relative to the axis of rotation In FIG. 19A the magnets are oriented such that the direction of magnetic coupling force, 'D', is only a few degrees off perpendicular relative to the axis of rotation, 'A', e.g., 88 degrees. In FIG. 19B the magnets are oriented such that the direction of magnetic coupling force, 'D', is about 60 degrees off perpendicular relative to the axis of rotation, 'A'. In FIG. 19C the magnets are oriented such that the direction of magnetic coupling force, 'D', is about 30 degrees relative to the axis of rotation, 'A' and in FIG. 19D the magnets are oriented such that the direction of magnetic coupling force, 'D', is only a few degrees off parallel relative to the axis of rotation, 'A', e.g., 2 degrees. More generally speaking, the quasi-radial coupling between the drive and agitator magnets can be the range from about 1 degree to about 90 degrees, more preferably between 15 and 75 degrees to take advantage of the coupling efficiency that radial coupling affords, and in some instances more preferably between 30 and 60 degrees. Depending on the application and configuration, quasi-radial coupling can be particularly advantageous if the coupling angle (relative to the axis of rotation) is 90 degrees or less than 90 but greater than 85, 80, 75, 70, 65, 60, 55, 50, 45, 40, 35, 30, 25, 20 or 15 degrees.

Figure 20:
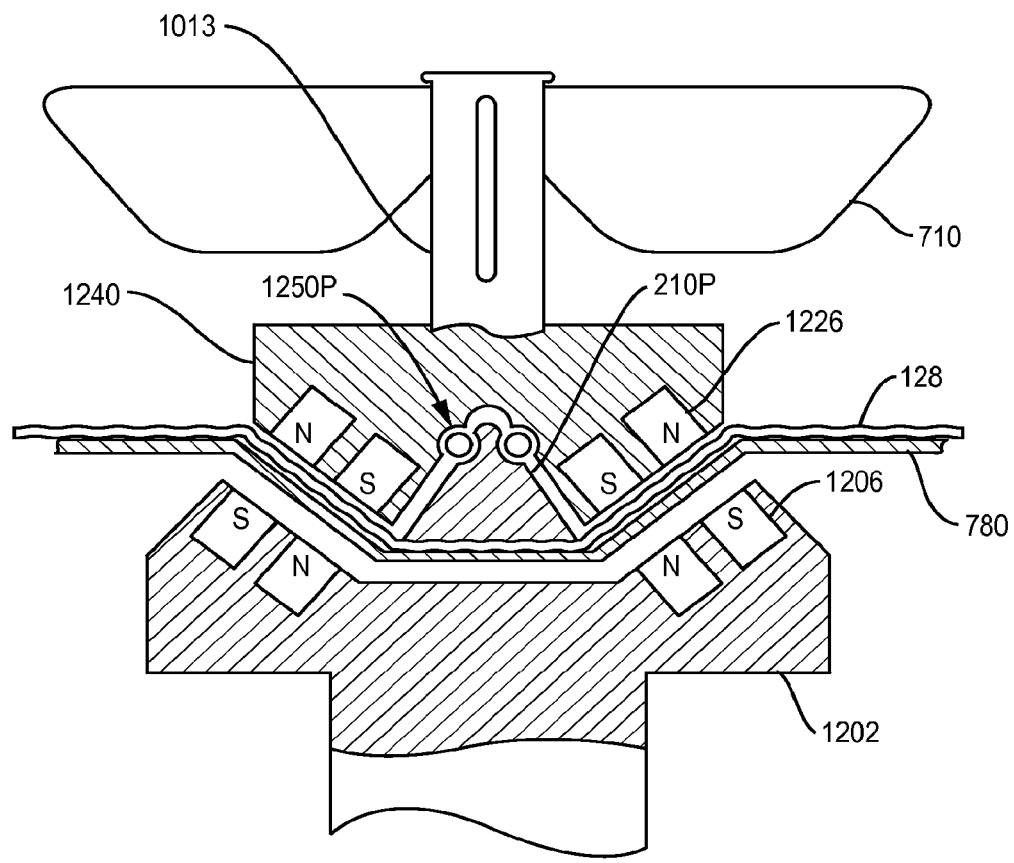
FIG. 20 is cross-sectional, elevation view of a quasi-radial coupling system including a central impeller coupled to a peripheral drive head in which the direction of coupling is 45 degrees relative to the axis of rotation according to another embodiment of the invention.

FIG. 20 illustrates yet another embodiment of the invention in which quasi-radial coupling at roughly 45 degrees is employed. In this embodiment, the external drive head 1202 and its magnets 1206 are again disposed outside of the bag 128 and supported by mount 780. A double row of magnets 1206 are disposed in an outer (peripheral) configuration at an angle of about 45 degrees relative to the axis of rotation. (Again, bearings and ancillary supports for the rotatable drive head 1202 have been omitted for simplicity of illustration but can be readily understood to also be present.). The flexible bag 128 is configured to be supported by a support structure 104 that at least partially surrounds the bag during use and the flexible bag is further adapted for deformation by a shaped mount 780 of the support structure 104 to define a receiverless retainer for the magnetic agitator within the bag 128 when the agitator magnets 1226 are coupled to external drive magnets 1206. In this embodiment, mount 780 includes a sunken portion relative to the rest of the bottom wall of the support structure, forcing the bag 128 to be draped down into sunken portion. Agitator hub assembly 1240 with its agitator magnets 1226 is disposed with the bag 128 and also is disposed within the sunken portion of the drive assembly mount. The agitator magnets 1226 are oriented at the same angle as the drive magnets 1206 such that the direction of the magnetic coupling force is at roughly 45 degrees relative to the axis of rotation The dimensions of the agitator hub body 1240 and a central conical boot 210P provide clearance for the agitator to rotate without contacting the bag 128. The rotation of the agitator can further guided by the bearing structure (raceway) 1250P, e.g., again employing ball bearings between an inner and outer race.

Figure 21:
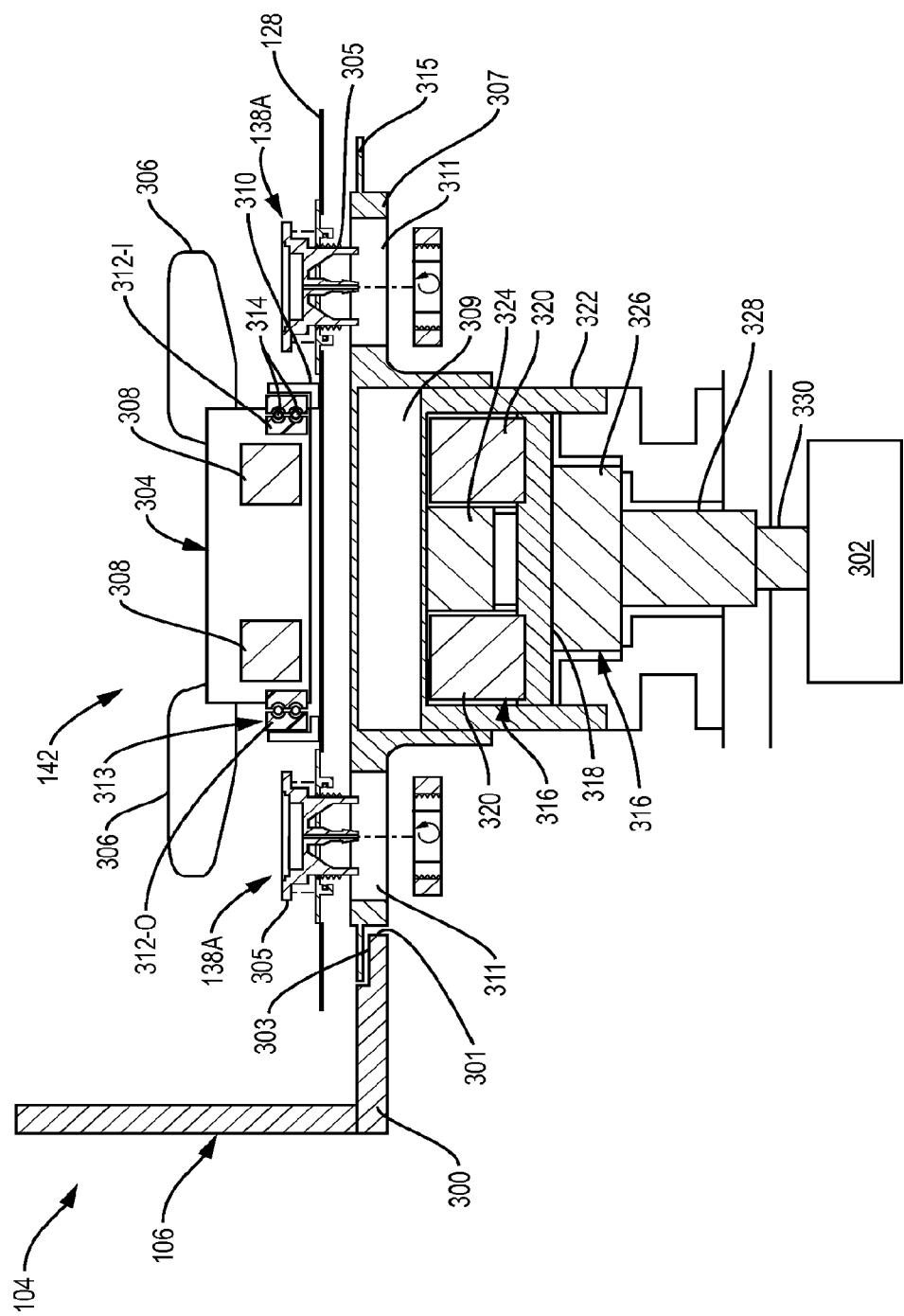
FIG. 21 is a schematic partial cross-sectional, partial exploded view of one embodiment of the agitation and bulkhead system including a bulkhead sparger in a bioreactor according to an embodiment of the invention.

FIG. 21 shows an agitation and bulkhead system 200 that has been constructed according to the principles of the present invention. The main components of this agitation and bulkhead system 200 include the magnetic agitator 142, the external magnetic drive system 121, and at least one bulkhead unit 138 specifically first bulkhead sparger 138A. It should be noted that the bulkhead system may be used in a bag support structure 104 defining a receiverless retainer for the agitator as shown for example in any one of FIG. 5-6, and/or FIGS. 16-18, and 20.

The agitation and bulkhead system 200 components interact externally and internally to the bag 128 and the bag support structure wall 106. The magnetic drive system 121 rotates external to the bottom of the bag support structure wall 106 causing rotation of the magnetic agitator 142 which rotates within the bag 128. The bulkhead units 138 are inserted within the bottom of the bag support structure wall 106 and bag 128.

The bag support structure 104 has a bag support structure wall 106 that forms the outer structure of the bag support structure 104. The bag support structure wall 106 includes a bottom plate 300 that forms the bottom of the bag support structure 104. The bag support structure wall 106 has an agitator port 301 or aperture formed in the center of the bottom plate 300. The bottom plate 300 includes a slotted edge 303 along the perimeter of the agitator port 301.

The bag support structure wall 104 surrounds a bag 128 that fits along the inner surface of the bag support structure wall 106. As described above, this bag 128 is typically a single-use flexible bag. The bag 128 includes at least one aperture and a sparger assembly or bulkhead sparger 138A is adapted for sealing against the at least one aperture. Thereby a fluid-tight passageway is provided to introduce a gas into the bag 128 when filled with fluid. As shown in FIG. 21, the bottom of the bag 128 includes at least two bulkhead unit ports 305 allowing insertion of a bulkhead unit 138 such as the first bulkhead sparger 138A.

The agitation and bulkhead system 200 includes preferably a disc-shaped bag support structure wall insert 307 shaped to fit within the agitator port 301 of the bottom plate 300. The bag support structure wall insert 307 includes a drive system cylindrical slot 309 on a bottom face of the bag support structure wall insert 307. The bag support structure wall insert 307 also includes at least two bulkhead unit apertures 311 that are positioned around the perimeter of the drive system slot 309. These bulkhead unit apertures 311 are positioned to align with the bulkhead unit ports 305 of the bag 128. The bag support structure wall insert 307 may have a flange 315 along the outer edge of the disc-shaped bag support structure wall insert 307 that fits over the slotted edge 303 of the agitator port 301. The flat top surface and flat bottom surface of the disc-shaped bag support structure wall insert 307 provide an even planar interface for receiving with the external magnetic drive system 121 and internal magnetic agitator 142.

System 200 includes a magnetic agitator 142. The magnetic agitator 142 performs the mixing for system 200. Magnetic agitator 142 rotates within the bag 128 in order to help mix a substance as part of a process or reaction.

Magnetic agitator 142 includes an agitator hub 304. The agitator hub 304 has a squat cylindrical shape. The structural material of the hub 304 is preferably a material that is non-magnetic and corrosion resistant such as plastic.

Magnetic agitator 142 may include at least two wing-shaped set of blades or vanes 306 attached or mounted to the agitator hub 304 and have generally rectangular profiles, in the specific embodiment illustrated. The blades 306 project vertically and radially from the hub 304 and are usually evenly spaced around the periphery of the hub 304 so that the hub spins in a balanced fashion. The vanes/blades 306 are attached to the agitator hub by pins (not shown) in one example. Alternatively, the vanes/blades 306 are integrated or molded with the agitator hub. Also, in another example, three or more vanes/blades are fixed to the agitator hub preferably equally spaced apart around the perimeter of the hub.

The vanes/blades 306 engage a substance, such as a fluid, within the bag 128 in order to mix the substance. The pitch of the vane/blade is typically set in order to achieve optimum mixing of the substance. Rotation of the vanes/blades produces axially-directed forces that urge the substance or fluid downwards or upwards depending on the direction of rotation of the hub.

The agitator hub 304 is preferably positioned slightly above the inner surface of the bag 128 which allows for fluid to pass underneath the hub 304 and through a flow channel (not shown). This setup produces centrifugal flow by the spinning of the magnetic agitator 142 while fluid is swept past the sides of the magnetic agitator 142 and through a flow channel. As the vanes/blades 306 rotate, the rotation results in a difference in pressure that forces the fluid across this pathway. This can also be helpful during the cleaning process by easily flushing fluid around and through the magnetic agitator 142.

The magnetic agitator may 142 include at least two hub magnets 308 attached or imbedded within the plastic agitator hub 304. These magnets are typically sent into voids that are either molded or machined into the body of the agitator hub 304 and oriented such that the magnetic field is directed along the vertical axis of the hub 304 for compatible attraction with the magnetic drive system 121.

Preferably, the magnetic agitator 142 includes more than two hub magnets 308 that are spaced equidistantly around the perimeter of the agitator hub 304 in a circular fashion forming an array of magnets. The number of hub magnets is determined based on the desired magnetic flux needed and also the physical size constraints of the hub 304. Typically, the larger the bag 128, the more magnets needed. The hub magnets 308 are preferably high performance rare earth magnets that produce stronger magnetic fields. For example, a magnet made from neodymium-iron-boron is used in one embodiment.

The magnetic agitator 142 may include an agitator bearing structure 313 for supporting the hub 304 above the bag insert 307 and the bag 128 while allowing the hub 304 to rotate around its central axis. This agitator bearing structure 313 is a bearing assembly including roller or ball bearings, for example.

This bearing assembly may include an inner bearing race 312-I and an outer bearing race 312-O, with the inner bearing race 312-I being attached to the lower perimeter of the agitator hub 304 and specifically sitting in a recess formed in the bottom outer edge of the hub 304. The inner bearing race 312-I may be coupled or mated with the outer bearing race 312-O via a double ball bearing configuration. For this configuration, the ball bearings 314 extend through the races with spacers separating (not shown) each ball bearing 314 from one another. The combination of the bearing races 312-I/312-O and the double ball bearings 314 allows the hub 304 to freely rotate around its axis on the bag insert 307 in the bag 128 with less friction.

The ball bearing configuration is typically, but not limited to, either a single ball or a double ball arrangement. The single ball arrangement is characterized by having only one level of ball bearings versus two for the double ball bearing arrangement. The bearing configuration can be of a radial bearing, angular contact bearing, or thrust bearing type. Use of ball bearings for the agitator bearing structure allows for fluid to flow around the ball bearings providing lubrication (i.e. lower friction) and cooling of the bearings during use. The ball bearings and inner/outer bearing races are preferably made from a material that is corrosion resistant, low cost, lightweight, and/or disposable. This allows for the bearing configuration to be discarded after each use or alternatively be easily sterilized/cleaned for reuse. For example, the bearing races can be made from plastic or nickel-beryllium alloy and the ball bearings can be made from a hybrid ceramic such as silicon nitride or a plastic material. The bearing configuration provides an overall low-friction support to the agitator.

The agitator hub 304 with its agitator bearing structure 313 can be positioned on the bottom surface of the bag 128 within a supporting structure 310, that may be an annular-shaped boot structure 310. A lower face of the boot 310 sits directly on the inner surface of the bag 128 to support the outer bearing race 312-O above the bag 128. The boot 310 is typically a plastic ring, washer, or bushing and is preferably comprised of a flexible polymeric material such as silicon or EPDM (ethylene propylene diene Monomer (M-class) rubber). The agitator hub 304 rotates along the bearing assembly with the outer bearing race 312-O press fit within boot 310.

The magnetic drive system 121 may control the rotation of the magnetic agitator 142 via magnetic forces from outside the bag support structure wall 106 and through the non-metallic disc-shaped bag insert 307. The magnetic drive system 121 is situated external to the bag support structure wall 106 and bag 128 within the drive system slot 309 of the bag insert 307. Torque is transmitted from the magnetic drive system 121 rotating within the drive system slot 309 to the magnetic agitator 142 due to the magnetic forces between the magnetic drive system 121 and the hub magnets 308 embedded within the magnetic agitator 142.

The magnetic drive system 121 may include a drive head 316 that fits within a drive head cowling 322. The drive head 316 is cylindrically-shaped and rotates within the non-rotating drive head cowling 322.

The magnetic drive system 121 may include at least two drive magnets 320 attached or imbedded within the drive head 316 and positioned below the disc-shaped bag insert 307. These drive magnets 320 are typically installed within either molded or machined recesses that are formed into the drive head 316 and oriented so that the magnetic field is directed parallel to the hub magnets 308 and parallel to the axis of rotation but with a north-south orientation that is compatible for attraction between the drive magnets 320 and hub magnets 308.

Preferably, the magnetic drive system 121 includes more than two drive magnets 320 spaced equidistantly around the perimeter of the drive head 316 forming an array of magnets. The number of drive magnets is preferably the same as the number of hub magnets. The drive magnets 320 provide the magnetic force needed to enable torque transfer to drive the magnetic agitator 142 within the bag 128. As the drive magnets 320 rotate, they cause the magnetic agitator 142 to rotate due to the magnetic attraction between the hub magnets 308 and drive magnets 320. The magnetic forces produced by movement of the drive magnets 320 cause the opposing poles of the hub magnets 308 to react by moving in the same direction of rotation so that when the drive head 316 rotates, the magnetic agitator 142 rotates. The drive magnets are rare earth magnets that produce stronger forces of attraction as compared to standard magnets.

The drive head 316 may include a number of components for supporting and aiding the drive head 316 in terms of rotation within the drive system slot 309 of the bag insert 307. The drive head 316 includes a drive head base 318 for supporting the drive magnets 320 within the drive head cowling 322. The drive head cowling 322 has a hollow cylindrical form for surrounding the drive head base 318 along with the inner drive magnets 320.

The drive head 316 may include a lazy-susan bearing 324 for enabling it to rotate against the non-rotating drive head cowling 322. The lazy-susan bearing 324 is situated at the top center portion of the drive head 316 on its axis of rotation, and between the drive magnets 320. The lazy-susan bearing 324 interacts along the inner face of the drive head cowling 322 causing rotation of the drive head 316.

The drive head 316 may also include a thrust plate 326 that is attached to the bottom of the drive head base 318 along the center axis of the drive head 316 in parallel with the lazy-susan bearing 324.

The magnetic drive system 121 includes a number of components that connect the motor 302 to the drive head 316 in order to produce and control rotation of the drive head 316. The motor 302 within the magnetic drive system 121 is typically an electric drive motor such as a variable speed electric motor, a pneumatic driven motor, a hydraulic drive motor, or the like. The motor 302 is connected directly to a motor shaft 330. The motor shaft 330 terminates in a thrust bearing 328. The thrust bearing 328 is connected directly to the thrust plate 326 of the drive head 316. This causes rotation of the drive head 316 including the drive magnets 320 when the motor 302 is in operation. The thrust plate is of a larger diameter than the thrust bearing which is of a larger diameter than the motor shaft. Therefore, the thrust plate is concentrically received over the thrust bearing which is concentrically received over the motor shaft.

These driving parts within the magnetic drive system 121 are together axially aligned. As the magnetic drive system 121 starts initiating, the magnetic agitator 142 automatically orients and aligns with the drive head due to the magnetic attraction.

System 200 includes preferably at least one bulkhead unit 138 specifically a first bulkhead sparger, also referred to as a sparger assembly or sparger unit, 138A. As shown in FIG. 21, the first bulkhead spargers 138A fit within the bulkhead unit ports 305 in the bag 128 and the bulkhead unit apertures 311 within the bag insert 307. The first bulkhead unit spargers 138A provide bubbling of gases into the bag 128 in order to maintain a fairly constant level of gas within the system 200.

In the preferred embodiment, the bulkhead unit spargers 138A are located adjacent to the agitator hub 304 and under the at least two wing-shaped set of blades or vanes 306 attached or mounted to the agitator hub 304. Locating the spargers 138A beneath the vanes 306 helps to ensure that gas entering from the spargers is immediately mixed with the fluid in the bag 128 by the action of the vanes 306.

Figure 22:
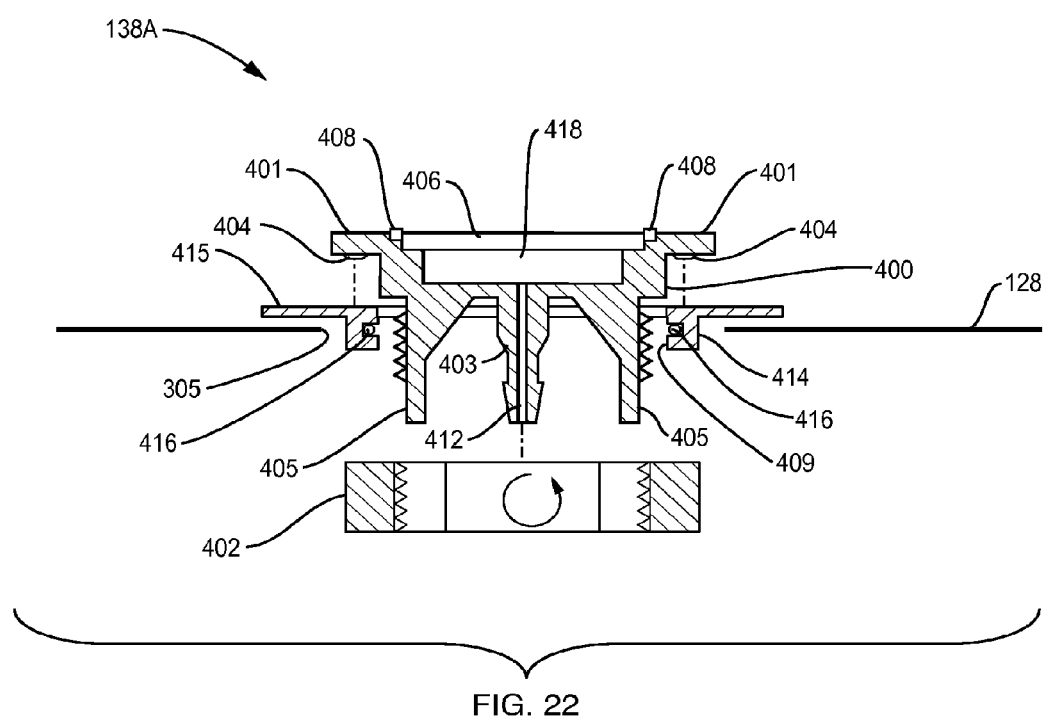
FIG. 22 is a schematic cross-sectional view of the bulkhead sparger from FIG. 21 according to an embodiment of the invention.

FIG. 22 shows the first bulkhead sparger 138A fitting within a first bushing 414 of the bag 128. The first bushing 414 is permanently affixed to the flexible bag 128 within the bulkhead unit port or aperture 305 such as by plastic welding or by an epoxy bond. The first bushing 414 has an outward flange section 415 allowing it to fit in the bulkhead unit port 305 while the flange 415 sits along and is affixed to the edge of the bag 128. The first bushing 414 is made from a plastic or rigid polymeric material. In an alternative example, the first bushing 414 is a washer or port plate.

The first bushing 414 includes a bushing gasket 416 along its inner surface allowing it to seal against the inserted first bulkhead sparger 138A. In an alternative example, the bushing gasket is an o-ring.

The first bulkhead sparger 138A includes a first sparger body or base 400 and a fastener 402. The fastener 402 rotatably attaches to the first sparger base 400 that is inserted within the bulkhead unit port 305 of the bag 128 and the inner port 409 of the bushing 414 to form the first bulkhead sparger 138A. The first sparger base 400 and fastener 402 include screw threads allowing attachment to each other. The first sparger base 400 in combination with the fastener 402 are sized to fit within the first bushing 414 of the bag 128 and the bulkhead unit aperture 311 of the bag insert 307.

The first sparger base 400 may be seated thru the first bushing 414. The first sparger base 400 generally includes a first base gasket 404, a sparging disc 406, disc sealing elements 408, a gas flow artery 412, and a fitting or a base barb 410. An external gas line can be coupled to the plenum 418 by means of the fitting 410. The first sparger base 400 is made from a plastic or other rigid polymeric material.

The first sparger base 400 is configured so that the sparging disc 406 stretches along the top of the base 400 forming a gas plenum 418 between the sparging disc 406 and the first sparger base 400. The first sparger base 400 includes flange outer sections 401 stretching along the top edge of the base 400 for sitting along the top surface of the first bushing 414. The flange is 401 adapted to substantially surround the bag aperture and seal the bulkhead sparger by sandwiching the flexible bag 128 between the flange 401 and a support structure 106.

The first sparger base 400 may also include a gas flow artery 412 that forms a central section 403 from the gas plenum 418 to the base barb 410. Outer lower section 405 forms a hollow cylinder that projects from the plenum and through the inner port 409 of the bushing 414 and surrounds this gas flow artery section 403 having outer screw grooves for attaching to the fastener 402 as well as protecting the central gas flow artery section 403.

The first base gasket 404 may be positioned along a bottom surface of the outer base flange sections surrounding the first sparger base 400. The first base gasket 404 is made from silicone rubber or a flexible polymeric material. In an alternative example, the first base gasket 404 is an o-ring.

The sparging disc 406 may be positioned along the top of the first sparger base 400. The sparging disc 406 is made from a porous stainless steel or sintered metal. These sparging discs 406 functions to allow passing gases from the gas plenum 418 into the bag 128 causing a bubbling effect.

The disc sealing element 408 is positioned between the sparging disc 406 and the first sparger base 400. This disc sealing element 408 forms a seal between the outer perimeter of the sparging disc 406 and the first sparger base 400 to prevent leakage. The disc sealing element 408 is made from a plastic or rigid polymeric material.

The base barb 410 may be formed at the outer end of the central gas flow artery 412 section. The base barb 410 allows a hose to be connected directly to the first bulkhead sparger 138A external to the bag support structure wall 106 and bag 128. The hose (not shown) connects directly onto the base barb 410 enabling a specific gas or combination of gases to be delivered from the center gas flow artery 412 to the gas plenum 418 to be expressed through the sparging disc 406.

The first bulkhead sparger 138A includes a fastener 402. The fastener 402 may be a bulkhead nut. The fastener 402 includes threads along its internal surface for mating to the first sparger base 400 and tightened against the first bushing 414 to form an aseptic, non-permanent seal.

Figure 23:
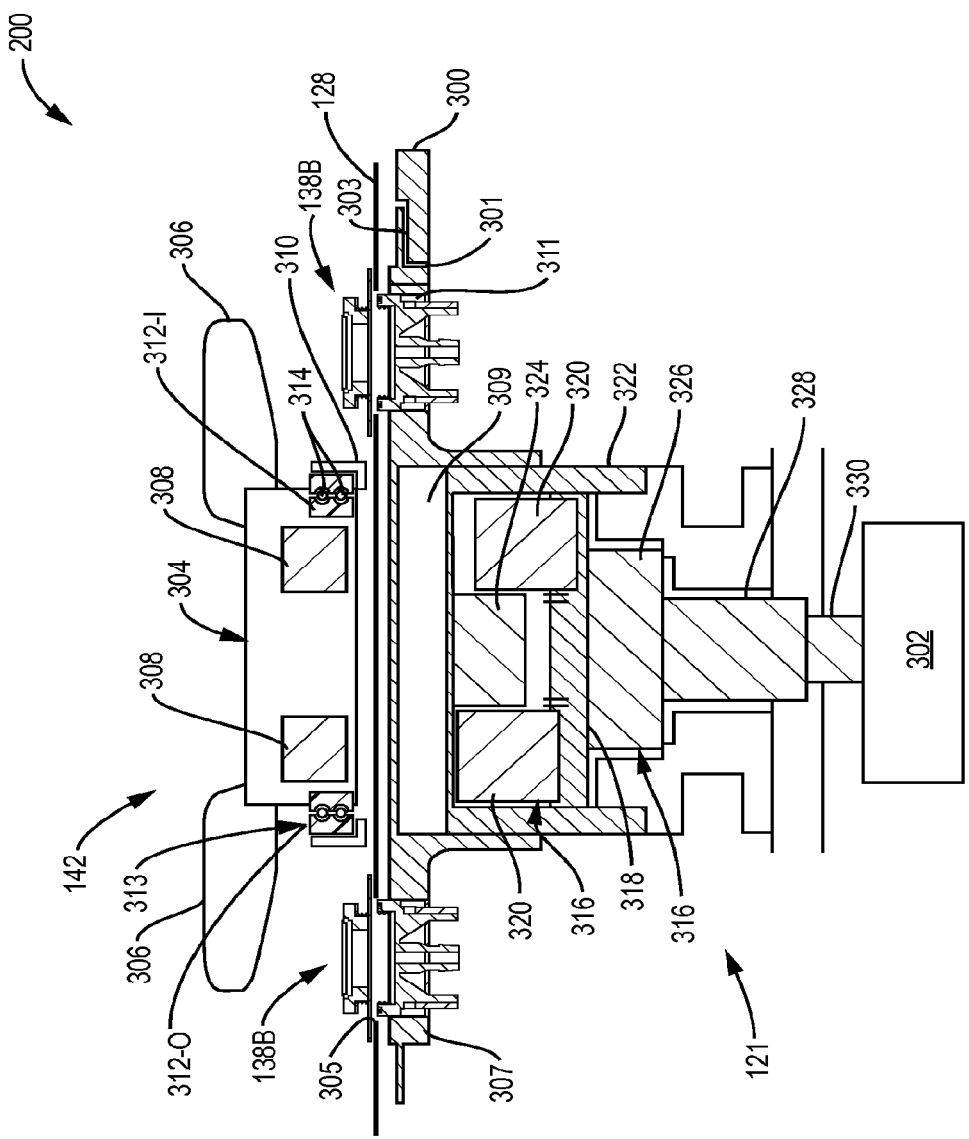
FIG. 23 is a schematic partial cross-sectional, partial exploded view of the agitation system including a bulkhead sparger in a bioreactor or mixer with gassing according to a second embodiment of the invention.

FIG. 23 is a schematic cross-sectional view of an agitation and bulkhead system 200 that has been constructed according to the principles of the present invention. System 200 includes the same components described above in FIG. 22 except it includes the second bulkhead sparger 138B according to a second embodiment.

Figure 24:
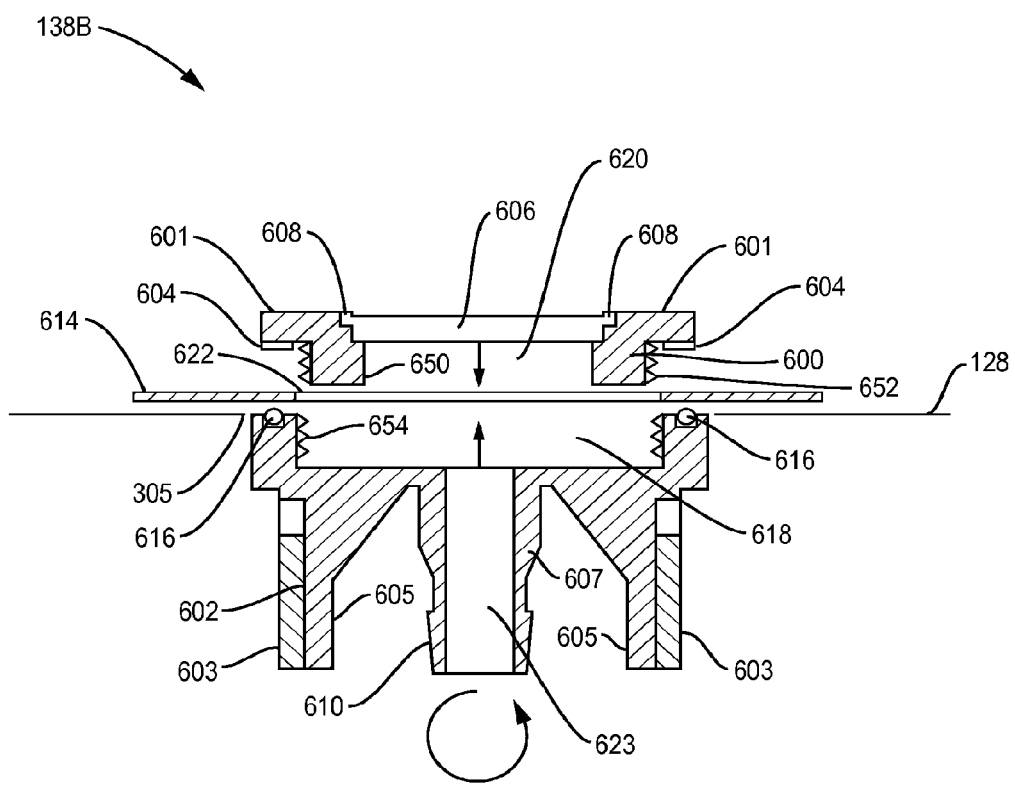
FIG. 24 is a schematic cross-sectional, partial exploded view of the bulkhead sparger from FIG. 14 according to a second embodiment of the invention.

FIG. 24 shows the second bulkhead sparger 138B in more detail. It fits within a second bushing 614 of the bag 128. The second bushing 614 is permanently affixed to the flexible bag 128 along the edge of the bulkhead unit port 305 such as by welding or an epoxy bond so that the second bushing 614 fits over the bulkhead unit port 305. The second bushing 614 is a thin cylindrical piece having a central port 622 forming the sparge seal ring cavity. The second bushing 614 is made from a plastic or rigid polymeric material. In an alternative example, the second bushing 614 is a washer or port plate.

The second bulkhead sparger 138B may include a second sparger base 600 and a barbed fastener 602. The barbed fastener 602 screws onto and thus attaches to the second sparger base 600 within the bulkhead unit port 305 of the bag 128 to form the second bulkhead sparger 138B. The second sparger base 600 and barbed fastener 602 include screw threads allowing attachment to each other. The second sparger base 600 in combination with the barbed fastener 602 are shaped to fit within the bulkhead unit aperture 311 of the bag insert 307.

The second sparger base 600 fits within the second bushing 614. The second sparger base 600 generally includes a second base gasket 604, a sparging disc 606, and disc sealing elements 608. The second sparger base 600 is made from a plastic or other rigid polymeric material.

The second sparger base 600 may be configured so that the sparging disc 606 stretches along the top of the base 600 forming a sparge plenum or cavity 620 between the sparging disc 606 and the second sparger base 600. The second sparger base 600 includes flange outer sections 601 stretching along the top edge of the base 600 for sitting along the top surface of the second bushing 614. The second sparger base 600 has a short lower cylindrical body section 650 that fits through the second bushing 614. This lower body section 650 has screw grooves 652 on its outer surface allowing the second sparger base 600 to rotatably attach within the barbed fastener 602 by engaging threads 654.

The second base gasket 604 may be positioned along a bottom surface of the flange outer sections 601 to seal where the second sparger base 600 sits on the second bushing 614. The second base gasket 604 is made from silicone rubber or a flexible polymeric material. In an alternative example, the second base gasket 604 is an o-ring.

The sparging disc 606 is positioned along the top of the second sparger base 600. The sparging disc 606 may be made from a porous stainless steel or sintered metal. The sparging disc 606 functions in delivering gas from the sparge retention cavity 620 into the bag support structure wall 106 and bag 128 similar to sparging disc 406.

The disc sealing element 608 is positioned between the sparging disc 606 and the second sparger base 600. This disc sealing element 608 forms a seal between the outer perimeter of the sparging disc 606 and the second sparger base 600 to prevent leakage. The disc sealing elements 608 may be made from a plastic or rigid polymeric material.

The barbed fastener 602 generally includes a gas flow artery 623, a barb 610, a protective tab 603, and a fastener gasket 616. The barbed fastener 602 includes an upper cylindrical section that forms the gas plenum 618. This cylindrical section includes threaded grooves along the inner surface surrounding the gas plenum 618 for attaching to the second sparger base 600. The second sparger base 600 rotatably locks into the threads while fitting into the space 618 of the barbed fastener 602. This forms an aseptic, non-permanent seal between the second sparger base 600 and the barbed fastener 602.

The barbed fastener 602 may include a fastener gasket 616 along the top edge of upper cylindrical section. The fastener gasket 616 is situated along the top surface of the barbed fastener 602 surrounding the gas plenum 618 so that the fastener gasket 616 forms a seal against the bottom surface of the second bushing 614 within the bulkhead unit port 305 of the bag 128. The fastener gasket is alternatively an o-ring seal.

The barbed fastener 602 includes a gas flow artery 623 that is formed in a central section 607 from the gas plenum 618 to the barb 610. Outer lower section 605 of the barbed fastener 602 surrounds this gas flow artery section 607 protecting the barb 602 from being damaged.

A barb 610 is formed around the outer end of the central gas flow artery section 607. The barb 610 allows a hose to be connected directly to the second bulkhead sparger 138B external to the bag support structure wall 106 and bag 128. The hose (not shown) connects directly onto the barb 610 enabling a specific gas or combination of gases to be delivered from the center gas flow artery 612 to the gas plenum 618 through the second bushing 614 to be bubbled by the sparging disc 606 from the sparge retention cavity 620 into the bag 128.

The barbed fastener 602 may further include a protective tab 603 that attaches to and surrounds the outer lower sections 605 of the barbed fastener 602 providing additional protection for the barb 610.

Figure 25:
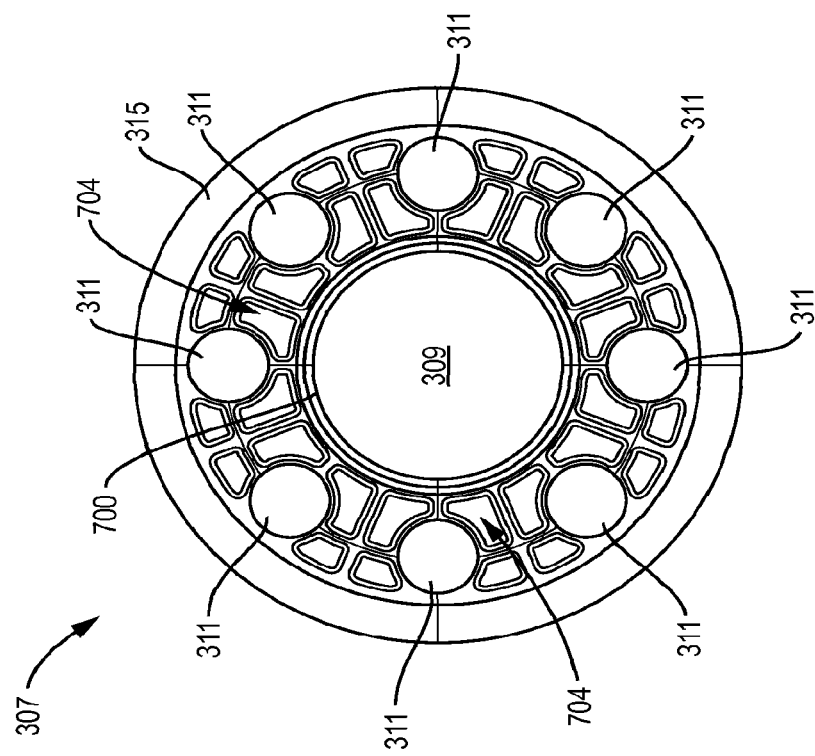
FIG. 25 is a bottom view of the disc-shaped insert from FIGS. 21 and 23 according to an embodiment of the invention.

FIG. 25 shows a bottom view of the bag insert 307. As described above, the bag insert 307 includes a centrally located drive system slot 309 on the bottom surface of the insert 307. The drive system slot 309 has a circular shape from the top view. The bag insert 307 also includes a retainer wall 700 defining the drive system slot 309.

The bag insert 307 may further include circular bulkhead unit apertures 311 surrounding the retainer wall 700 and the central drive system slot 309. A flange 315 surrounds the outer perimeter of the bag insert 307 for fitting within the agitator port 301 of the bottom plate 300. The bag insert 307 includes a cavity section 704 surrounding the bulkhead unit apertures 311 and situated between the outer flange 315 and the drive system slot 309. This cavity section 704 has a honey-combed shape to improve mechanical rigidity.

Figure 26:
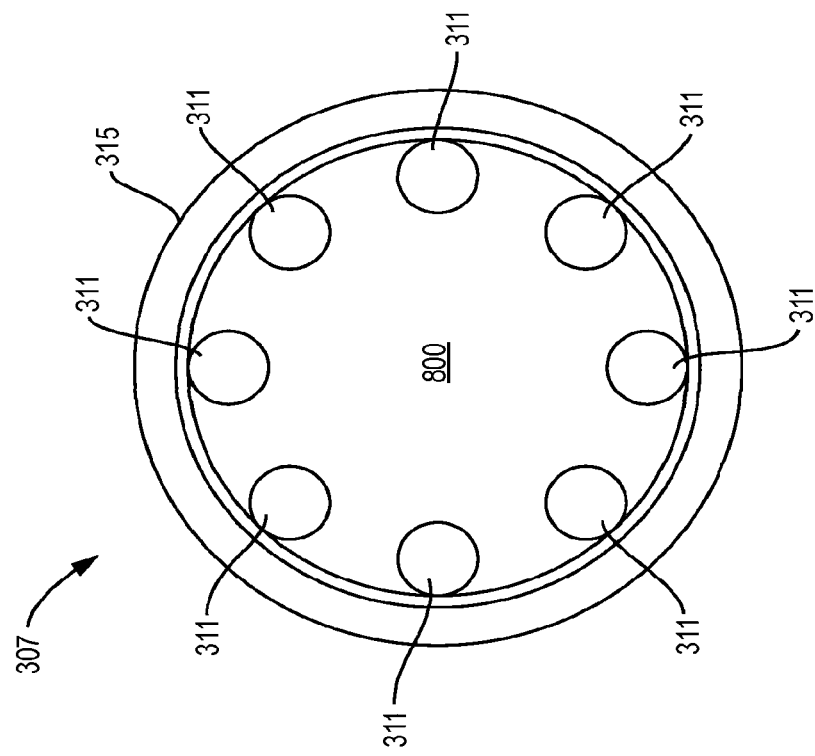
FIG. 26 is a top view of the disc-shaped insert from FIGS. 21 and 23 according to an embodiment of the invention.

FIG. 26 shows a top view of the bag insert 307. This view also includes circular bulkhead unit apertures 311 and the outer flange 315 surrounding a center 800 of the insert 305. The center area 800 is an agitator pan for providing a flat planar surface for the magnetic agitator 142 to rotate on.

Figure 27:
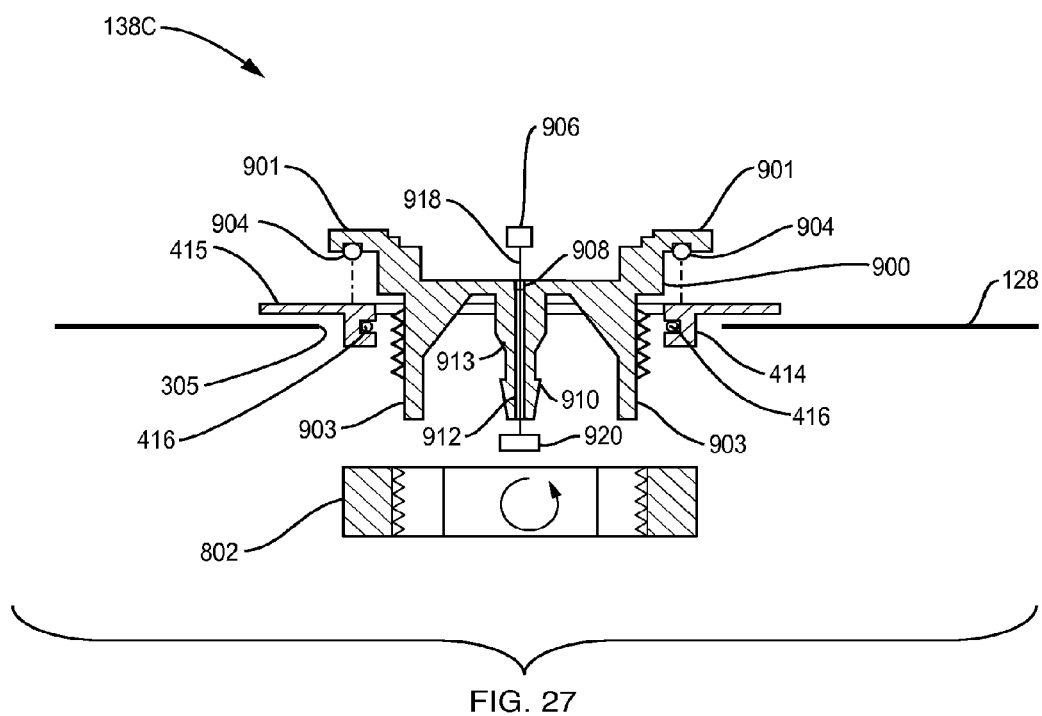
FIG. 27 is a schematic cross-sectional view of a bulkhead sensor unit according to an embodiment of the invention.

FIG. 27 shows a bulkhead sensor unit 138C having a similar configuration compared with the first bulkhead sparger 138A in FIG. 22. The sensor unit (138C) is provided for measuring at least one characteristic in the bag. The characteristic may be selected from the group consisting of a pH, dissolved gas, conductivity, cell density, temperature, a fluid flow, and a gas composition.

Bulkhead sensor unit 138C includes a sensor base 900 and sensor fastener 902. The sensor base 900 and sensor fastener 902 include screw grooves positioned identically to the first sparger base 400 and fastener 402 for enabling attachment of the sensor fastener 902 to the sensor base 900. Similar to the first bulkhead sparger 138A, the sensor base 900 and sensor fastener 902 fit within the first bushing 414 of the bag 128.

The sensor base 900 is seated thru the first bushing 414. The sensor base 900 generally includes a sensor base gasket 904, a sensor passageway 912, and a sensor base barb 910. The sensor base 900 is made from a plastic or other rigid polymeric material. The sensor base 900 is configured to include an open top section for the sensor 906 to be positioned within. The sensor base 900 includes flange outer sections 901 stretching along the outer edge of the upper portion of the base 900 for sitting along the top surface of the first bushing 414. The sensor base 900 also includes a sensor passageway 912 that forms a central section 913 from outside the bag 128 to an internal lower section of the bag. Outer lower sections 903 of the sensor base 900 surround the sensor passageway section 913 for protecting the sensor passageway section 913 from being damaged and have outer screw grooves for attaching to the sensor fastener 902.

The sensor base gasket 904 may be situated along a bottom surface of the outward sensor base flange sections 901 surrounding the sensor base 900. The sensor base gasket 904 is made from silicone rubber or a flexible polymeric material. In an alternative example, the sensor base gasket 904 is an o-ring.

The sensor base barb 910 is formed around the outer end of the central sensor passageway 912 section. The sensor base barb 910 can be utilized for connecting a sensor component to the sensor 906 as well as a hose for extending a wire from one device through the bulkhead sensor unit 138C.

The bulkhead sensor unit 138C may include a sensor fastener 902. The sensor fastener 902 is a bulkhead nut. The sensor fastener 902 includes threaded grooves along its internal surface to be used for attaching to the outer threaded grooves of the sensor base 900. This results in a tight fit between the sensor base 900 and the sensor fastener 902 forming an aseptic, non-permanent seal against the first bushing 414.

The bulkhead sensor unit 138C includes a sensor transducer 906 and a sensor controller 920. The sensor transducer 906 is attached to a wire 918 that is guided through the sensor passageway 912 in order to place the sensor transducer 906 at a desired position within the bag 128. The sensor section 906 is connected directly via wire 918 to the sensor controller 920 external to the bag 128. The sensor controller 920 monitors a level of a certain characteristic such as temperature or composition of gas. The sensor section 906 is able to float within a fluid in the space above the sensor base 900. As conditions change, the sensor section 906 constantly sends data regarding a certain characteristic to the controller 920 via wire 918.

The bulkhead sensor unit 138C may also include passageway sealing elements 908. These sealing elements 908 are used for filling in the spaces between the end of the sensor passageway 912 and the wire 918. The passageway sealing elements 908 are made from a plastic or rigid polymeric material.

Figure 28:
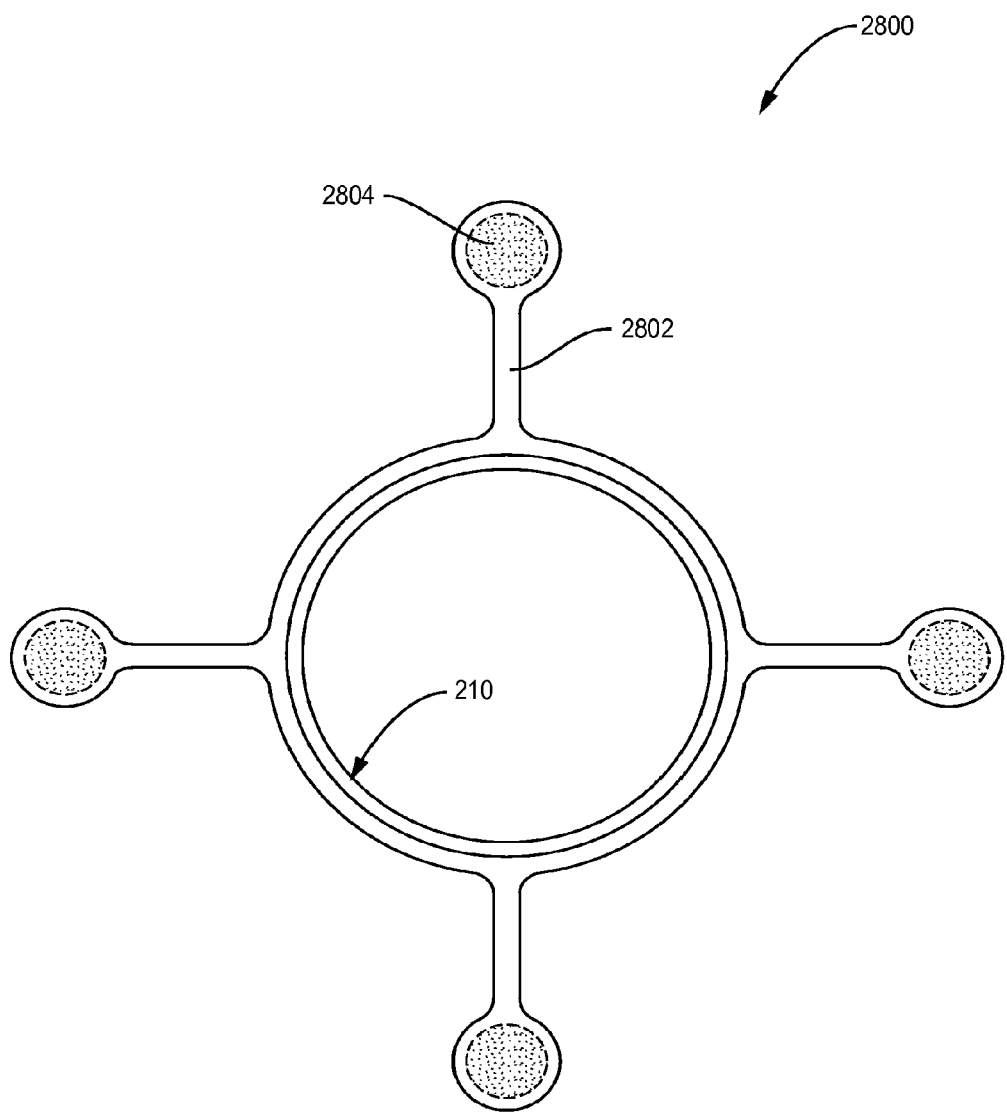
FIG. 28 is a schematic top planar view of an outrigger stabilizer for the agitator according to an embodiment of the invention.

FIG. 28 illustrates yet another aspect of the invention. With reference again to FIG. 2, when the maximum magnetic coupling force between the agitator or impeller and the external magnetic drive system 121 is exceeded by loads on the impeller or magnetic agitator 142, the agitator 142 decouples from the external magnetic drive system 121, and a temporary oscillation of first repulsive, then attractive force is produced. Such forces can push the agitator 142 perpendicularly away from the bag support structure wall 106. Because of this, the annular shaped boot structure, as shown in FIG. 28, may include an outrigger stabilizer 2800 with radially-extending talons 2802, that keep the annular shaped boot structure in close proximity to the bag support structure wall during this decoupling event, and allows the agitator to re-couple when the load on the agitator is reduced. It should be noted that the function of the outrigger stabilizer is not to prevent de-coupling from occurring, but rather to keep the agitator in sufficiently close proximity to the drive head to allow for re-coupling to occur. The outrigger stabilizers are lateral extensions that also function to support and distribute the magnetic force over a greater area, thereby reducing possible warping and/or scoring of the impeller plate.

The outrigger design allows for some perpendicular movement between the impeller and the container wall but does not allow for gross perpendicular movement that would allow the impeller to drift away from the area near the drive head. A purpose of limiting the movement of a decoupled impeller is to enable it to easily re-couple when the impeller load is reduced. The outrigger stabilizer does not provide the primary locating function of the impeller to the drive head. The primary locating function of the impeller to the drive head is provided by the torque coupling forces between the impeller and the drive head. There are several ways that the outrigger stabilizer could perform this function. The outrigger stabilizer could use magnetic coupling forces which would be distinct from the magnetic torque transmitting coupling forces to keep the annular shaped boot structure in close proximity to the container wall in the event of impeller decoupling. For example, a ferromagnetic plate can be inserted beneath the bag support structure wall, to provide an attractive coupling force for the encapsulated magnets 2804 on the outrigger stabilizer. Other methods such as using vacuum or electrostatic forces between the outrigger stabilizer and the container wall could be used to apply a force to the outrigger stabilizer to keep it in close proximity to the container wall in the event that the impeller decouples.

Turning now to the FIGS. 29-33, one further aspect of the invention has been shown in which a further device and method for connecting a disposable sensor to a flexible container has been shown. The device is suitable for use in connection with any kind of sensor, such as optical, electrochemical, conductance, impedance, pH, conductivity, dissolved oxygen, dissolved carbon dioxide, cell mass or ion selective. In the FIGS. 29-33, the sensors have a substantially cylindrical body, but the sensors and sensor housings may have any other shape. Further, the systems may comprise vessels and/or unit operations or components of cell culture, cell containment, bioreactor, and/or pharmaceutical manufacturing systems having one or more in-line sensing components that can provide real-time data for process control.

Figure 29:
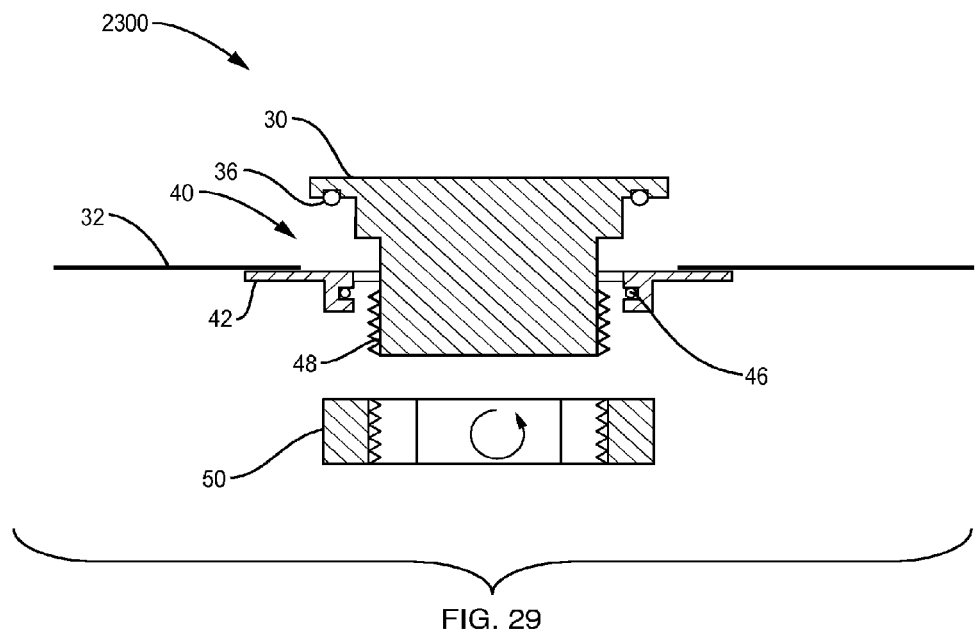
FIG. 29 is a partial cross sectional, elevational schematic depiction of a disposable sensor assembly including a bulkhead fitting for attaching to a flexible or semi-rigid wall, the threaded housing or threaded sensor body seated through a port plate.

As shown in FIGS. 29-33, a bulkhead disposable sensor assembly 2300 shown in FIG. 29 may comprise a bulkhead body 40 formed of plastic or other rigid polymeric material containing a monitoring sensor 30 mounted on one side of a flexible container or tubing 32, a plastic, rigid, or semi-rigid disc sealing element or polymeric port plate 42 mounted on the external side of the container or tubing wall 32, and plastic or flexible polymeric gaskets or o-rings 36. The threaded sensor body 30 or threaded housing 48 is seated through the polymeric port plate 42 containing secondary o-rings or gaskets 46, and a bulkhead nut 50 is threaded onto the bulkhead fitting body 40 and tightened against a sealing element such as an o-ring or gasket 36, 46 and the polymeric port plate 42 and container or tubing wall 32 to affect an aseptic, non-permanent seal. In one embodiment of the invention, the bulkhead disposable sensor assembly 2300 is removable. In another embodiment the bulkhead sensor assembly is not removable. By means of this attachment, the sensor body 30 is seated through the plate 42 and positioned such that the container or tubing wall 32 is sandwiched between the plate 42 and the bulkhead body 40, and a leak-tight seal is provided.

The term "bulkhead unit" or "bulkhead fitting," as used herein refers to an assembly having a portion thereof positioned on the interior of the flexible bag or tubing, and a portion thereof external to the bag or tubing.

Figure 30:
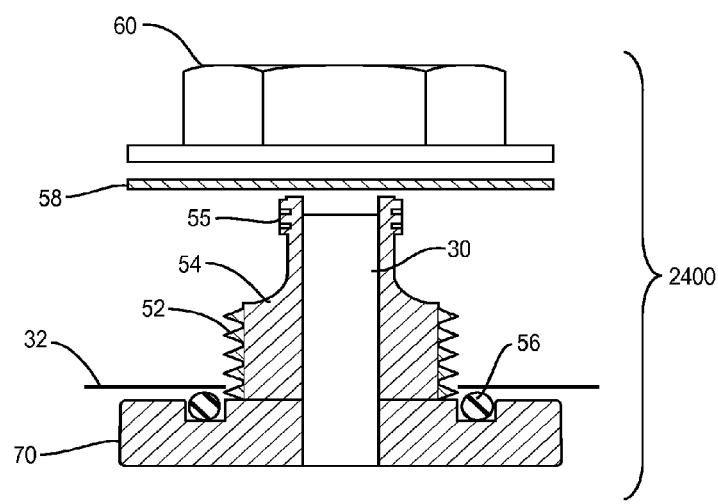
FIG. 30 is a partial cross sectional, elevational schematic depiction of a disposable sensor assembly including a bulkhead fitting having a bulkhead fastener that screws into a portion of the bulkhead base to secure the housing with sensor against a flexible wall of tubing or of a bag according to an embodiment of the invention.

As shown in FIG. 30, the bulkhead unit 2400 may include a bulkhead base 70 that fits within the rigid, semi-rigid or flexible bag or tubing wall 32, for attaching a permanently mounted disposable sensor 30 through the bag or tubing wall 32. The bulkhead base 70 includes a sensor housing 54, forming a sheath surrounding and holding sensor 30, for allowing permanent attachment of sensor 30 to the bulkhead base 70, and including threads, grooves, or slots 55 that allow for attachment of external supports, wiring, and cables if necessary. The bulkhead base 70 also includes a base sealing gasket 56 surrounding an upper portion of the base 70 for sealing the base 70 against the flexible or semi-rigid bag or tubing wall 32 when attached.

The bulkhead base 70 and housing portion 54 include outer threads or screw grooves 52. Typically, the bulkhead fastener 60 includes inner threads or screw grooves (not shown) for allowing the bulkhead fastener 60 to screw or rotate into the bulkhead base 70. The bulkhead unit 2400 also includes a spacer 58 such as a washer that is positioned between the bulkhead base 70 and the bulkhead fastener 60. The bulkhead base 70 fits within a passage in the spacer 58 and the inner threaded section of the bulkhead fastener 60 to form a tightened fit with the outer grooved section 52 of the bulkhead base 70.

Figure 31:
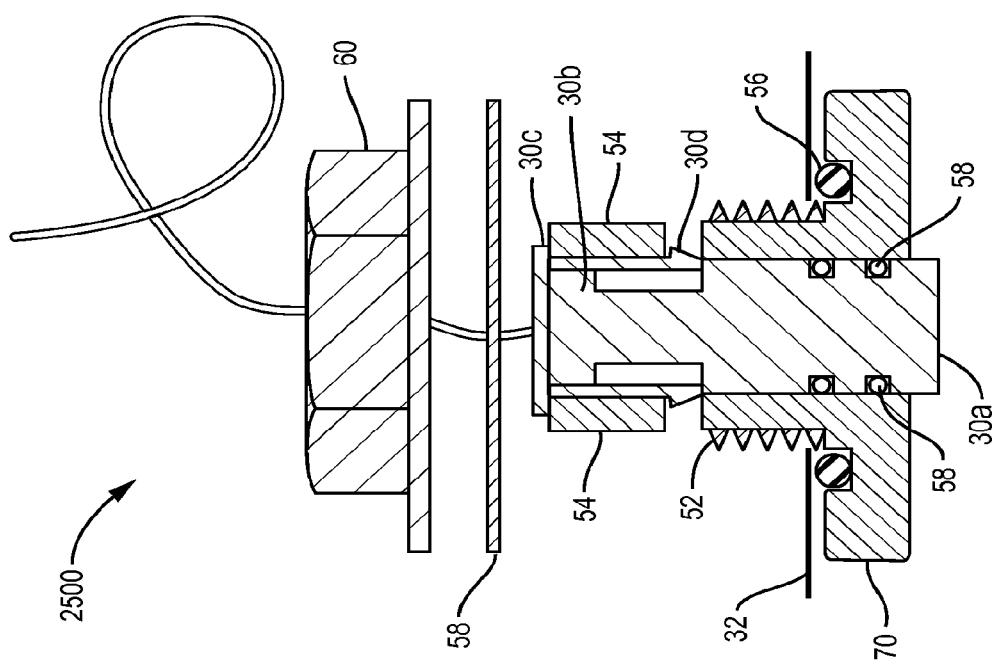
FIG. 31 is a partial cross sectional, elevational schematic depiction of a disposable sensor assembly including a bulkhead fitting having a bulkhead fastener and a retention feature on the sensor.

As shown in FIG. 31, the bulkhead unit 2500 may include a bulkhead base 70 that fits within the rigid, semi-rigid or flexible bag or tubing wall 32. The bulkhead base 70 also includes a base gasket 56 for sealing the base 70 against the bag or tubing wall 32 when attached. Bulkhead base 70 preferably contains at least a portion of disposable sensor 30. Disposable sensor 30 has a top portion 30b and a bottom portion 30a and is positioned such that in use, the bottom portion 30a of sensor 30 is in contact with a material such as a solution within the bag or tubing 32. Sensor gaskets 58 in contact with outer surface of the bottom portion 30b of sensor 30 form a seal between the sensor 30 and the bulkhead base 70. A sensor housing or sleeve 54, forms a sheath surrounding and holding the top portion 30b of sensor 30. Plate 30c in contact with the top portion 30b of sensor 30 includes threads, grooves, or slots (not shown) that allow for attachment of external supports, wiring, and cables if necessary. The top portion 30b of sensor 30 also has a barb or other type of retention feature 30d that prevents the sensor 30 from moving within the bulkhead unit 2500.

The bulkhead base 70 includes outer threads or screw grooves 52. The bulkhead fastener 60 includes inner threads or screw grooves (not shown) for allowing the bulkhead fastener 60 to rotate or screw into the bulkhead base 70. The bulkhead unit 2500 also includes a spacer 58 such as a washer that is positioned between the bulkhead base 70 and the bulkhead fastener 60. Spacer 58 protects the bag or tubing film 32 by preventing contact between the bulkhead fastener 60 and bag film 32. The bulkhead base 70 fits within a passage in the spacer 58. The inner threaded section of the bulkhead fastener 60 forms a tightened fit with the outer grooved section 52 of the bulkhead base 70.

Figure 32:
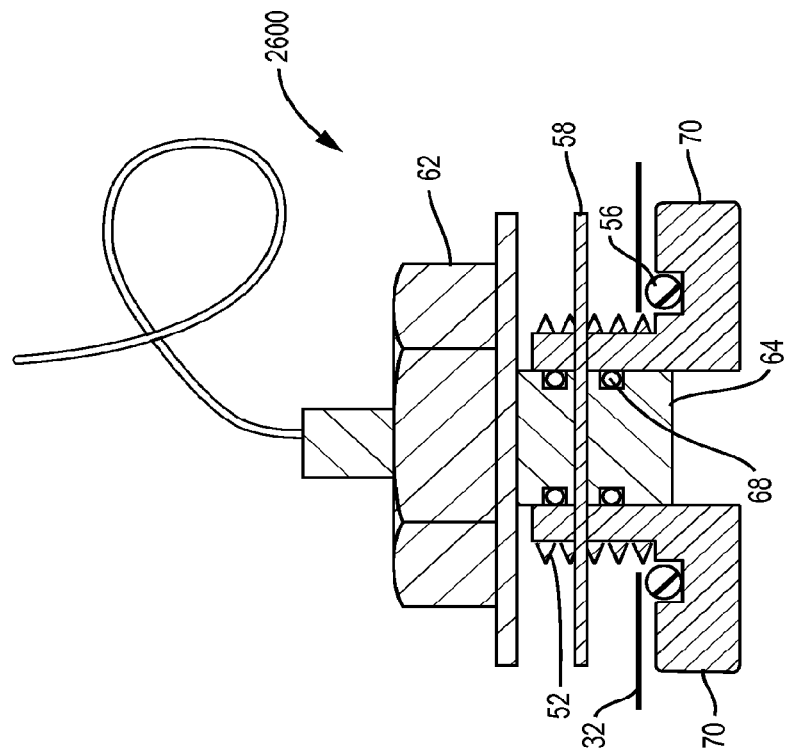
FIG. 32 is a partial cross sectional, elevational schematic depiction of a disposable sensor assembly including a bulkhead fitting having a bulkhead fastener and wherein the sensor and the bulkhead fastener are a one piece unit.

FIG. 32 depicts a bulkhead unit 2600 that includes a single-piece bulkhead fastener 62 and attached or integral sensor 64 having sensor gaskets 68 positioned to form a seal between the sensor 64 and the bulkhead sensor base 70. Bulkhead sensor base 70 fits within the rigid, semi-rigid or flexible bag or tubing wall 32. The bulkhead base 70 also includes a base gasket 56 for sealing the base 70 against the bag or tubing wall 32 when attached. The bulkhead base 70 includes outer threads or screw grooves 52. The bulkhead fastener 62 includes inner threads or screw grooves (not shown) for allowing the bulkhead fastener 62 to rotate or screw into the bulkhead base 70. Spacer 58 in one embodiment is a washer that is positioned between the bulkhead fastener 62 and the bag or tubing film 32, film 32 positioned above the bulkhead base 70.

Figure 33:
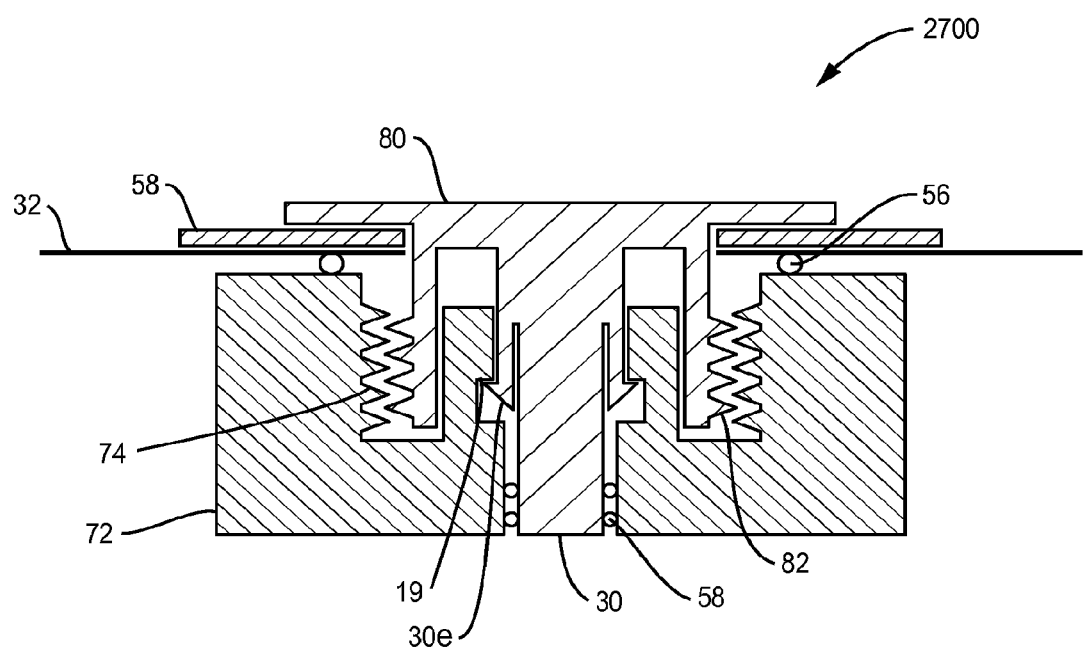
FIG. 33 is a partial cross sectional, elevational schematic depiction of a disposable sensor assembly including a bulkhead fitting having a bulkhead fastener and wherein the sensor has a retention fin and the bulkhead base has a cavity for receiving the retention fin.

FIG. 33 shows a bulkhead unit 2700 designed to maintain the bulkhead fastener 80 relatively close to the outside of the flexible bag or tubing wall 32 as compared to the above disclosed bulkhead units.

Bulkhead unit 2700 includes the bulkhead fastener 80 having a threaded portion 82 that is screwed or turned into bulkhead base 72 having a threaded or screw or groove portion 74 for receiving the bulkhead fastener 80. Disposable sensor 30 having optional retention feature 30e and sensor gaskets 58 is attached at its top portion to bulkhead fastener 80. The bulkhead base 72 has a cavity for receiving the retention fin 30e. The bottom portion of sensor 30 includes sensor gaskets 58 that form a seal with bulkhead base 74.

It should be noted that in any of the embodiments of the disposable sensor assembly described herein or in any other embodiment of the invention, the sensor may be positioned within the housing or the bulkhead fitting to be at any depth within the container or tubing. For example, the sensor may be at a depth that is even or flush with the inside wall of the container or tubing, or it may be, for example, at a depth of from about 1 millimeter to about 25 millimeters, or at a depth of from about 5 millimeters to about 13 millimeters inside the surface of the flexible or semi-rigid wall of the container or the tubing.

While this invention has been particularly shown and described with references to preferred embodiments thereof, it will be understood by those skilled in the art that various changes in form and details may be made therein without departing from the scope of the invention encompassed by the appended claims. Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A mixing system comprising:
a flexible bag (128) for containing a fluid;
a magnetic agitator (142) disposable in the bag (128) for mixing the fluid, the agitator (142) configured to rotate about an axis of rotation when magnetically coupled to an external magnetic drive system (121);
wherein the flexible bag is configured to be supported by a bag support structure (104) including a bag support structure wall (106) that at least partially surrounds, supports or contains the bag (128) during use and the flexible bag (128) is further adapted for deformation by a shaped portion of the bag support structure (104) to define a retainer for the agitator (142) within the bag (128) when the agitator (142) is magnetically coupled to the external magnetic drive system (121);
wherein the flexible bag is devoid of any rigid portion for receiving and holding the agitator in position within the flexible bag.

2. The mixing system of claim 1, wherein the shaped portion of the bag support structure (104) is at least one of a cavity, ring-like protuberance or protrusion (500), groove (600) or a post for retaining the flexible bag (128) and the fluid-agitating agitator.

3. The mixing system of claim 1, wherein the shaped portion of the bag support structure (104) is an annular groove (600) in an inner wall of the structure (104) and the agitator (142) further comprises a supporting structure (210) that at least partially surrounds the rotatable agitator (142) and fits within the groove (600).

4. The mixing system of claim 1, wherein the shaped portion of the bag support structure (142) is an annular protrusion (500) in an inner wall of the support structure (104) and the agitator further comprises a supporting structure (210) that fits against an inner side of the protrusion (500).

* * * * *